(12) United States Patent
Yashiro et al.

(10) Patent No.: US 9,184,388 B2
(45) Date of Patent: Nov. 10, 2015

(54) LAYERED STRUCTURE, ELECTRONIC DEVICE USING SAME, AROMATIC COMPOUND, AND METHOD FOR MANUFACTURING SAID COMPOUND

(75) Inventors: Arihiro Yashiro, Tsukuba (JP); Hideyuki Higashimura, Tsukuba (JP); Rui Ishikawa, Chikusei (JP); Masanobu Tanaka, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 307 days.

(21) Appl. No.: 13/812,678

(22) PCT Filed: Jul. 29, 2011

(86) PCT No.: PCT/JP2011/067550
§ 371 (c)(1),
(2), (4) Date: Jan. 28, 2013

(87) PCT Pub. No.: WO2012/015052
PCT Pub. Date: Feb. 2, 2012

(65) Prior Publication Data
US 2013/0119369 A1 May 16, 2013

(30) Foreign Application Priority Data
Jul. 29, 2010 (JP) .................. 2010-170252

(51) Int. Cl.
| | | |
|---|---|---|
| H01L 51/50 | (2006.01) | |
| H01L 51/00 | (2006.01) | |
| C07C 211/56 | (2006.01) | |
| C07C 211/63 | (2006.01) | |
| C07F 9/54 | (2006.01) | |
| C07F 9/572 | (2006.01) | |
| C08G 61/12 | (2006.01) | |
| C07D 209/86 | (2006.01) | |
| C07F 5/02 | (2006.01) | |

(52) U.S. Cl.
CPC .......... *H01L 51/0035* (2013.01); *C07C 211/56* (2013.01); *C07C 211/63* (2013.01); *C07D 209/86* (2013.01); *C07F 5/025* (2013.01); *C07F 9/5407* (2013.01); *C07F 9/5442* (2013.01); *C07F 9/5456* (2013.01); *C07F 9/5728* (2013.01); *C08G 61/12* (2013.01); *H01L 51/5056* (2013.01); *C08G 2261/1424* (2013.01); *C08G 2261/312* (2013.01); *C08G 2261/3162* (2013.01); *C08G 2261/411* (2013.01); *C08G 2261/512* (2013.01); *C08G 2261/91* (2013.01); *C08G 2261/92* (2013.01); *C08G 2261/95* (2013.01); *Y02E 10/549* (2013.01)

(58) Field of Classification Search
None
See application file for complete search history.

(56) References Cited

U.S. PATENT DOCUMENTS

| | | |
|---|---|---|
| 4,356,429 A | 10/1982 | Tang |
| 4,990,634 A | 2/1991 | Mukai et al. |
| 5,011,757 A | 4/1991 | Akasaki et al. |
| 5,023,356 A | 6/1991 | Mukai et al. |
| 5,028,505 A | 7/1991 | Akasaki et al. |
| 5,075,487 A | 12/1991 | Akasaki et al. |
| 5,121,029 A | 6/1992 | Hosokawa et al. |
| 5,621,131 A | 4/1997 | Kreuder et al. |
| 5,741,921 A | 4/1998 | Kreuder et al. |
| 5,777,070 A | 7/1998 | Inbasekaran et al. |
| 5,814,244 A | 9/1998 | Kreuder et al. |
| 6,309,763 B1 | 10/2001 | Woo et al. |
| 6,458,909 B1 | 10/2002 | Spreitzer et al. |
| 6,541,602 B1 | 4/2003 | Spreitzer et al. |
| 6,544,670 B1 | 4/2003 | Kitano et al. |
| 6,841,269 B2 | 1/2005 | Kitano et al. |
| 6,897,473 B1 | 5/2005 | Burroughes et al. |
| 6,984,459 B1 | 1/2006 | Noguchi et al. |

(Continued)

FOREIGN PATENT DOCUMENTS

| | | |
|---|---|---|
| EP | 0 517 542 A1 | 12/1992 |
| EP | 0 707 020 A2 | 4/1996 |

(Continued)

OTHER PUBLICATIONS

Cao et al., Triphenylamine and Fluorene Based Cationic Conjugated Polyelectrolytes: Synthesis and Characterization, 2009, Macromol. Chem. Phys., 210, 150-160.*

Cao et al., Synthesis of novel triphenylamine-based conjugated polyelectrolytes and their application as hole transporting layers in polymeric light-emitting diodes, 2006, J. Mater. Chem., 16, 2387-2394.*

Translation of Solvent Handbook, Kodansha Scientific, 1976, p. 39.

Translation of Development of Organic EL Device & Their Materials, CMC Publishing Co., Ltd., 2006, pp. 81-88.

Translation of Development of Organic EL Device & Their Materials, CMC Publishing Co., Ltd., 2006, pp. 45-67.

(Continued)

*Primary Examiner* — Gregory Clark
(74) *Attorney, Agent, or Firm* — Sughrue Mion, PLLC

(57) ABSTRACT

The present invention provides: a layered structure having a substrate and a hole injection and/or hole transport layer comprising an aromatic compound having, on a side chain, at least one type of group having a cationic center;
an electronic device having the layered structure;
an aromatic compound having, on a hydrocarbon side chain, at least one type of group having a cationic center;
an aromatic compound having a leaving group on a hydrocarbon side chain;
and a method for manufacturing the aromatic compound having, on a hydrocarbon side chain, at least one type of group having a cationic center, the method comprising reacting the aromatic compound having a leaving group on a hydrocarbon side chain with a specific nitrogen compound, phosphorus compound, sulfur compound, or a combination of two or more of these compounds, thereby converting the aromatic compound into an onium salt thereof. When used as an electronic device material, and particularly as a hole transport and/or hole injection material, the aromatic compound can achieve a higher current density at a given voltage.

5 Claims, No Drawings

(56) References Cited

U.S. PATENT DOCUMENTS

| | | |
|---|---|---|
| 2004/0075381 A1 | 4/2004 | Burroughes et al. |
| 2005/0184658 A1 | 8/2005 | Burroughes et al. |
| 2006/0246613 A1 | 11/2006 | Burroughes et al. |
| 2006/0263917 A1 | 11/2006 | Burroughes et al. |
| 2007/0096082 A1 | 5/2007 | Gaynor et al. |
| 2008/0015269 A1 | 1/2008 | Bazan et al. |
| 2008/0197768 A1 | 8/2008 | Conway et al. |
| 2009/0096363 A1 | 4/2009 | Burroughes et al. |
| 2010/0171100 A1 | 7/2010 | Nakatani et al. |
| 2010/0176377 A1 | 7/2010 | Fukushima et al. |
| 2012/0008068 A1 | 1/2012 | Doi et al. |

FOREIGN PATENT DOCUMENTS

| | | |
|---|---|---|
| GB | 2 340 304 A | 2/2000 |
| GB | 2 348 316 A | 9/2000 |
| JP | 57-51781 A | 3/1982 |
| JP | 63-70257 A | 3/1988 |
| JP | 63-175860 A | 7/1988 |
| JP | 2-135359 A | 5/1990 |
| JP | 2-135361 A | 5/1990 |
| JP | 2-209988 A | 8/1990 |
| JP | 3-37992 A | 2/1991 |
| JP | 3-152184 A | 6/1991 |
| JP | 5-263073 A | 10/1993 |
| JP | 6-1972 A | 1/1994 |
| JP | 8-239655 A | 9/1996 |
| JP | 9-111233 A | 4/1997 |
| JP | 10-324870 A | 12/1998 |
| JP | 2000-80167 A | 3/2000 |
| JP | 2001-123156 A | 5/2001 |
| JP | 2004-168999 A | 6/2004 |
| JP | 2006-295203 A | 10/2006 |
| JP | 2007-162009 A | 6/2007 |
| JP | 2007-246801 A | 9/2007 |
| WO | 97/09394 A1 | 3/1997 |
| WO | 98/27136 A1 | 6/1998 |
| WO | 99/54385 A1 | 10/1999 |
| WO | 00/22027 A1 | 4/2000 |
| WO | 01/19834 A1 | 3/2001 |
| WO | 2005/052027 A1 | 6/2005 |
| WO | 2006/137434 A1 | 12/2006 |
| WO | 2007/126929 A2 | 11/2007 |
| WO | WO 2007/126929 | * 11/2007 ............ H01L 51/00 |

OTHER PUBLICATIONS

Translation of Denki-Kagaku Binran (Electrochemical Handbook), 5th edition, 2000, pp. 26-45.

International Preliminary Report on Patentability and Written Opinion dated Feb. 14, 2013 in International Application No. PCT/JP2011/067550 to Sumitomo Chemical Co., Ltd., et al.

Wei Shi et al., "Triphenylamine and Fluorene Based Cationic Conjugated Polyelectrolytes: Synthesis and Characterization", Macromolecular Chemistry and Physics, 2009, pp. 150-160, vol. 210.

Seung-Hwan OH et al., "Novel cationic water-soluble polyfluorene derivatives with ion-transporting side groups for efficient electron injection in PLEDs", Organic Electronics 8, 2007, pp. 773-783.

Solvent Handbook, Kodansha Scientific, 1976, pp. 37-39.

Development of Organic EL Device & Their Materials, CMC Publishing Co., Ltd., 2006, pp. 45-67; pp. 81-88.

Data book on work function of organic thin films, 2nd Edition, CMC Publishing Co., Ltd., 2006, pp. 44-59.

Denki-Kagaku Binran (Electrochemical Handbook), 5th edition, 2000, pp. 26-45.

Communication dated Jun. 30, 2015 from the Japanese Patent Office in counterpart application No. 2011-167786.

* cited by examiner

LAYERED STRUCTURE, ELECTRONIC DEVICE USING SAME, AROMATIC COMPOUND, AND METHOD FOR MANUFACTURING SAID COMPOUND

CROSS REFERENCE TO RELATED APPLICATIONS

This application is a National Stage of International Application No. PCT/JP2011/067550 filed Jul. 29, 2011, claiming priority based on Japanese Patent Application No. 2010-170252 filed Jul. 29, 2010, the contents of all of which are incorporated herein by reference in their entirety.

TECHNICAL FIELD

The present invention relates to a layered structure, an electronic device using the layered structure, an aromatic compound, a method for manufacturing the compound, and a hole injection and/or hole transport material containing the compound.

BACKGROUND ART

The development of various materials that constitute organic EL devices has been actively pursued in recent years. In the development of organic EL devices, the development of materials having superior charge injection properties and/or charge transport properties is a very important task.

The development of compounds containing a triarylamine structure as charge injection and/or charge transport materials has seen a significant increase in activity in recent years. For example, polymers containing a triarylamine structure in which an ammonium salt that improves the charge injection properties is linked via an ether bond have been disclosed (Non-Patent Document 1).

DOCUMENTS OF RELATED ART

Non-Patent Documents

[Non-Patent Document 1] W. Shi et al., Macromolecular Chem. and Phys., 2009, Vol. 2, pages 150 to 160.

However, in order to develop electronic devices having superior performance, the development of compounds that are capable of ensuring a higher current density at a given voltage has been required.

SUMMARY OF THE INVENTION

Problems to be Solved by the Invention

Accordingly, objects of the present invention are to provide a novel aromatic compound which can achieve a higher current density at a given voltage and can be used as a layered structure or a material for an electronic device, and particularly as a hole transport and/or hole injection material, and also to provide a method for manufacturing the aromatic compound, a hole injection and/or hole transport material, and an electronic device.

Means to Solve the Problems

As a result of intensive investigation aimed at achieving the above objects, the inventors of the present invention were able to complete the present invention. In other words, the present invention provides a layered structure disclosed in the following <1> or <2>.

<1>
A layered structure having a substrate, and a hole injection and/or hole transport layer comprising an aromatic compound having a structural unit represented by formula (1) below:

[Chemical Formula 1]

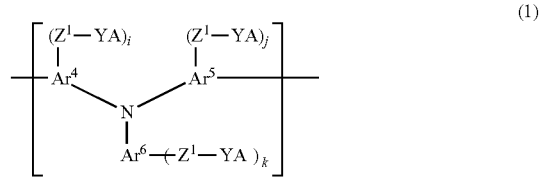

wherein $Ar^4$ represents an (i+2)-valent aromatic group which may have a substituent, $Ar^5$ represents a (j+2)-valent aromatic group which may have a substituent, and $Ar^6$ represents a (k+1)-valent aromatic group which may have a substituent, but at least two of $Ar^4$, $Ar^5$ and $Ar^6$ may be mutually bonded to form at least one ring, each $Z^1$ independently represents a divalent group, each Y independently represents a group represented by formula (2-1), (2-2) or (2-3) below, each A independently represents a monovalent or divalent or higher anion, and when at least one A is a divalent or higher anion, the above structural unit may further have another cation, and each of i, j and k independently represents an integer of 0 or greater, provided that i+j+k is an integer of 1 or greater, $$—N^+R^1R^2R^3 \qquad (2\text{-}1)$$

$$—P^+R^1R^2R^3 \qquad (2\text{-}2)$$

$$—S^+R^1R^2 \qquad (2\text{-}3)$$

wherein for each of formulas (2-1), (2-2) and (2-3), each of $R^1$, $R^2$ and $R^3$ independently represents a hydrogen atom or a monovalent hydrocarbon group which may have a substituent, but at least two of $R^1$, $R^2$ and $R^3$ may be mutually bonded to form at least one ring.

<2>
The layered structure according to <1>, wherein the hole injection and/or hole transport layer has a crosslinked structure.

Further, the present invention provides an electronic device disclosed in the following <3>.

<3>
An electronic device having the layered structure according to <1> or <2>.

Furthermore, the present invention provides an aromatic compound disclosed in the following <4> or <5>, namely, an aromatic compound having, on a hydrocarbon side chain, at least one type of group having a cationic center.

<4>
An aromatic compound having a structural unit represented by formula (3) below:

[Chemical Formula 2]

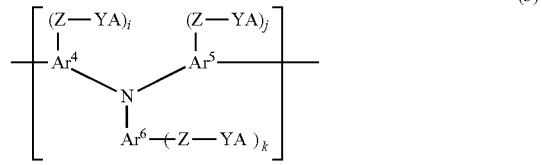

wherein $Ar^4$ represents an (i+2)-valent aromatic group which may have a substituent, $Ar^5$ represents a (j+2)-valent aromatic group which may have a substituent, and $Ar^6$ represents a (k+1)-valent aromatic group which may have a substituent, but at least two of $Ar^4$, $Ar^5$ and $Ar^6$ may be mutually bonded to form at least one ring, each Z independently represents a divalent hydrocarbon group which may have a substituent, each Y independently represents a group represented by formula (2-1), (2-2) or (2-3) below, each A independently represents a monovalent or divalent or higher anion, and when at least one A is a divalent or higher anion, the above structural unit may further have another cation, and each of i, j and k independently represents an integer of 0 or greater, provided that i+j+k is an integer of 1 or greater,

(2-1)

(2-2)

(2-3)

wherein for each of formulas (2-1), (2-2) and (2-3), each of $R^1$, $R^2$ and $R^3$ independently represents a hydrogen atom or a monovalent hydrocarbon group which may have a substituent, but at least two of $R^1$, $R^2$ and $R^3$ may be mutually bonded to form at least one ring.

<5>

The aromatic compound according to <4>, represented by formula (4) below:

[Chemical Formula 3]

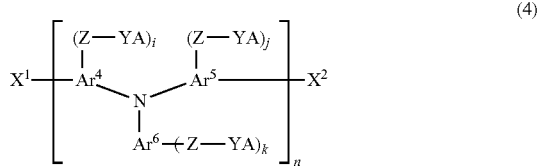
(4)

wherein $Ar^4$, $Ar^5$, $Ar^6$, A, Y, Z, i, j and k represent the same meanings as defined above, and when a plurality of one or more of $Ar^4$, $Ar^5$, $Ar^6$, A, Y, Z, i, j and k exists, each item of the plurality may be the same as, or different from, each other item of the plurality, n represents an integer of 1 or greater, and each of $X^1$ and $X^2$ independently represents a hydrogen atom or a monovalent group.

Further, the present invention provides an aromatic compound disclosed in the following <6> or <7>, namely, an aromatic compound having at least one type of primary to quaternary ammonium ion on a hydrocarbon side chain.

<6>

The aromatic compound according to <4>, which is an aromatic compound having a structural unit represented by formula (5) below:

[Chemical Formula 4]

(5)

wherein each of $Ar^1$, $Ar^2$ and $Ar^3$ independently represents a divalent aromatic group which may have a substituent, but at least two of $Ar^1$, $Ar^2$ and $Ar^3$ may be mutually bonded to form at least one ring, Z represents a divalent hydrocarbon group which may have a substituent, each of $R^1$, $R^2$ and $R^3$ independently represents a hydrogen atom or a monovalent hydrocarbon group which may have a substituent, but at least two of $R^1$, $R^2$ and $R^3$ may be mutually bonded to form at least one ring, A represents a monovalent or divalent or higher anion, and when A is a divalent or higher anion, the above structural unit may further have another cation.

<7>

The aromatic compound according to <6>, represented by formula (6) below:

[Chemical Formula 5]

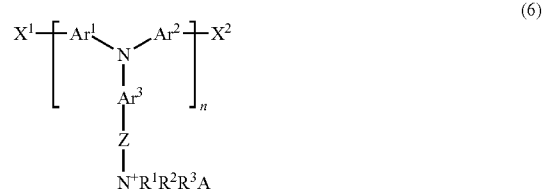
(6)

wherein $Ar^1$, $Ar^2$, $Ar^3$, A, Z, $R^1$, $R^2$ and $R^3$ represent the same meanings as defined above, and when a plurality of one or more of $Ar^1$, $Ar^2$, $Ar^3$, A, Z, $R^1$, $R^2$ and $R^3$ exists, each item of the plurality may be the same as, or different from, each other item of the plurality, n represents an integer of 1 or greater, and each of $X^1$ and $X^2$ independently represents a hydrogen atom or a monovalent group.

Further, the present invention provides an aromatic compound disclosed in the following <8> or <9>, namely, an aromatic compound having a leaving group on a hydrocarbon side chain.

<8>

An aromatic compound having a structural unit represented by formula (7) below:

[Chemical Formula 6]

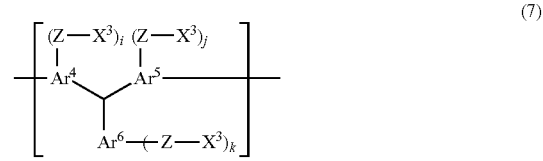
(7)

wherein $Ar^4$ represents an (i+2)-valent aromatic group which may have a substituent, $Ar^5$ represents a (j+2)-valent aromatic group which may have a substituent, and $Ar^6$ represents a (k+1)-valent aromatic group which may have a substituent, but at least two of $Ar^4$, $Ar^5$ and $Ar^6$ may be mutually bonded to form at least one ring, each Z independently represents a divalent hydrocarbon group which may have a substituent, each $X^3$ independently represents a leaving group, and each of i, j and k independently represents an integer of 0 or greater, provided that i+j+k is an integer of 1 or greater.

<9>

The aromatic compound according to <8>, represented by formula (8) below:

[Chemical Formula 7]

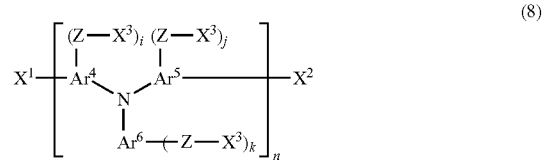
(8)

wherein $Ar^4$, $Ar^5$, $Ar^6$, $X^3$, Z, i, j and k represent the same meanings as defined above, and when a plurality of one or more of $Ar^4$, $Ar^5$, $Ar^6$, $X^3$, Z, i, j and k exists, each item of the plurality may be the same as, or different from, each other item of the plurality, n represents an integer of 1 or greater, and each of $X^1$ and $X^2$ independently represents a hydrogen atom or a monovalent group.

Furthermore, the present invention provides an aromatic compound disclosed in the following <10> or <11>, namely, an aromatic compound having a leaving group on a hydrocarbon side chain.

<10>

The aromatic compound according to <8>, which is an aromatic compound having a structural unit represented by formula (9) below:

[Chemical Formula 8]

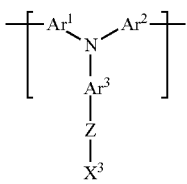

(9)

wherein each of $Ar^1$, $Ar^2$ and $Ar^3$ independently represents a divalent aromatic group which may have a substituent, but at least two of $Ar^1$, $Ar^2$ and $Ar^3$ may be mutually bonded to form at least one ring, Z represents a divalent hydrocarbon group which may have a substituent, and $X^3$ represents a leaving group.

<11>

The aromatic compound according to <10>, represented by formula (10) below:

[Chemical Formula 9]

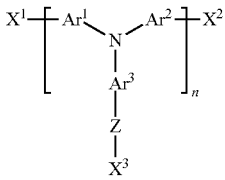

(10)

wherein Z, $Ar^1$, $Ar^2$, $Ar^3$ and $X^3$ represent the same meanings as defined above, and when a plurality of one or more of Z, $Ar^1$, $Ar^2$, $Ar^3$ and $X^3$ exists, each item of the plurality may be the same as, or different from, each other item of the plurality, n represents an integer of 1 or greater, and each of $X^1$ and $X^2$ independently represents a hydrogen atom or a monovalent group.

Moreover, the present invention provides a method for manufacturing an aromatic compound disclosed in the following <12>, <13> or <14>.

<12>

A method for manufacturing the aromatic compound according to <4> having a structural unit represented by formula (3), the method comprising reacting the aromatic compound according to <8> having a structural unit represented by formula (7) with a nitrogen compound represented by formula (11-1) below, a phosphorus compound represented by formula (11-2) below, a sulfur compound represented by formula (11-3) below, or a combination of two or more of these compounds, thereby converting the aromatic compound to an onium salt thereof:

$NR'R^2R^3$ (11-1)

$PR^1R^2R^3$ (11-2)

$SR^1R^2$ (11-3)

wherein for each of formulas (11-1), (11-2) and (11-3), each of $R^1$, $R^2$ and $R^3$ independently represents a hydrogen atom or a monovalent hydrocarbon group which may have a substituent, but at least two of $R^1$, $R^2$ and $R^3$ may be mutually bonded to form at least one ring.

<13>

The method according to <12>, wherein the aromatic compound according to <8> having a structural unit represented by formula (7) is the aromatic compound according to <9> represented by formula (8), and the aromatic compound according to <4> having a structural unit represented by formula (3) is the aromatic compound according to <5> represented by formula (4).

<14>

The method according to <12>, wherein the nitrogen compound, the phosphorus compound, the sulfur compound or the combination of two or more of these compounds is reacted with a leaving group represented by $X^3$ in the aromatic compound according to <8> having a structural unit represented by formula (7).

Moreover, the present invention provides a method for manufacturing an aromatic compound disclosed in the following <15> or <16>.

<15>

The method according to <14>, wherein the nitrogen compound represented by formula (11-1) is reacted with a leaving group represented by $X^3$ in the aromatic compound according to <10> having a structural unit represented by formula (9), thereby manufacturing the aromatic compound according to <6> having a structural unit represented by formula (5).

<16>

The method according to <15>, wherein the aromatic compound according to <10> having a structural unit represented by formula (9) is the aromatic compound according to <11> represented by formula (10), and the aromatic compound according to <6> having a structural unit represented by formula (5) is the aromatic compound according to <7> represented by formula (6).

Effects of the Invention

The aromatic compound of the present invention can be applied to electronic devices, can be used particularly favorably as a hole injection and/or hole transport material, and enables a higher current density to be achieved at a given voltage.

EMBODIMENTS OF THE INVENTION

The present invention is described below. First is an explanation of the terminology that is used frequently in this description. Unless terms are specifically limited, the following definitions are used.

In the present description, the expression "may have a substituent" includes both the case where the hydrogen atoms that constitute the compound or group mentioned immediately prior to the expression are unsubstituted, and those cases where some or all of the hydrogen atoms are substituted with a substituent, and in the case of substitution with a substituent, means substitution with a substituent such as a halogen atom, hydroxyl group, amino group, nitro group, hydrocarbyl group of 1 to 30 carbon atoms or hydrocarbyloxy group of 1 to 30 carbon atoms,
wherein among these substituents, substitution with a halogen atom, a hydrocarbyl group of 1 to 18 carbon atoms or a hydrocarbyloxy group of 1 to 18 carbon atoms is preferable,
substitution with a hydrocarbyl group of 1 to 12 carbon atoms or a hydrocarbyloxy group of 1 to 12 carbon atoms is more preferable,
substitution with a hydrocarbyl group of 1 to 10 carbon atoms or a hydrocarbyloxy group of 1 to 10 carbon atoms is still more preferable,
and substitution with a hydrocarbyl group of 1 to 6 carbon atoms or a hydrocarbyloxy group of 1 to 6 carbon atoms is particularly preferable.
The substituents for the hydrocarbyl group and hydrocarbyloxy group and the like may each be linear, branched or cyclic.
In the present description, the expression "may have a substituent" may be rephrased as "may be substituted" or "has or does not have a substituent".
Examples of the aforementioned halogen atom include a fluorine atom, chlorine atom, bromine atom and iodine atom, wherein a fluorine atom, chlorine atom or bromine atom is preferable, and a fluorine atom or chlorine atom is more preferable.
The aforementioned hydrocarbyl group may be any of linear, branched or cyclic. Examples of the hydrocarbyl group include a methyl group, ethyl group, 1-propyl group, 2-propyl group, 1-butyl group, 2-butyl group, tert-butyl group, pentyl group, hexyl group, octyl group, decyl group, dodecyl group, 2-ethylhexyl group, 3,7-dimethyloctyl group, cyclopropyl group, cyclopentyl group, cyclohexyl group, 1-adamantyl group, 2-adamantyl group, norbornyl group, ammoniummethyl group, benzyl group, α,α-dimethylbenzyl group, 1-phenethyl group, 2-phenethyl group, vinyl group, propenyl group, butenyl group, oleyl group, eicosapentaenyl group, docosahexaenyl group, 2,2-diphenylvinyl group, 1,2,2-triphenylvinyl group, 2-phenyl-2-propenyl group, phenyl group, 2-tolyl group, 4-tolyl group, 4-trifluoromethylphenyl group, 4-methoxyphenyl group, 4-cyanophenyl group, 2-biphenylyl group, 3-biphenylyl group, 4-biphenylyl group, terphenylyl group, 3,5-diphenylphenyl group, 3,4-diphenylphenyl group, pentaphenylphenyl group, 4-(2,2-diphenylvinyl)phenyl group, 4-(1,2,2-triphenylvinyl)phenyl group, fluorenyl group, 1-naphthyl group, 2-naphthyl group, 9-anthryl group, 2-anthryl group, 9-phenanthryl group, 1-pyrenyl group, chrysenyl group, naphthacenyl group and coronyl group,
preferable groups include a methyl group, ethyl group, 1-propyl group, 2-propyl group, 1-butyl group, 2-butyl group, tert-butyl group, pentyl group, hexyl group, octyl group, decyl group, dodecyl group, 2-ethylhexyl group, 3,7-dimethyloctyl group, benzyl group, α,α-dimethylbenzyl group, 1-phenethyl group, 2-phenethyl group, vinyl group, propenyl group, butenyl group, oleyl group, eicosapentaenyl group, docosahexaenyl group, 2,2-diphenylvinyl group, 1,2,2-triphenylvinyl group, 2-phenyl-2-propenyl group, phenyl group, 2-tolyl group, 4-tolyl group, 4-trifluoromethylphenyl group, 4-methoxyphenyl group, 4-cyanophenyl group, 2-biphenylyl group, 3-biphenylyl group, 4-biphenylyl group, terphenylyl group, 3,5-diphenylphenyl group, 3,4-diphenylphenyl group, pentaphenylphenyl group, 4-(2,2-diphenylvinyl)phenyl group, 4-(1,2,2-triphenylvinyl)phenyl group, fluorenyl group, 1-naphthyl group, 2-naphthyl group, 9-anthryl group, 2-anthryl group and 9-phenanthryl group, more preferable groups include a methyl group, ethyl group, 1-propyl group, 2-propyl group, 1-butyl group, 2-butyl group, tert-butyl group, pentyl group, hexyl group, octyl group, 2-ethylhexyl group, 3,7-dimethyloctyl group, benzyl group and phenyl group, and still more preferable groups include a methyl group, ethyl group, 1-propyl group, 2-propyl group, 1-butyl group, 2-butyl group, tert-butyl group, pentyl group and hexyl group.
The aforementioned hydrocarbyloxy group may be any of linear, branched or cyclic.
Examples of the hydrocarbyloxy group include a methoxy group, ethoxy group, 1-propanoxy group, 2-propanoxy group, 1-butoxy group, 2-butoxy group, tert-butoxy group, pentyloxy group, hexyloxy group, octyloxy group, decyloxy group, dodecyloxy group, 2-ethylhexyloxy group, 3,7-dimethyloctyloxy group, cyclopropanoxy group, cyclopentyloxy group, cyclohexyloxy group, 1-adamantyloxy group, 2-adamantyloxy group, norbornyloxy group, ammoniumethoxy group, trifluoromethoxy group, benzyloxy group, α,α-dimethylbenzyloxy group, 2-phenethyloxy group, 1-phenethyloxy group, phenoxy group, alkoxyphenoxy groups, alkylphenoxy groups, 1-naphthyloxy group, 2-naphthyloxy group and pentafluorophenyloxy group,
preferable groups include a methoxy group, ethoxy group, 1-propanoxy group, 2-propanoxy group, 1-butoxy group, 2-butoxy group, tert-butoxy group, pentyloxy group, hexyloxy group, octyloxy group, decyloxy group, dodecyloxy group, 2-ethylhexyloxy group and 3,7-dimethyloctyloxy group,
and more preferable groups include a methoxy group, ethoxy group, 1-propanoxy group, 2-propanoxy group, 1-butoxy group, 2-butoxy group, tert-butoxy group, pentyloxy group and hexyloxy group.
In the present description, Ph represents a phenyl group, and Im represents an N-imidazolyl group.
In the present description, a "hole injection and/or hole transport material" refers to a material having one of, or both, hole injection properties and hole transport properties. Further, in the present description, a "hole injection and/or hole transport layer" refers to a layer having one of, or both, hole injection properties and hole transport properties.
An embodiment for implementing the present invention is described below.
The present invention provides a layered structure having a substrate, and a hole injection and/or hole transport layer comprising an aromatic compound having a structural unit represented by the following formula (1).

[Chemical Formula 10]

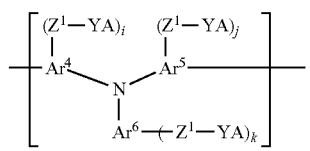

(1)

In the formula, $Ar^4$ represents an (i+2)-valent aromatic group which may have a substituent, $Ar^5$ represents a (j+2)-valent aromatic group which may have a substituent, and $Ar^6$ represents a (k+1)-valent aromatic group which may have a substituent, but at least two of $Ar^4$, $Ar^5$ and $Ar^6$ may be mutually bonded to form at least one ring, each $Z^1$ independently represents a divalent group, each Y independently represents a group represented by formula (2-1), (2-2) or (2-3) below, each A independently represents a monovalent or divalent or higher anion, and when at least one A is a divalent or higher anion, the above structural unit may further have another cation, and each of i, j and k independently represents an integer of 0 or greater, provided that i+j+k is an integer of 1 or greater.

Examples of $Ar^4$ and $Ar^5$ include monocyclic aromatic groups such as a 1,3-phenylene group and 1,4-phenylene group;

condensed ring aromatic groups such as a naphthalene-1,3-diyl group, naphthalene-1,4-diyl group, naphthalene-1,5-diyl group, naphthalene-1,6-diyl group, naphthalene-1,7-diyl group, naphthalene-2,6-diyl group and naphthalene-2,7-diyl group;

and heteroaromatic groups such as a pyridine-2,5-diyl group, pyridine-2,6-diyl group, quinoxaline-2,6-diyl group and thiophene-2,5-diyl group.

Among these, monocyclic aromatic groups and condensed ring aromatic groups are preferable, a group selected from the group consisting of a 1,3-phenylene group, 1,4-phenylene group, naphthalene-1,4-diyl group, naphthalene-1,5-diyl group, naphthalene-2,6-diyl group and naphthalene-2,7-diyl group is more preferable, a 1,3-phenylene group or 1,4-phenylene group is still more preferable, and a 1,4-phenylene group is particularly preferable. These groups may have a substituent.

Examples of $Ar^6$ include monocyclic aromatic groups such as a phenyl group and a phenylene group (for example, a 1,3-phenylene group or 1,4-phenylene group);

condensed ring aromatic groups such as a naphthalen-1-yl group, naphthalen-2-yl group and naphthalenediyl group (for example, a naphthalene-1,3-diyl group, naphthalene-1,4-diyl group, naphthalene-1,5-diyl group, naphthalene-1,6-diyl group, naphthalene-1,7-diyl group, naphthalene-2,6-diyl group or naphthalene-2,7-diyl group); and heteroaromatic groups such as a pyridine-2,5-diyl group, pyridin-2-yl group, quinoxalin-2-yl group and thiophen-2-yl group.

Among these, monocyclic aromatic groups and condensed ring aromatic groups are preferable, a group selected from the group consisting of phenylene groups and naphthalenediyl groups is more preferable, and a phenylene group is still more preferable. These groups may have a substituent.

$Z^1$ represents a divalent group. A divalent hydrocarbon group which may be substituted is preferably used as the divalent group. Among such groups, a divalent hydrocarbon group of 1 to 50 carbon atoms which may be substituted is preferable, a divalent hydrocarbon group of 2 to 40 carbon atoms which may be substituted is more preferable, and in terms of ensuring good solvent solubility and improving the workability within elements and devices, a divalent hydrocarbon group of 6 to 30 carbon atoms which may be substituted is still more preferable. The number of carbon atoms in $Z^1$ is preferably not more than 50, as this facilitates an increase in the effect of introducing the portion represented by —YA. Among the above divalent hydrocarbon groups, in terms of ensuring good solvent solubility and improving the workability within elements and devices, an alkylene group is preferable. A linear group is preferred as the alkylene group.

Y is a group represented by formula (2-1), (2-2) or (2-3) below, and belongs to the group of monovalent groups having a cationic center.

  —N⁺R¹R²R³  (2-1)

  —P⁺R¹R²R³  (2-2)

  —S⁺R¹R²  (2-3)

In each of formulas (2-1), (2-2) and (2-3), each of $R^1$, $R^2$ and $R^3$ independently represents a hydrogen atom or a monovalent hydrocarbon group which may be substituted, but at least two of $R^1$, $R^2$ and $R^3$ may be mutually bonded to form at least one ring.

Each of $R^1$, $R^2$ and $R^3$ independently represents a hydrogen atom or a monovalent hydrocarbon group (hydrocarbyl group) which may be substituted, but at least two of $R^1$, $R^2$ and $R^3$ may be mutually bonded to form at least one ring.

When the hydrocarbyl group is an alkyl group, an alkyl group of 1 to 20 carbon atoms is preferable, and examples include linear, branched or cyclic alkyl groups such as a methyl group, ethyl group, n-propyl group, iso-propyl group, n-butyl group, sec-butyl group, iso-butyl group, tert-butyl group, n-pentyl group, 2,2-dimethylpropyl group, n-hexyl group, cyclohexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group and n-eicosyl group.

Further, when the hydrocarbyl group is an aryl group, an aryl group of 6 to 20 carbon atoms is preferable, and examples include a phenyl group, 1-naphthyl group, 2-napthyl group, 3-phenanthryl group and 2-anthryl group.

The ring formed when at least two of $R^1$, $R^2$ and $R^3$ are mutually bonded is a hydrocarbon ring, a heterocyclic ring, or a combination thereof, wherein the heterocyclic ring may contain only the nitrogen atom, phosphorus atom or sulfur atom bonded to Z, or may also contain another hetero atom such as a nitrogen atom or oxygen atom besides this nitrogen atom, phosphorus atom or sulfur atom.

A represents a monovalent or divalent or higher anion, but when A represents a divalent or higher anion, the above structural unit may further have another cation. Specific examples of A include a fluoride ion, chloride ion, bromide ion, iodide ion, sulfate ion, nitrate ion, carbonate ion, acetate ion, perchlorate ion, tetrafluoroborate ion, hexafluorophosphate ion, hexafluoroantimonate ion, hexafluoroarsenate ion, methanesulfonate ion, trifluoromethanesulfonate ion, trifluoroacetate ion, benzenesulfonate ion, para-toluenesulfonate ion, dodecylbenzenesulfonate ion, tetraphenylborate ion, tetrakis(pentafluorophenyl)borate ion, tetra(N-imidazolyl)borate ion, and polymer compounds containing a repeating unit having one or more of these ion structures.

Preferable anions include a fluoride ion, chloride ion, bromide ion, iodide ion, tetrafluoroborate ion, hexafluorophosphate ion, trifluoromethanesulfonate ion, tetraphenylborate ion and tetra(N-imidazolyl)borate ion.

Examples of the other cation include alkali metal ions such as a lithium ion, sodium ion and potassium ion. Further, a divalent or higher anion A within a structural unit represented by formula (1) may undergo charge cancellation by bonding with a cation such as $N^+$, $P^+$ or $S^+$ within another structural unit represented by formula (1).

Each of i, j and k independently represents an integer of 0 or greater. However, i+j+k must be an integer of 1 or greater, and is preferably an integer of 1 to 6, more preferably an integer of 1 to 3, and still more preferably 1.

If the total of all the structural units in the aromatic compound having the structural unit represented by formula (1) is deemed 100 mol %, then the proportion of the structural unit represented by formula (1) is preferably within a range from not less than 1 mol % to not more than 100 mol %, more preferably within a range from not less than 1 mol % to not more than 99 mol %, still more preferably within a range from not less than mol % to not more than 90 mol %, still more preferably within a range from not less than 10 mol % to not more than 80 mol %, and particularly preferably within a range from not less than 20 mol % to not more than 70 mol %. The aromatic compound is preferably a copolymer rather than a homopolymer.

Specific examples of the aforementioned formula (1) include the following structural units (1a) to (1c), (1f), (1g), and (1i) to (1z). In these formulas, m represents an integer of 1 to 50, and is preferably an integer of 2 to 40, more preferably an integer of 2 to 30, and still more preferably an integer of 6 to 30.
[Chemical Formula 11]
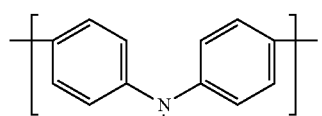
(1a)
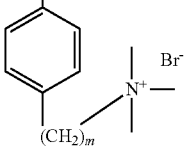
(1b)
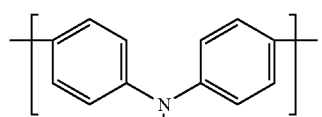
(1c)
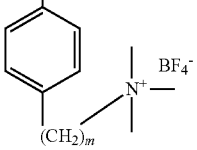
(1f)
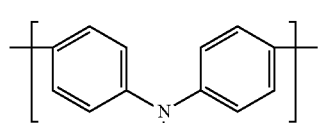
(1g)
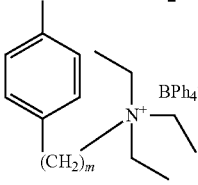
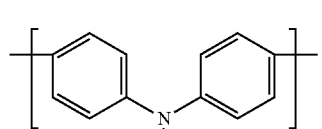
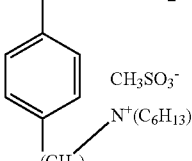
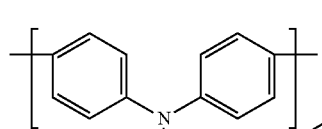
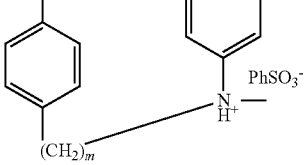
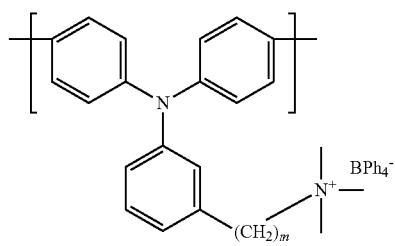
(1i)
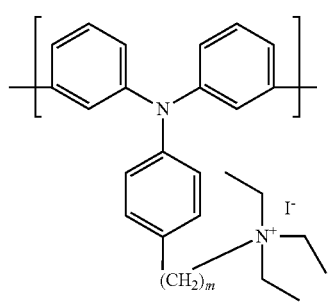
(1j)
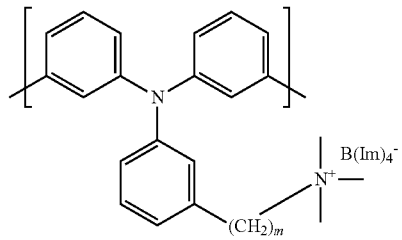
(1k)
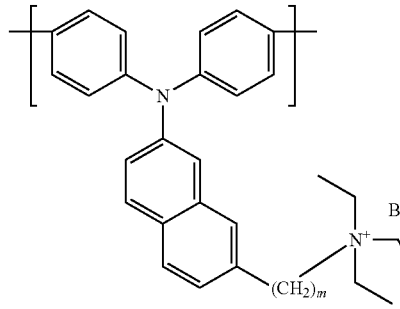
(1l)
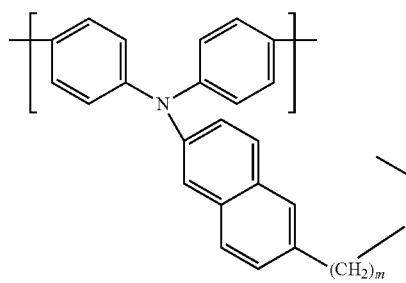
(1m)

[Chemical Formula 12]
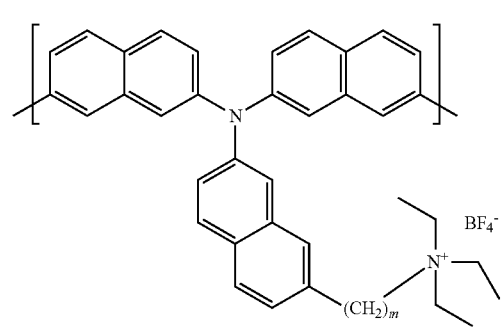
(1n)
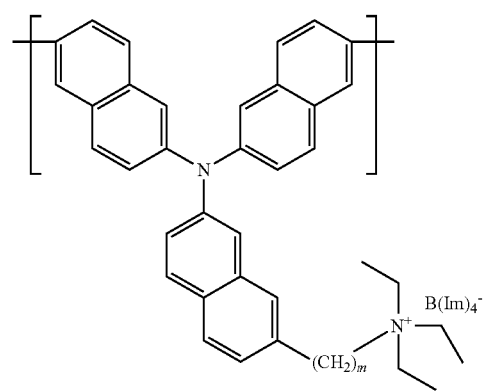
(1o)
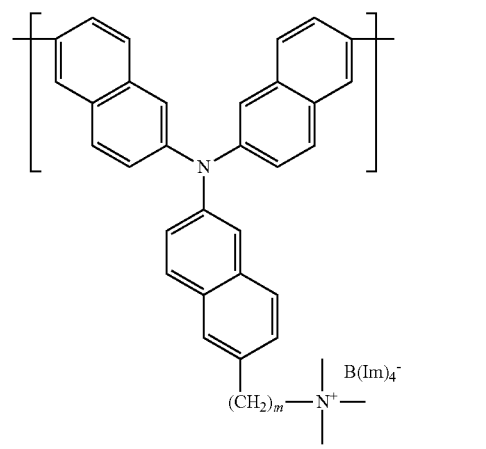
(1p)
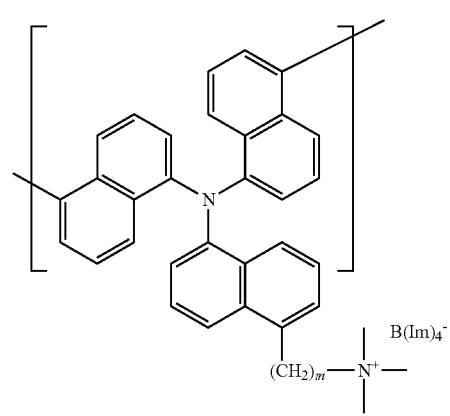
(1q)
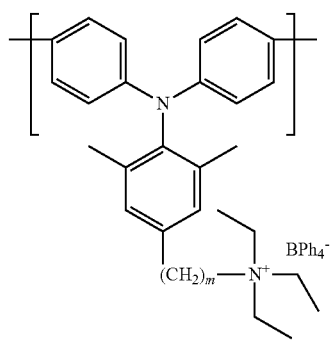
(1r)
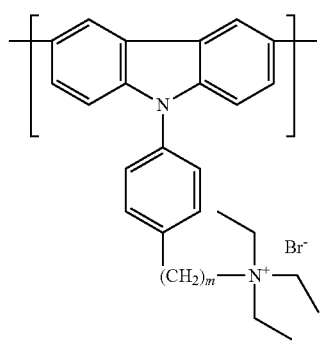
(1s)
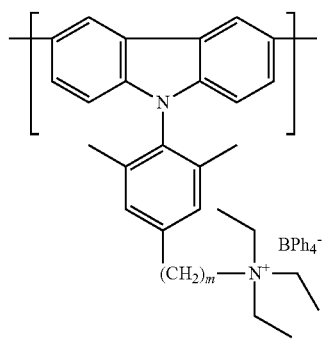
(1t)
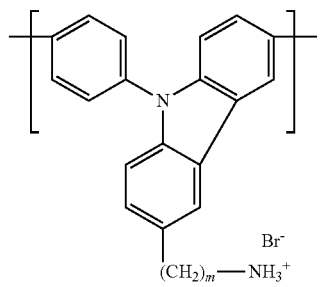
(1u)
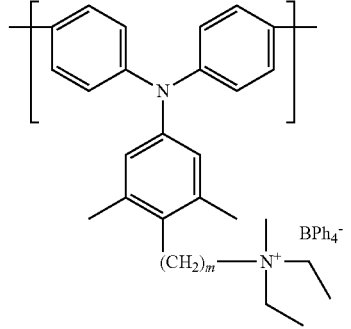
(1v)

-continued
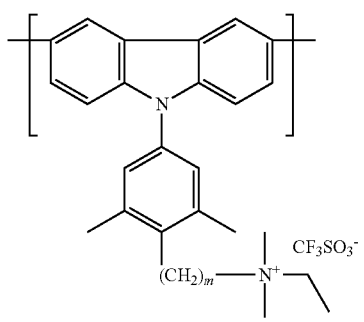
(1w)
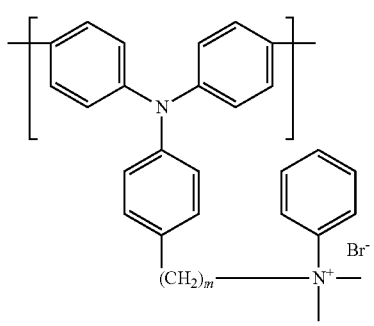
(1x)
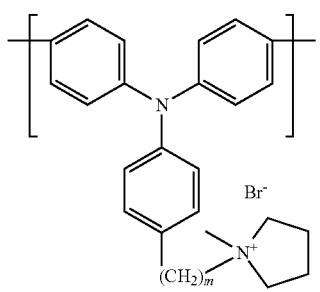
(1y)
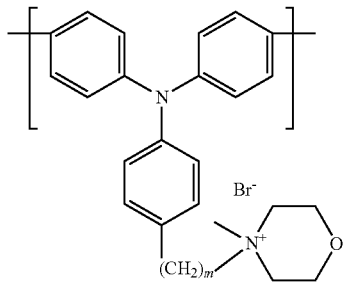
(1z)
Further specific examples of formula (1) include the following structural units (1a2) to (1k2), and (1m2) to (1r2). m has the same meaning as defined above.
[Chemical Formula 13]
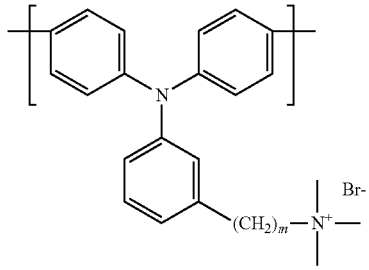
(1a2)
-continued
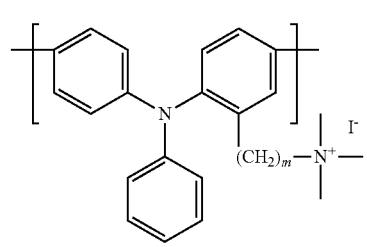
(1b2)
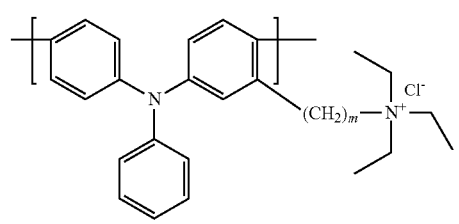
(1c2)
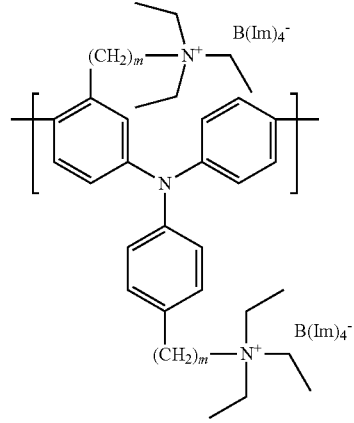
(1d2)
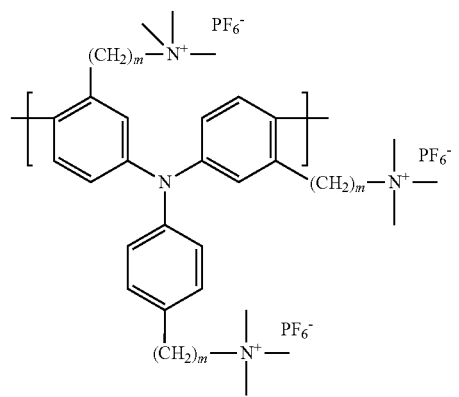
(1e2)

(1f2)
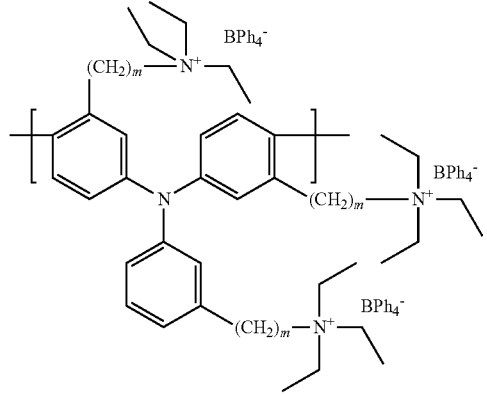
(1g2)
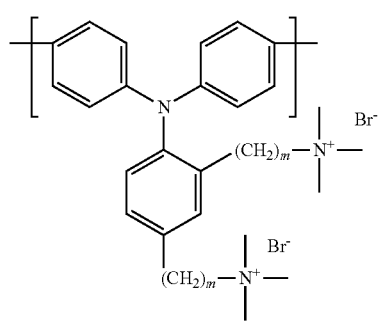
(1h2)
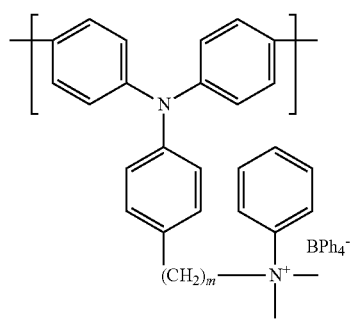
(1i2)
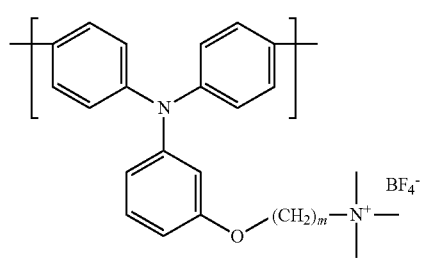
[Chemical Formula 14]
(1j2)
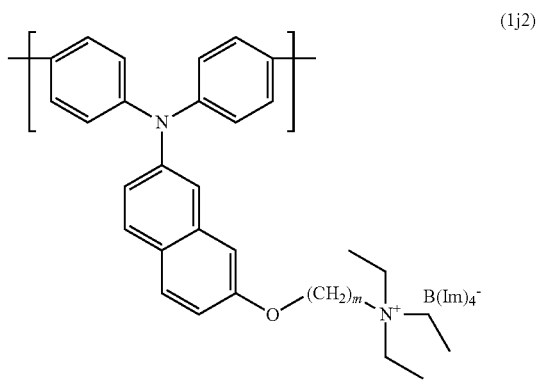
(1k2)
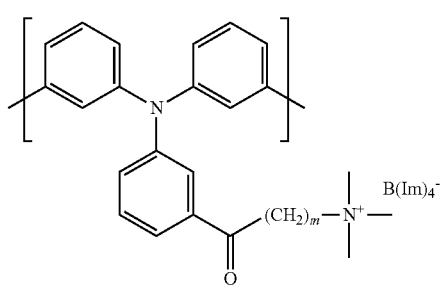
(1m2)
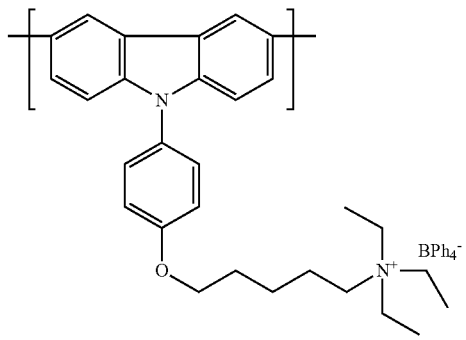
(1n2)
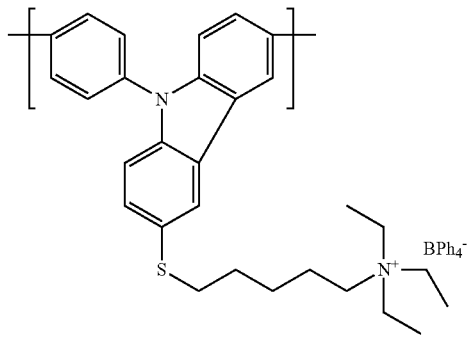

(1o2)
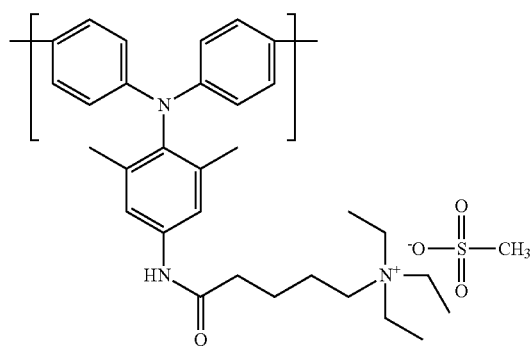
(1p2)
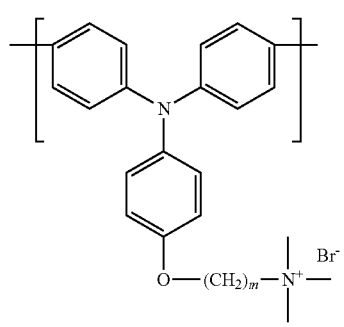
(1q2)
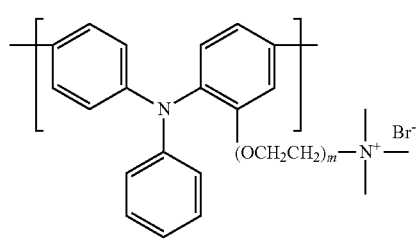
(1r2)
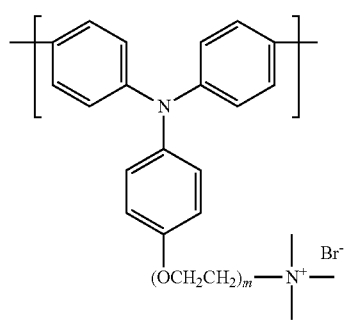
Still further specific examples of formula (1) include the following structural units (1a3) to (1 m3), and (1o3) to (1q3). m has the same meaning as defined above.
[Chemical Formula 15]
(1a3)
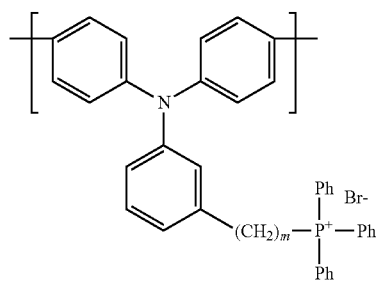
(1b3)
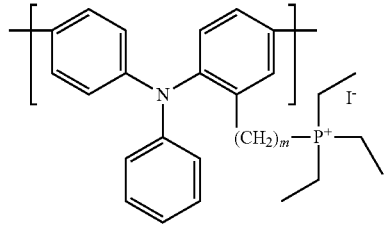
(1c3)
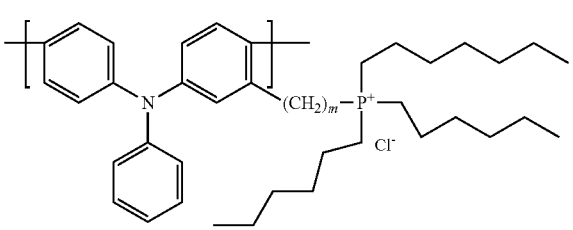
(1d3)
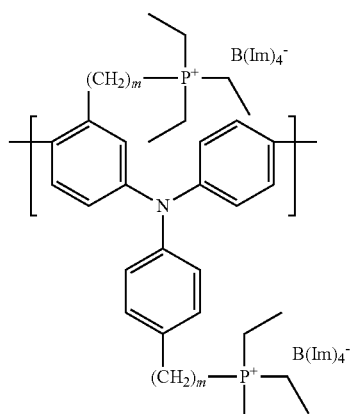
(1e3)
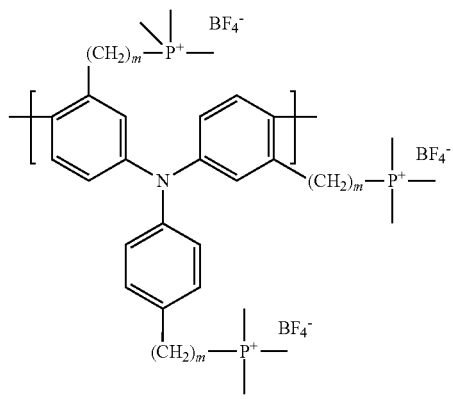

-continued
(1f3)
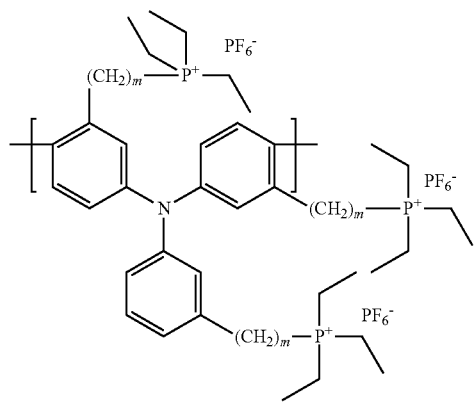
(1g3)
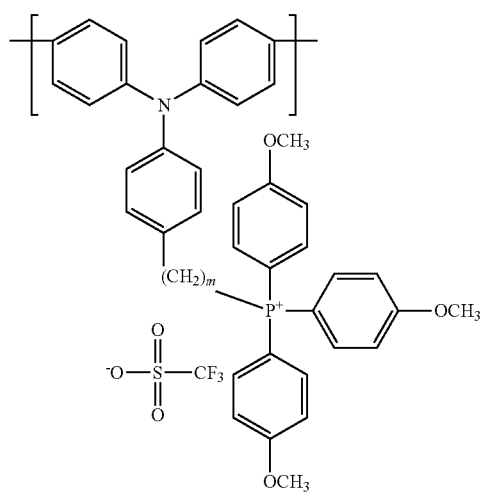
(1h3)
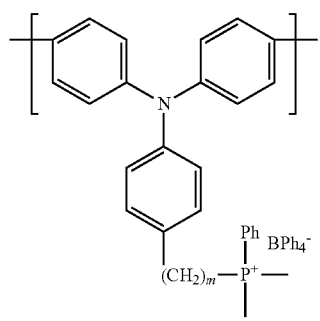
(1i3)
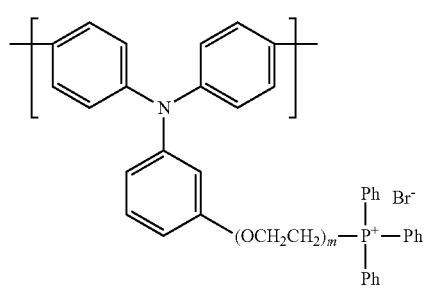
-continued
[Chemical Formula 16]
(1j3)
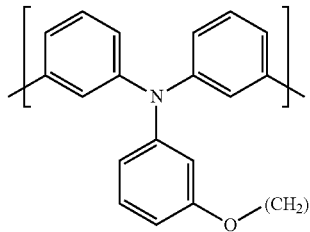
(1k3)
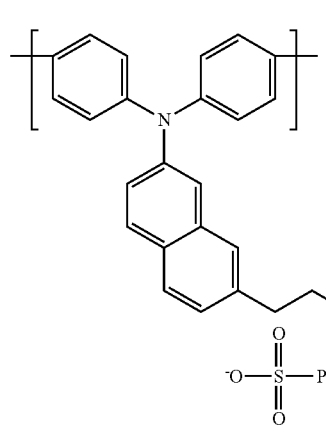
(1l3)
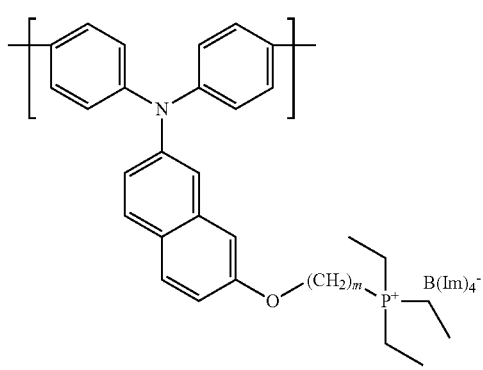
(1m3)
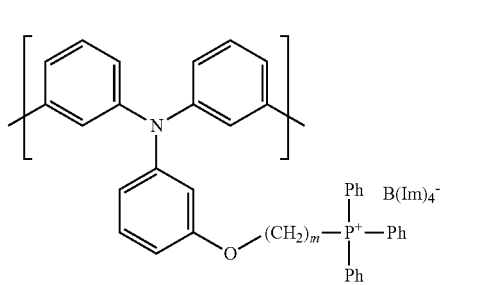

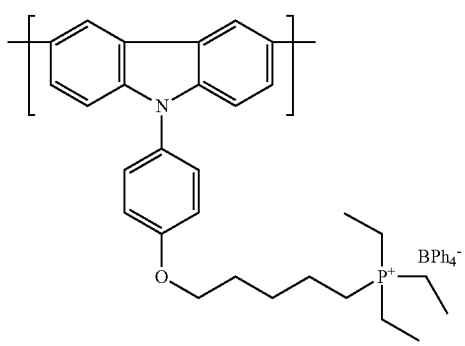
(1o3)
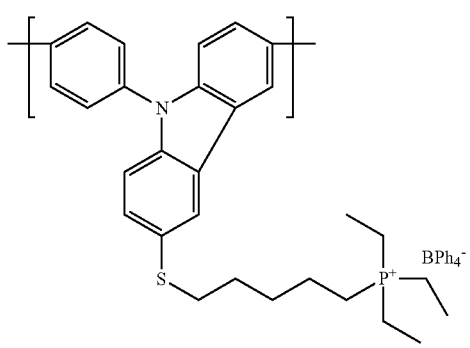
(1p3)
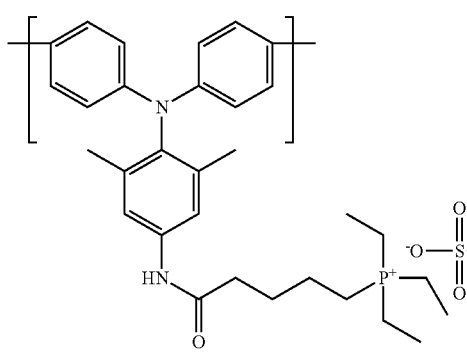
(1q3)
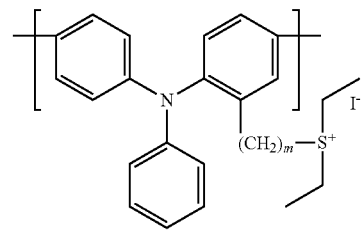
(1b4)
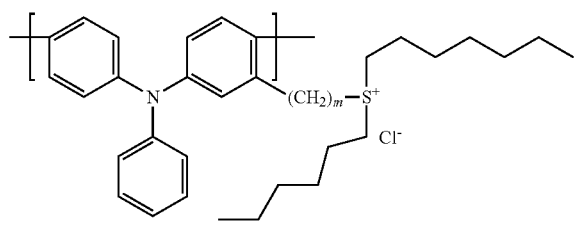
(1c4)
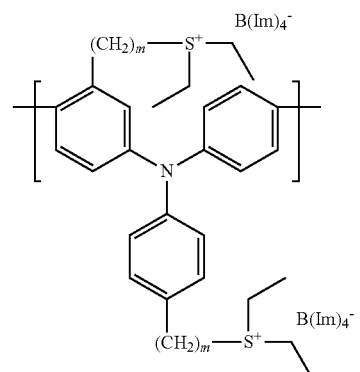
(1d4)
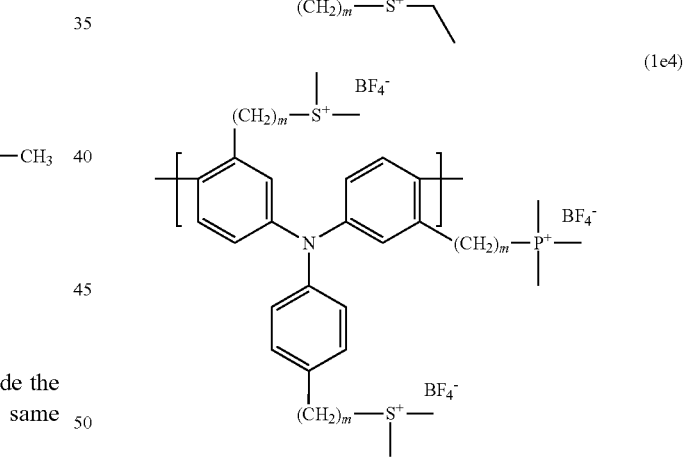
(1e4)
Still further specific examples of formula (1) include the following structural units (1a4) to (1q4). m has the same meaning as defined above.
[Chemical Formula 17]
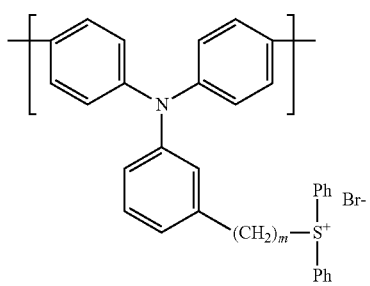
(1a4)
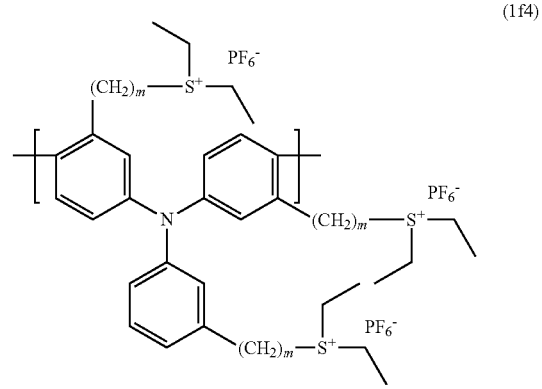
(1f4)

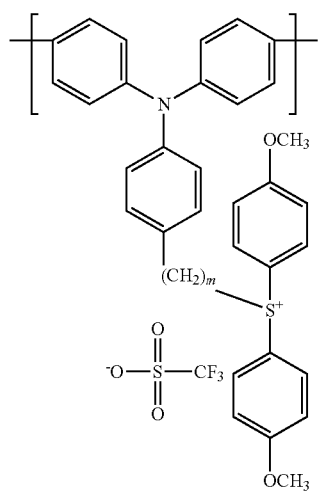 (1g4)
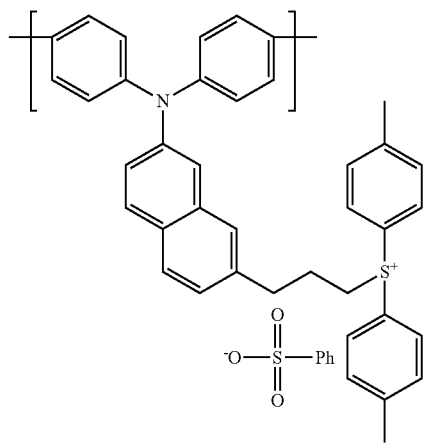 (1k4)
[Chemical Formula 18]
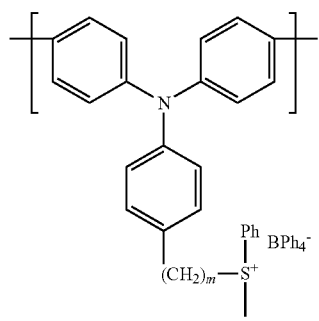 (1h4)
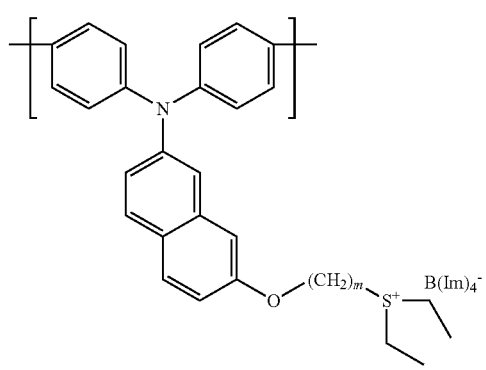 (1l4)
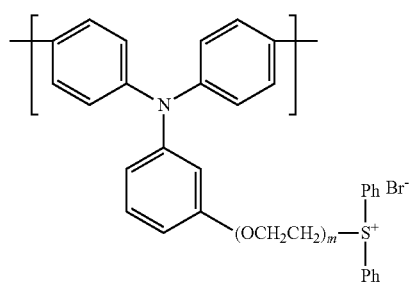 (1i4)
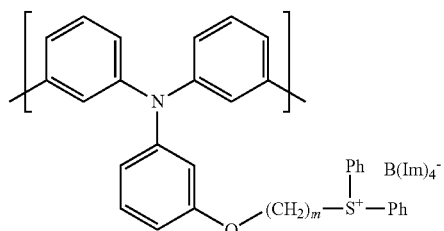 (1m4)
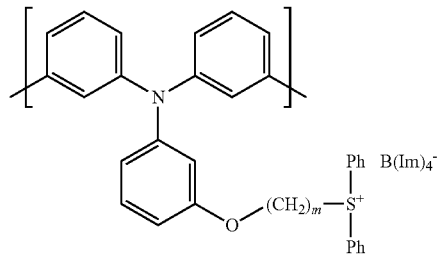 (1j4)
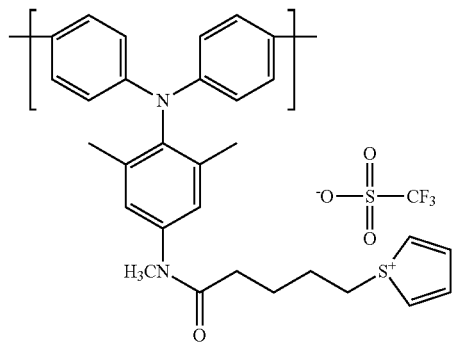 (1n4)

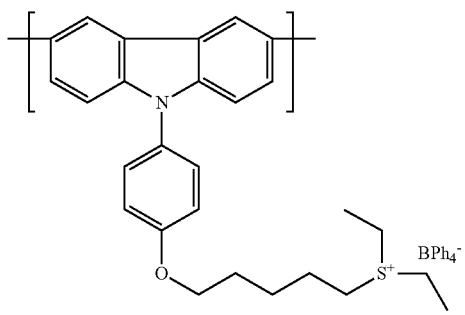
(1o4)

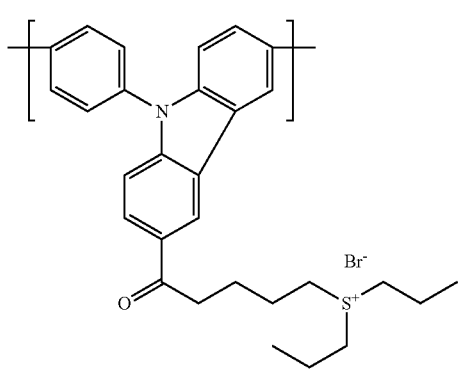
(1p4)

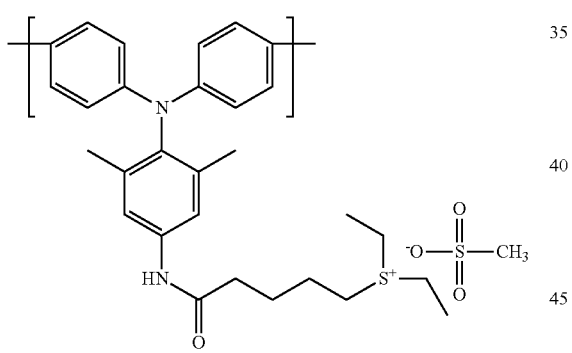
(1q4)

Among these structural units (1a) to (1c), (1f), (1g), (1i) to (1z), (1a2) to (1k2), (1 m2) to (1r2), (1a3) to (1 m3), (1o3) to (1q3), and (1a4) to (1q4), in terms of achieving high polarity and facilitating solubility in high-polarity solvents, and suppressing thermal decomposition, (1a) to (1c), (1f), (1g), and (1i) to (1z) are preferable.

Among these structural units (1a) to (1c), (1f), (1g), and (1i) to (1z), structural units (1a), (1b), (1c), (1l), (1k), (1m), (1n), (1p), (1q), (1r), (1s), (1t), (1v), (1y) and (1z) are preferable, (1a), (1c), (1l), (1p), (1q), (1r), (1t), (1y) and (1z) are more preferable, and (1a), (1c), (1r), (1t) and (1y) are still more preferable.

Further, the aromatic compound having a structural unit represented by formula (1) may also contain, besides the structural unit represented by formula (1), a structural unit represented by the following formula (12) as a repeating unit.

[Chemical Formula 19]

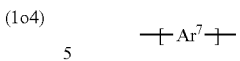
(12)

In the formula, $Ar^7$ represents a divalent aromatic group, and some or all of the hydrogen atoms in the aromatic group may be substituted with a group selected from the group consisting of a fluorine atom, an alkyl group of 1 to 20 carbon atoms which may have a substituent, an alkoxy group of 1 to 20 carbon atoms which may have a substituent, an aryl group of 6 to 20 carbon atoms which may have a substituent, an aryloxy group of 6 to 20 carbon atoms which may have a substituent, and an acyl group of 2 to 20 carbon atoms which may have a substituent.

In formula (12), examples of $Ar^7$ include divalent monocyclic aromatic groups such as a 1,3-phenylene group and 1,4-phenylene group; divalent condensed ring aromatic groups such as a naphthalene-1,3-diyl group, naphthalene-1,4-diyl group, naphthalene-1,5-diyl group, naphthalene-1,6-diyl group, naphthalene-1,7-diyl group, naphthalene-2,6-diyl group and naphthalene-2,7-diyl group; and divalent heteroaromatic groups such as a pyridine-2,5-diyl group, pyridine-2,6-diyl group, quinoxaline-2,6-diyl group and thiophene-2,5-diyl group.

Other examples of the formula (12), in addition to structural units formed from the divalent aromatic groups mentioned above, include structural units represented by the following formulas (6a) to (6w). By including this type of structural unit, the hole injection properties of the aromatic compound having the structural unit represented by formula (1) can be further improved.

[Chemical Formula 20]

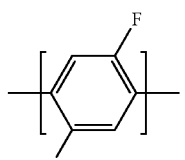
(6a)

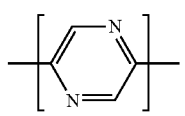
(6b)

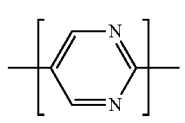
(6c)

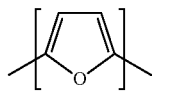
(6d)

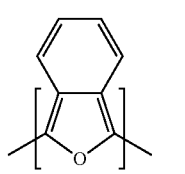
(6e)

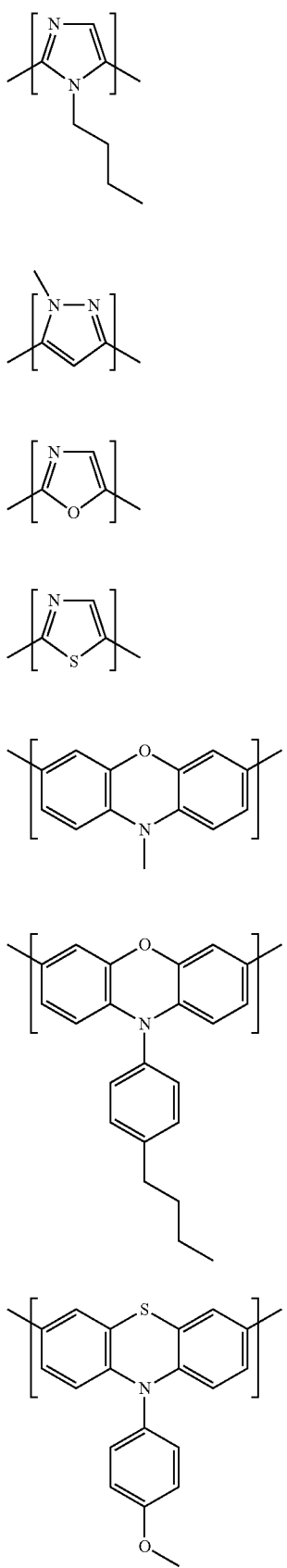
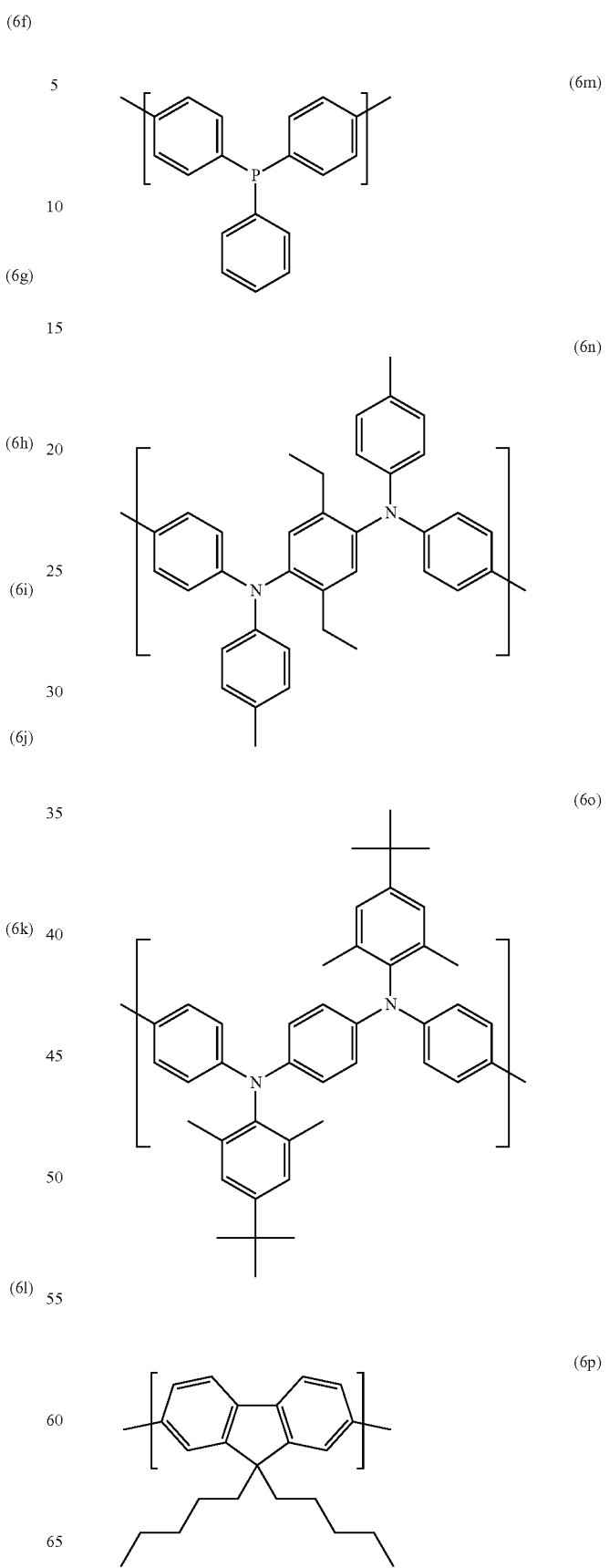

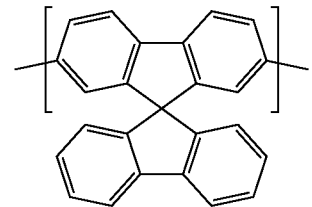 (6q)
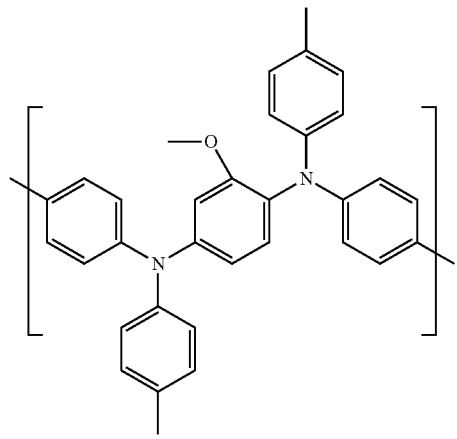 (6r)
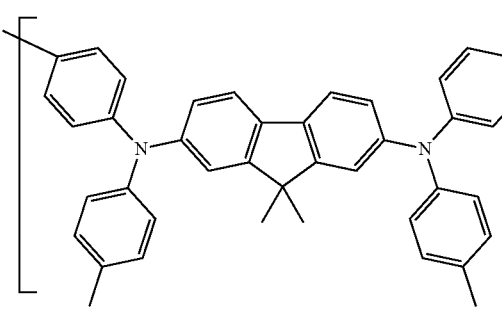 (6s)
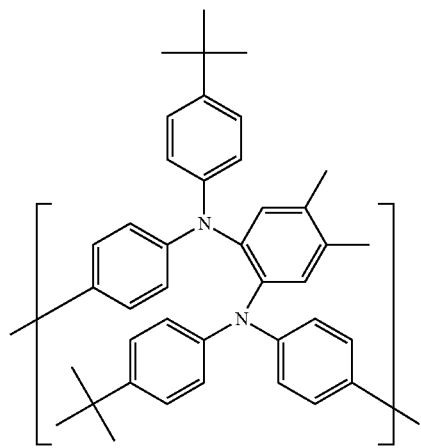 (6t)
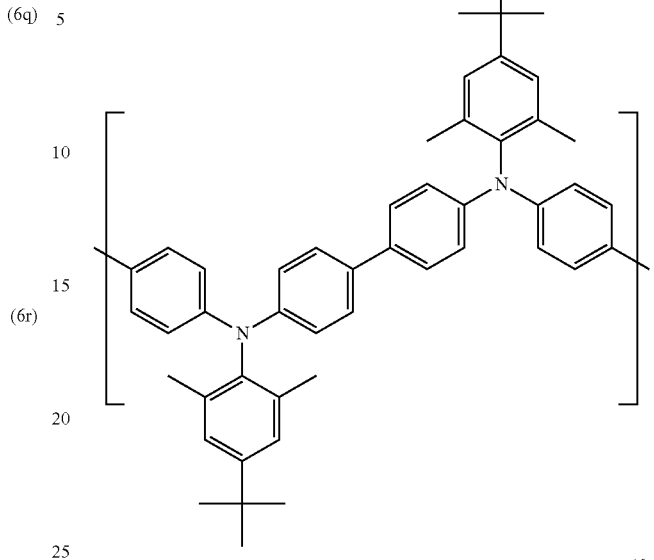 (6u)
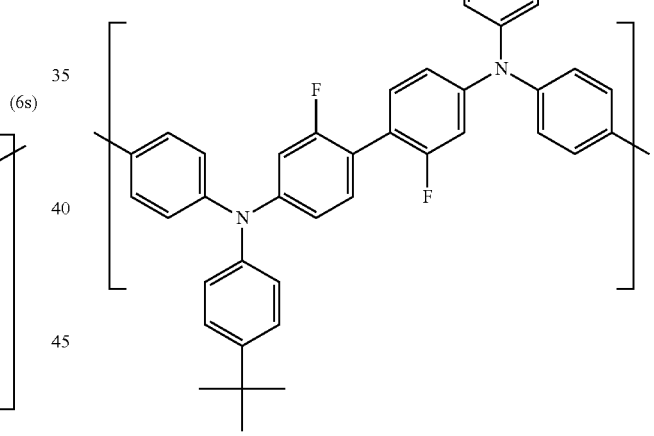 (6v)
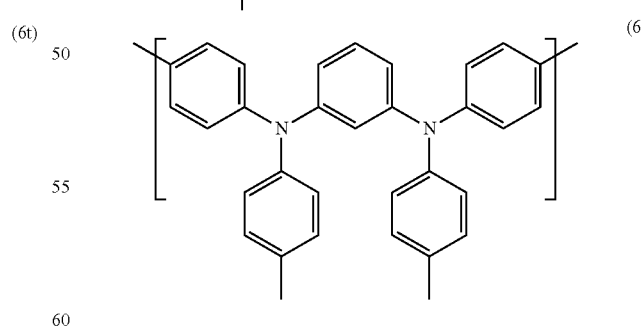 (6w)
Among these, (6a), (6b), (6c), (6f), (6n), (6o), (6t), (6u), (6v) and (6w) are preferable, and (6a), (6b), (6c), (6o) and (6t) are more preferable.
Examples of three preferred applications of the aromatic compounds used in the present invention to the hole injection material and/or hole transport material include [1] an application to the material used only for a hole injection layer, [2] an application to the material used for both a hole injection layer and a hole transport layer, and [3] an application to the material used only for a hole transport layer.

Of these, an application to the material used for both a hole injection layer and a hole transport layer is preferable, as it enables smooth hole transport from the positive electrode to the light emitting material. Further, ensuring that the hole injection layer and the hole transport layer have the same composition, and are formed simultaneously from a single material, is preferable in terms of minimizing the resistance at the interface between the hole injection layer and the hole transport layer, and in terms of lightening the process load by reducing the number of applied layers by one.

Another application of the aromatic compounds to the hole injection material and/or hole transport material is an application to the material used for a layer having a function of blocking electrons injected from the cathode.

<Layered Structure>

Next is a description of the layered structure of the present invention. The layered structure of the present invention has a substrate, and a hole injection and/or hole transport layer comprising an aromatic compound having a structural unit represented by formula (1). Examples of the substrate include the substrates mentioned later.

<Electronic Device>

Electronic devices that use the layered structure of the present invention are described below. Examples of these electronic devices include an organic transistor, a photoelectric conversion device such as a solar cell, and an electroluminescent device.

<Organic Transistor>

The aforementioned organic transistor has a source electrode, a drain electrode and an insulated gate electrode layer. This organic transistor may further have a substrate and at least one organic layer. At least one organic layer is a hole injection and/or hole transport layer comprising an aromatic compound having a structural unit represented by formula (1). In such cases, the layered structure of the present invention can be used.

<Photoelectric Conversion Device>

The aforementioned photoelectric conversion device has anode and cathode electrodes, and at least one organic layer provided between the electrodes, wherein at least one of the organic layers is a charge separation layer, and at least one of the organic layers is a hole injection and/or hole transport layer comprising an aromatic compound having a structural unit represented by formula (1). This photoelectric conversion device may further have a substrate, a hole injection layer, an electron injection layer, a hole transport layer or an electron transport layer or the like. In such cases, the layered structure of the present invention can be used.

<Electroluminescent Device>

An electroluminescent device that uses the layered structure of the present invention has, for example, a cathode, an anode, a light emitting layer positioned between the cathode and the anode, and a hole injection and/or hole transport layer comprising an aromatic compound having a structural unit represented by formula (1), which is positioned between the light emitting layer and the anode. The electroluminescent device of the present invention can have a substrate, and can have a structure in which the cathode, the anode, the hole injection and/or hole transport layer comprising an aromatic compound having a structural unit represented by formula (1), and other arbitrary structural elements are provided on the surface of the substrate.

In one aspect of an electroluminescent device that uses the layered structure of the present invention, an anode is provided on a substrate, a hole injection and/or hole transport layer comprising an aromatic compound having a structural unit represented by formula (1) is stacked on top of the anode, a light emitting layer is stacked thereon, and a cathode is then stacked on top.

In another aspect,
an anode is provided on a substrate,
a hole injection and/or hole transport layer comprising an aromatic compound having a structural unit represented by formula (1) is stacked on top of the anode,
a light emitting layer is stacked thereon,
another hole injection and/or hole transport layer comprising an aromatic compound having a structural unit represented by formula (1) is stacked on the light emitting layer, and a cathode is then stacked on top.

In yet another aspect,
a cathode is provided on a substrate,
a hole injection and/or hole transport layer comprising an aromatic compound having a structural unit represented by formula (1) is stacked on top of the cathode,
a light emitting layer is stacked thereon, and
an anode is then stacked on top.

In yet another aspect,
a cathode is provided on a substrate,
a light emitting layer is stacked thereon,
a hole injection and/or hole transport layer comprising an aromatic compound having a structural unit represented by formula (1) is stacked on top of the light emitting layer, and an anode is then stacked on top.

In yet another aspect,
a cathode is provided on a substrate,
a hole injection and/or hole transport layer comprising an aromatic compound having a structural unit represented by formula (1) is stacked on top of the cathode,
a light emitting layer is stacked thereon,
another hole injection and/or hole transport layer comprising an aromatic compound having a structural unit represented by formula (1) is stacked on the light emitting layer, and
an anode is then stacked on top.

Furthermore, in these aspects, layers having other functions such as a protective layer, a buffer layer or a reflective layer may also be provided.

The structure of an electroluminescent device that uses the layered structure of the present invention is described below in more detail.

The electroluminescent device is further covered with a sealing film or a sealing substrate, thus forming a light emitting device in which the electroluminescent device is isolated from the external atmosphere.

The hole injection and/or hole transport layer comprising an aromatic compound having a structural unit represented by formula (1) may be mixed with a conventional polymeric or low-molecular weight charge transport material, a conductive carbon such as graphene, fullerene or carbon nanotubes, a metal, an alloy, an electrically conductive compound such as a metal oxide or metal sulfide, or a mixture thereof. The material used in the hole transport layer or electron transport layer described below may be used as the charge transport material, and the materials used for the anode and cathode described below may be used as the metal, alloy, metal oxide or metal sulfide. Moreover, an organic material that has no light emitting or charge transport function, or an inorganic material such as a metal salt like a metal halide, metal hydroxide, metal carbonate, or a mixture thereof may also be included in the mixture, provided their inclusion does not impair the light emitting function of the light emitting device. The metal salt is preferably a metal salt of a metal having a work function of not more than 3.5 eV, and is more preferably a metal salt of an alkali metal or an alkaline earth metal.

The electroluminescent device used in the layered structure of the present invention may be any one of a so-called bottom emission type electroluminescent device that emits light from the substrate side of the device, a so-called top emission type electroluminescent device that emits light from the opposite side from the substrate, and a double-sided emission type electroluminescent device.

An example of a method for forming the hole injection and/or hole transport layer comprising an aromatic compound having a structural unit represented by formula (1) is a method in which film formation is performed using a solution containing the aromatic compound having a structural unit represented by formula (1).

The solvent used in the film formation using this type of solution is preferably a solvent excluding water, selected from among alcohols, ethers, esters, nitrile compounds, nitro compounds, alkyl halides, aryl halides, thiols, sulfides, sulfoxides, thioketones, amides and carboxylic acids and the like, which has a solubility parameter of not less than 9.3. Examples of the solvent (wherein the value inside the parentheses represents the solubility parameter value for each solvent, cited from the a value in Table 2.17 disclosed on page 39 of "Solvent Handbook (Kodansha Scientific, 1976)") include methanol (12.9), ethanol (11.2), 2-propanol (11.5), 1-butanol (10.7), tert-butyl alcohol (10.5), acetonitrile (11.8), 1,2-ethanediol (14.7), N,N-dimethylformamide (11.5), dimethylsulfoxide (12.8), acetic acid (12.4), nitrobenzene (11.1), nitromethane (11.0), 1,2-dichloroethane (9.7), dichloromethane (9.6), chlorobenzene (9.6), bromobenzene (9.9), dioxane (9.8), propylene carbonate (13.3), pyridine (10.4), carbon disulfide (10.0), and mixed solvents of these solvents. In the case of a mixed solvent prepared by mixing two solvents (termed solvent 1 and solvent 2), the solubility parameter ($\delta m$) of the mixed solvent is determined by the equation: $\delta m = \delta 1 \times \phi 1 + \delta 2 \times \phi 2$ (wherein $\delta 1$ denotes the solubility parameter of the solvent 1, $\phi 1$ denotes the volume fraction of the solvent 1, $\delta 2$ denotes the solubility parameter of the solvent 2, and $\phi 2$ denotes the volume fraction of the solvent 2).

Among these solvents, from the viewpoints of safety and accident prevention, a solvent having a high flash point is preferably used.

Further, in those cases where a solubility parameter value for the solvent used in the film formation is not reported in the above publication, the value can also be calculated using the following calculation. Namely, by using the literature value for the density, and creating a model composed of 180 solvent molecules in accordance with the density, the solubility parameter can be calculated in the NVT ensemble by a molecular dynamics method using a force field compass. Having allowed sufficient time for the energy to reach an equilibrium state, sampling is performed, and the cohesive energy density of the system is calculated (as a statistic). The solubility parameter can be determined as the square root of the cohesive energy density.

The following solvents, for which the solubility parameter was determined using the above method, can also be used favorably. Ethylene glycol (14.6), N,N-dimethylacetamide (11.1) and N-methylpyrrolidinone (11.5).

The units for these solubility parameter values are $(cal/cm^3)^{1/2}$.

Examples of methods that can be used as the method for forming a film using a solution include coating methods such as a spin coating method, casting method, bar coating method, roll coating method, wire bar coating method, dip coating method, slit coating method, capillary coating method, spray coating method and nozzle coating method, and printing methods such as a micro gravure printing method, gravure printing method, screen printing method, flexographic printing method, offset printing method, inversion printing method and inkjet printing method. In terms of enabling easier pattern formation, printing methods such as a gravure printing method, screen printing method, flexographic printing method, offset printing method, inversion printing method and inkjet printing method, and a nozzle coating method are preferable.

The optimum value for the thickness of the hole injection and/or hole transport layer comprising the aromatic compound having a structural unit represented by formula (1) varies depending on the material used, and therefore the thickness may be selected so that the drive voltage and the luminous efficiency adopt appropriate values, but a thickness that also prevents the generation of pinholes is required. From the viewpoint of reducing the drive voltage of the device, the thickness is preferably from 1 nm to 1 μm, more preferably from 2 nm to 500 nm, and still more preferably from 2 nm to 200 nm. From the viewpoint of protecting the light emitting layer, the thickness is preferably from 5 nm to 1 μm.

The electroluminescent device that uses the layered structure of the present invention has a cathode and an anode, and has a light emitting layer disposed between the cathode and the anode, but may also include other structural elements.

For example, the device may include a hole injection and/or hole transport layer comprising an aromatic compound having a structural unit represented by formula (1) between the anode and the light emitting layer. In this case, the first electrode becomes the anode, and the second electrode becomes the cathode.

Here, the anode is the electrode that supplies holes to the hole injection and/or hole transport layer comprising the aromatic compound having a structural unit represented by formula (1), and the cathode is the electrode that supplies electrons to the electron injection layer, electron transport layer or light emitting layer or the like.

The light emitting layer describes a layer having a function of accepting holes from a layer adjacent to the anode side and accepting electrons from a layer adjacent to the cathode side when an electric field is applied, a function of moving accepted charges (electrons and holes) using the force of the electric field, and a function of providing a field for the recombination of electrons and holes, thus leading to light emission.

The electron injection layer and electron transport layer describe layers having any of a function of accepting electrons from the cathode, a function of transporting electrons, a function of blocking holes injected from the anode, and a function of supplying electrons to the light emitting layer.

The hole injection layer and hole transport layer describe layers having any of a function of accepting holes from the anode, a function of transporting holes, a function of supplying holes to the light emitting layer, and a function of blocking electrons injected from the cathode.

The electron transport layer and the hole transport layer are sometimes collectively referred to as charge transport layers. Further, the electron injection layer and the hole injection layer are sometimes collectively referred to as charge injection layers.

In other words, an electroluminescent device using the layered structure of the present invention can have the following layer configuration (a), or can also have a layer configuration in which one or more layers of the hole injection layer, the hole transport layer, the electron transport layer and the electron injection layer have been omitted from the layer configuration (a). In the layer configuration (a), a layer comprising the aromatic compound of the present invention can be used as one or more layers selected from the group consisting of the hole injection layer, the hole transport layer, the electron injection layer and the electron transport layer.

(a) Anode-Hole Injection Layer-(Hole Transport Layer)-Light Emitting Layer-(Electron Transport Layer)-Electron Injection Layer-Cathode Here, the symbol "-" indicates that the respective layers are layered adjacently. "(Hole transport layer)" indicates a layer composed of only a hole transport layer. "(Electron transport layer)" indicates a layer composed of only an electron transport layer. These definitions also apply in the descriptions of the following layer configurations.

Moreover, the electroluminescent device using the layered structure of the present invention can have a two-layered light emitting layer in one layered structure. In this case, the electroluminescent device can have the following layer configuration (b), or can also have a layer configuration in which one or more layers of the hole injection layer, the hole transport layer, the electron transport layer, the electron injection layer and the electrode have been omitted from the layer configuration (b). In the layer configuration (b), a hole injection layer and/or hole transport layer comprising an aromatic compound having a structural unit represented by formula (1) can be used as a layer that exists between the anode and the light emitting layer closest to the anode, or as a layer that exists between the cathode and the light emitting layer closest to the cathode.

(b) Anode-Hole Injection Layer-(Hole Transport Layer)-Light Emitting Layer-(Electron Transport Layer)-Electron Injection Layer-Electrode-Hole Injection Layer-(Hole Transport Layer)-Light-Emitting Layer-(Electron Transport Layer)-Electron Injection Layer-Cathode Moreover, the electroluminescent device using the layered structure of the present invention can have a multi-layered light emitting layer of three or more layers in one layered structure. In this case, the electroluminescent device can have the following layer configuration (c), or can also have a layer configuration in which one or more layers of the hole injection layer, the hole transport layer, the electron transport layer, the electron injection layer and the electrode have been omitted from the layer configuration (c). In the layer configuration (c), a layer comprising the aromatic compound of the present invention can be used as a layer that exists between the anode and the light emitting layer closest to the anode, or as a layer that exists between the cathode and the light emitting layer closest to the cathode.

(c) Anode-Hole Injection Layer-(Hole Transport Layer)-Light Emitting Layer-(Electron Transport Layer)-Electron Injection Layer-Unit Q-Unit Q- . . . -Cathode The "unit Q" indicates a layer configuration composed of: electrode-hole injection layer-(hole transport layer)-light-emitting layer-(electron transport layer)-electron injection layer.

In the present invention, examples of the electroluminescent device provided with a charge injection layer (electron injection layer or hole injection layer) include electroluminescent devices in which the charge injection layer is provided adjacent to the cathode, and electroluminescent devices in which the charge injection layer is provided adjacent to the anode. Examples of the layer configurations for these electroluminescent devices include the following configurations (d) to (m).

(d) Anode-charge injection layer-light emitting layer-cathode (e) Anode-charge injection layer-light emitting layer-charge injection layer-cathode (f) Anode-charge injection layer-hole transport layer-light emitting layer-cathode (g) Anode-hole transport layer-light emitting layer-charge injection layer-cathode (h) Anode-charge injection layer-hole transport layer-light emitting layer-charge injection layer-cathode (i) Anode-charge injection layer-light emitting layer-electron transport layer-cathode (j) Anode-charge injection layer-light emitting layer-electron transport layer-charge injection layer-cathode (k) Anode-charge injection layer-hole transport layer-light emitting layer-electron transport layer-cathode (l) Anode-hole transport layer-light emitting layer-electron transport layer-charge injection layer-cathode (m) Anode-charge injection layer-hole transport layer-light emitting layer-electron transport layer-charge injection layer-cathode In the aforementioned electroluminescent devices, an insulation layer may further be provided adjacent to the electrode to improve the adhesion to the electrode and improve the injection of charge (namely, holes or electrons) from the electrode, and a thin buffer layer may be inserted at the interface of a charge transport layer (namely, a hole transport layer or electron transport layer) or a light emitting layer to improve the adhesion at the interface and prevent mixing. The order in which the layers are layered, the number of layers, and the thickness of each layer can be determined with due consideration of the luminous efficiency and the device lifespan.

Next is a more detailed description of the materials and formation methods used for each layer that constitutes the electroluminescent device using the layered structure of the present invention.

—Substrate—

The substrate of the aforementioned electroluminescent device may be any substrate that does not chemically change when an electrode is formed and an organic layer is formed. For example, glasses, plastics, polymer films, metal films, silicon substrates, and layered substrates thereof can be used. These types of substrates are commercially available, or can be produced using a known method.

When the electroluminescent device of the present invention constitutes a pixel of a display device, a circuit for driving the pixel may be provided on the substrate, and a smoothing film may be provided on the drive circuit. When a smoothing film is provided, the center line average roughness (Ra) of the smoothing film preferably satisfies Ra<10 nm.

Ra can be measured based on Japanese Industrial Standard (JIS) JIS-B0601-2001, with reference to JIS-B0651 to JIS-B0656 and JIS-B0671-1 and the like.

—Anode—

For the anode of the aforementioned electroluminescent device, from the viewpoint of the hole supply properties to the organic semiconductor material used for the hole injection layer, hole transport layer and light emitting layer and the like, the work function of the surface of the anode on the side of the light emitting layer is preferably not less than 4.0 eV.

Electrically conductive compounds such as metals, alloys, metal oxides and metal sulfides, and mixtures thereof can be used as the material for the anode. Specific examples include conductive metal oxides such as tin oxide, zinc oxide, indium oxide, indium tin oxide (ITO), indium zinc oxide (IZO) and molybdenum oxide, metals such as gold, silver, chromium and nickel, and mixtures of these conductive metal oxides and metals.

The anode may have a single layered structure composed of one, or two or more, of these materials, or a multi-layered structure composed of a plurality of layers having the same composition or different compositions. In the case of a multi-layered structure, it is preferable that a material having a work function of not less than 4.0 eV is used for the outermost surface layer on the side of the light emitting layer.

The method for producing the anode can use a known method, and examples include a vacuum deposition method, sputtering method, ion plating method, plating method, and a method that employs film formation using a solution (which may use a mixed solution with a polymeric binder).

The thickness of the anode is typically from 10 nm to 10 μm, and is preferably from 50 nm to 500 nm. Further, from the viewpoint of preventing electrical connection faults such as short circuits, the center line average roughness (Ra) of the surface of the anode on the side of the light emitting layer preferably satisfies Ra<10 nm, and more preferably satisfies Ra<5 nm.

Moreover, following production using a method described above, the anode may sometimes be subjected to a surface treatment with a solution or the like containing UV ozone, a silane coupling agent, or an electron-accepting compound such as 2,3,5,6-tetrafluoro-7,7,8,8-tetracyanoquinodimethane. This surface treatment improves the electrical connection with the layer contacting the anode.

When the anode is used as a light reflective electrode in the aforementioned electroluminescent device, the anode preferably has a multi-layered structure in which a light reflective layer formed from a highly reflective metal is combined with a high work function material layer containing a material having a work function of not less than 4.0 eV.

Specific examples of the configuration of this type of anode include the following.

(i) Ag—$MoO_3$
(ii) (Ag—Pd—Cu alloy)-(ITO and/or IZO)
(iii) (Al—Nd alloy)-(ITO and/or IZO)
(iv) (Mo—Cr alloy)-(ITO and/or IZO)
(v) (Ag—Pd—Cu alloy)-(ITO and/or IZO)-$MoO_3$ In order to obtain sufficient light reflectance, the thickness of the highly reflective metal layer formed from Al, Ag, Al alloy, Ag alloy, or Cr alloy or the like is preferably not less than 50 nm, and more preferably not less than 80 nm. The thickness of the high work function material layer formed from ITO, IZO or $MoO_3$ is typically within a range from 5 nm to 500 nm.

—Hole Injection Layer—

In the electroluminescent device using the layered structure of the present invention, examples of materials that can be used favorably as the material that forms the hole injection layer, other than the aromatic compound having a structural unit represented by formula (1), include carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, starburst type amines, phthalocyanine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, organic silane derivatives, and polymers containing one or more of the above;

conductive metal oxides such as vanadium oxide, tantalum oxide, tungsten oxide, molybdenum oxide, ruthenium oxide and aluminum oxide;

conductive polymers and oligomers such as polyaniline, aniline-based copolymers, thiophene oligomers and polythiophene;

organic conductive materials such as poly(3,4-ethylenedioxythiophene)-polystyrenesulfonic acid, polypyrrole, and polymers thereof;

amorphous carbon;

acceptor organic compounds such as tetracyanoquinodimethane derivatives (for example, 2,3,5,6-tetrafluoro-7,7,8,8-tetracyanoquinodimethane), 1,4-naphthoquinone derivatives, diphenoquinone derivatives and polynitro compounds; and silane coupling agents such as octadecyltrimethoxysilane.

The above materials may be used in the form of a single component, or a composition composed of a plurality of components. Further, the hole injection layer may be a single layered structure composed of only the above materials, or a multi-layered structure composed of a plurality of layers having the same composition or different compositions. Furthermore, the materials listed as materials that can be used in the hole transport layer can also be used in the hole injection layer.

Examples of the method for forming the hole injection layer include the following methods. Namely, examples of film formation methods using a solution include coating methods and printing methods such as a spin coating method, casting method, bar coating method, slit coating method, spray coating method, nozzle coating method, gravure printing method, screen printing method, flexographic printing method and inkjet printing method, and in those cases where a sublimable compound material is used, examples of the method include a vacuum deposition method and a transfer method. Examples of the solvent used when performing film formation using a solution include the solvents listed above within the description of the method for forming a film using a solution containing an aromatic compound having a structural unit represented by formula (1).

When organic compound layers such as a hole transport layer and a light emitting layer are formed following formation of the hole injection layer, and particularly in those cases when both layers are formed by a coating method, the previously applied layer may sometimes dissolve in the solvent contained in the solution used for forming the subsequently applied layer, making it impossible to produce a layered structure. In these cases, a method of making the lower layer insoluble in the solvent can be used. Examples of this method of making the lower layer insoluble in the solvent include a method in which a crosslinking group is introduced into a polymer compound, and crosslinking is performed to make the layer insoluble, a method in which a low molecular weight compound having a crosslinking group with an aromatic ring, typified by an aromatic bisazide, is mixed as a crosslinking agent, and crosslinking is performed to make the layer insoluble, a method in which a low molecular weight compound having a crosslinking group with no aromatic ring, typified by an acrylate group, is mixed as a crosslinking agent, and crosslinking is performed to make the layer insoluble, a method in which the lower layer is subjected to crosslinking through exposure to ultraviolet light, thereby making the lower layer insoluble in the organic solvent used to produce the upper layer, and a method in which the lower layer is subjected to crosslinking by heating, thereby making the lower layer insoluble in the organic solvent used to produce the upper layer. When the lower layer is heated, the heating temperature is typically from 100° C. to 300° C., and the heating time is typically from one minute to one hour.

Further, one example of another method of performing layering without dissolving the lower layer that does not rely on crosslinking is a method in which different polarity solutions are used for producing adjacent layers, for example, a method in which a water-soluble polymer compound is used for the lower layer, and an oil-soluble polymer compound is used for the upper layer, meaning the lower layer does not dissolve even upon application of the upper layer.

The optimum value for the thickness of the hole injection layer varies depending on the material used, and therefore the thickness may be selected so that the drive voltage and the luminous efficiency adopt appropriate values, but a thickness that also prevents the generation of pinholes is required, and if the layer is too thick, then the drive voltage of the device increases undesirably. Accordingly, the thickness of the hole injection layer is typically from 1 nm to 1 µm, preferably from 2 nm to 500 nm, and more preferably from 10 nm to 100 nm.

—Hole Transport Layer—

In the electroluminescent device of the present invention, examples of materials that can be used for forming the hole transport layer, other than the aromatic compound having a structural unit represented by formula (1), include carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, organic silane derivatives, and polymers containing one or more of these structures; conductive polymers and oligomers such as aniline-based copolymers, thiophene oligomers and polythiophene; and organic conductive materials such as polypyrrole.

The above materials may be used in the form of a single component, or a composition composed of a plurality of components. Further, the hole transport layer may be a single layered structure composed of only the above materials, or a multi-layered structure composed of a plurality of layers having the same composition or different compositions. Furthermore, the materials listed as materials that can be used in the hole injection layer can also be used in the hole transport layer.

Other materials that are useful as the material that constitutes the hole transport layer include compounds disclosed in JP 63-70257 A, JP 63-175860 A, JP 02-135359 A, JP 02-135361 A, JP 02-209988 A, JP 03-37992 A, JP 03-152184 A, JP 05-263073 A, JP 06-1972 A, WO 2005/52027 and JP 2006-295203 A, and among these compounds, polymers containing a divalent aromatic amine residue as a repeating unit can be used particularly favorably.

Examples of the method for forming the hole transport layer include the same methods as those mentioned for forming the hole injection layer. Examples of the solvent used when performing film formation using a solution include the solvents mentioned above within the description of the method for forming the hole injection layer.

When an organic layer such as a light emitting layer is formed by a coating method following formation of the hole transport layer, in those cases where the lower layer dissolves in the solvent contained in the solution used for forming the subsequently applied layer, the lower layer can be made insoluble in the solvent using the same methods as those mentioned in the method for forming the hole injection layer.

The optimum value for the thickness of the hole transport layer varies depending on the material used, and therefore the thickness may be selected so that the drive voltage and the luminous efficiency adopt appropriate values, but a thickness that also prevents the generation of pinholes is required, and if the layer is too thick, then the drive voltage of the device increases undesirably. Accordingly, the thickness of the hole transport layer is typically from 1 nm to 1 µm, preferably from 2 nm to 500 nm, and more preferably from 5 nm to 100 nm.

—Light Emitting Layer—

In the aforementioned electroluminescent device, when the light emitting layer contains a polymer compound, conjugated polymer compounds such as polyfluorene derivatives, poly(paraphenylene vinylene) derivatives, polyphenylene derivatives, polyparaphenylene derivative, polythiophene derivatives, polydialkylfluorenes, polyfluorenebenzothiadiazole and polyalkylthiophenes can be used favorably as the polymer compound.

Further, the light emitting layer containing the above polymer compound may also contain polymeric pigment compounds such as perylene-based pigments, coumarin-based pigments and rhodamine-based pigments, and low molecular weight pigment compounds such as rubrene, perylene, 9,10-diphenylanthracene, tetraphenylbutadiene, nile red, coumarin 6 or quinacridone. Furthermore, the light emitting layer may also contain naphthalene derivatives, anthracene and derivatives thereof, perylene and derivatives thereof, polymethine-based, xanthene-based, coumarin-based and cyanine-based pigments, metal complexes of 8-hydroxyquinoline and derivatives thereof, aromatic amines, tetraphenylcyclopentadiene and derivatives thereof, tetraphenylbutadiene and derivatives thereof, and metal complexes that emit phosphorescence, such as tris(2-phenylpyridine)iridium.

Further, the light emitting layer of the aforementioned electroluminescent device may be formed from a composition of a non-conjugated polymer compound, and a light emitting organic compound such as the aforementioned organic pigments or metal complexes. Examples of the non-conjugated polymer compound include polyethylene, polyvinyl chloride, polycarbonate, polystyrene, poly(methyl methacrylate), poly(butyl methacrylate), polyester, polysulfone, poly(phenylene oxide), polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin and silicon resin. The above non-conjugated polymer compound may have, on a side chain, a structure composed of one or more derivatives or compounds selected from the group consisting of carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin compounds and organic silane derivatives.

When the light emitting layer contains a low molecular weight compound, examples of the low molecular weight compound include low molecular weight pigment compounds such as rubrene, perylene, 9,10-diphenylanthracene, tetraphenylbutadiene, nile red, coumarin 6, carbazole and quinacridone, naphthalene derivatives, anthracene and derivatives thereof, perylene and derivatives thereof, polymethine-based, xanthene-based, coumarin-based, cyanine-based and indigo-based pigments, metal complexes of 8-hydroxyquinoline and derivatives thereof, metal complexes of phthalocyanine and derivatives thereof, aromatic amines, tetraphenylcyclopentadiene and derivatives thereof, and tetraphenylbutadiene and derivatives thereof.

When the light emitting layer contains a metal complex capable that emits phosphorescence, examples of the metal complex include tris(2-phenylpyridine)iridium, iridium complexes containing a thienylpyridine ligand, iridium complexes containing a phenylquinoline ligand and terbium complexes containing a triazacyclononane structure.

Examples of polymer compounds that can be used in the light emitting layer include polyfluorenes disclosed in WO 97/09394, WO 98/27136, WO 99/54385, WO 00/22027, WO 01/19834, GB 2340304 A, GB 2348316, U.S. Pat. No. 5,741, 921, U.S. Pat. No. 5,777,070, EP 0707020, JP 09-111233 A, JP 10-324870 A, JP 2000-80167 A, JP 2001-123156 A, JP 2004-168999 A, JP 2007-162009 and "Development of Organic EL Device & Their Materials" (CMC Publishing Co., Ltd., published 2006), derivatives and copolymers of such polyfluorenes, polyarylenes and derivatives and copolymers thereof, polyarylenevinylenes and derivatives and copolymers thereof, and (co)polymers of aromatic amines and derivatives thereof.

Further, examples of the low molecular weight compounds include compounds disclosed in JP 57-51781 A, "Data book on work function of organic thin films [2nd edition]" (CMC Publishing Co., Ltd., published 2006), and "Development of Organic EL Device & Their Materials" (CMC Publishing Co., Ltd., published 2006).

The material may be a single component, or a composition composed of a plurality of components. Further, the light emitting layer may have a single layered structure composed of one, or two or more, of the above materials, or a multi-layered structure composed of a plurality of layers having the same composition or different compositions.

Examples of the method for forming the light emitting layer include the same methods as those described for forming the hole injection layer. Examples of the solvent used when performing film formation using a solution include the solvents mentioned above within the description of the method for forming the hole injection layer.

When an organic compound layer such as an electron transport layer is formed by a coating method following formation of the light emitting layer, in those cases where the lower layer dissolves in the solvent contained in the solution used for forming the subsequently applied layer, the lower layer can be made insoluble in the solvent using the same methods as those mentioned in the method for forming the hole injection layer.

The optimum value for the thickness of the light emitting layer varies depending on the material used, and therefore the thickness may be selected so that the drive voltage and the luminous efficiency adopt appropriate values, but a thickness that also prevents the generation of pinholes is required, and if the layer is too thick, then the drive voltage of the device increases undesirably. Accordingly, the thickness of the light emitting layer is typically from 5 nm to 1 m, preferably from 10 nm to 500 nm, and more preferably from 30 nm to 200 nm.

—Electron Transport Layer—

In the aforementioned electroluminescent device, examples of materials that can be used for forming the electron transport layer and hole blocking layer, other than the aromatic compound having a structural unit represented by formula (1), include known materials, and specific examples include triazole derivatives, oxazole derivatives, oxadiazole derivatives, imidazole derivatives, fluorene derivatives, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, anthrone derivatives, thiopyran dioxide derivatives, carbodiimide derivatives, fluorenylidenemethane derivatives, distyrylpyrazine derivatives, aromatic cyclic tetracarboxylic anhydrides of naphthalene and perylene and the like, phthalocyanine derivatives, various metal complexes typified by metal complexes of 8-quinolinol derivatives, metal phthalocyanines, and metal complexes containing benzoxazole or benzothiazole as a ligand, organic silane derivatives, metal complexes of 8-hydroxyquinoline and derivatives thereof, polyquinoline and derivatives thereof, polyquinoxaline and derivatives thereof, and polyfluorene and derivatives thereof. Among these materials, triazole derivatives, oxadiazole derivatives, benzoquinone and derivatives thereof, anthraquinone and derivatives thereof, metal complexes of 8-hydroxyquinoline and derivatives thereof, polyquinoline and derivatives thereof, polyquinoxaline and derivatives thereof and polyfluorene and derivatives thereof are preferred.

The material may be a single component, or a composition composed of a plurality of components. Further, the electron transport layer may have a single layered structure composed of one, or two or more, of the above materials, or a multi-layered structure composed of a plurality of layers having the same composition or different compositions. Furthermore, the materials listed as materials that can be used in the electron injection layer can also be used in the electron transport layer.

Examples of the method for forming the electron transport layer include the same methods as those described for forming the hole injection layer. Examples of the solvent used when performing film formation using a solution include the solvents mentioned above within the description of the method for forming the hole injection layer.

When an organic compound layer such as an electron injection layer is formed by a coating method following formation of the electron transport layer, in those cases where the lower layer dissolves in the solvent contained in the solution used for forming the subsequently applied layer, the lower layer can be made insoluble in the solvent using the same methods as those mentioned in the method for forming the hole injection layer.

The optimum value for the thickness of the electron transport layer varies depending on the material used, and therefore the thickness may be selected so that the drive voltage and the luminous efficiency adopt appropriate values, but a thickness that also prevents the generation of pinholes is required, and if the layer is too thick, then the drive voltage of the device increases undesirably. Accordingly, the thickness of the electron transport layer is typically from 1 nm to 1 µm, preferably from 2 nm to 500 nm, and more preferably from 5 nm to 100 nm.

—Electron Injection Layer—

In the aforementioned electroluminescent device, known compounds can be used as the material for forming the electron injection layer, and examples include triazole derivatives, oxazole derivatives, oxadiazole derivatives, imidazole derivatives, fluorene derivatives, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, anthrone derivatives, thiopyran dioxide derivatives, carbodiimide derivatives, fluorenylidenemethane derivatives, distyrylpyrazine derivatives, aromatic cyclic tetracarboxylic anhydrides of naphthalene and perylene and the like, phthalocyanine derivatives, various metal complexes typified by metal complexes of 8-quinolinol derivatives, metal phthalocyanines, and metal complexes containing benzoxazole or benzothiazole as a ligand, and organic silane derivatives.

The material may be a single component, or a composition composed of a plurality of components. Further, the electron injection layer may have a single layered structure composed of only the above materials, or a multi-layered structure composed of a plurality of layers having the same composition or different compositions. Furthermore, the materials listed as materials that can be used in the electron transport layer can also be used in the electron injection layer.

Examples of the method for forming the electron injection layer include the same methods as those described for forming the hole injection layer. Examples of the solvent used when performing film formation using a solution include the solvents mentioned above within the description of the method for forming the hole injection layer.

The optimum value for the thickness of the electron injection layer varies depending on the material used, and therefore the thickness may be selected so that the drive voltage and the luminous efficiency adopt appropriate values, but a thickness that also prevents the generation of pinholes is required, and if the layer is too thick, then the drive voltage of the device increases undesirably. Accordingly, the thickness of the electron injection layer is typically from 1 nm to 1 μm, preferably from 2 nm to 500 nm, and more preferably from 5 nm to 100 nm.

—Cathode—

In the electroluminescent device of the present invention, the cathode may have a single layered structure composed of a single material or a plurality of materials, or a multi-layered structure composed of a plurality of layers. When the cathode has a single layered structure, examples of the material of the cathode include low-resistance metals such as gold, silver, copper, aluminum, chromium, tin, lead, nickel and titanium, alloys containing these metals, conductive metal oxides such as tin oxide, zinc oxide, indium oxide, indium tin oxide (ITO), indium zinc oxide (IZO) and molybdenum oxide, and mixtures of these conductive metal oxides and metals. In the case of a multi-layered structure, a two-layered structure composed of a first cathode layer and a cover cathode layer, or a three-layered structure composed of a first cathode layer, a second cathode layer and a cover cathode layer is preferable. The first cathode layer refers to the layer within the cathode that is closest to the light emitting layer side, and the cover cathode layer refers to a layer that covers the first cathode layer in the case of a two-layered structure, or covers the first cathode layer and the second cathode layer in the case of a three-layered structure. From the viewpoint of the electron supply function, the work function of the material of the first cathode layer is preferably not more than 3.5 eV. A metal oxide, fluoride, carbonate or complex oxide having a work function of not more than 3.5 eV can also be used favorably as the first cathode layer material. For the material for the cover cathode layer, a metal or metal oxide or the like that has low resistivity and superior corrosion resistance to moisture can be used favorably.

Examples of the first cathode layer material include one or more materials selected from the group consisting of alkali metals, alkaline earth metals, alloys containing one or more of the above metals, oxides, halides, carbonates and complex oxides of the above metals, and mixtures thereof. Examples of the alkali metals and the oxides, halides, carbonates and complex oxides thereof include lithium, sodium, potassium, rubidium, cesium, lithium oxide, sodium oxide, potassium oxide, rubidium oxide, cesium oxide, lithium fluoride, sodium fluoride, potassium fluoride, rubidium fluoride, cesium fluoride, lithium carbonate, sodium carbonate, potassium carbonate, rubidium carbonate, cesium carbonate, potassium molybdate, potassium titanate, potassium tungstate and cesium molybdate. Examples of the alkaline earth metals and the oxides, halides, carbonates and complex oxides thereof include magnesium, calcium, strontium, barium, magnesium oxide, calcium oxide, strontium oxide, barium oxide, magnesium fluoride, calcium fluoride, strontium fluoride, barium fluoride, magnesium carbonate, calcium carbonate, strontium carbonate, barium carbonate, barium molybdate and barium tungstate. Examples of the alloys containing one or more of the alkali metals or alkaline earth metals include Li—Al alloys, Mg—Ag alloys, Al—Ba alloys, Mg—Ba alloys, Ba—Ag alloys and Ca—Bi—Pb—Sn alloys. A composition of a material mentioned above as the first cathode layer material and a material mentioned above as the material for forming the electron injection layer can also be used for the first cathode layer. Examples of the material for the second cathode layer include the same materials as those of the first cathode layer.

Examples of the material for the cover cathode layer include low-resistance metals such as gold, silver, copper, aluminum, chromium, tin, lead, nickel and titanium, alloys, metal nanoparticles and metal nanowires containing these metals, conductive metal oxides such as tin oxide, zinc oxide, indium oxide, indium tin oxide (ITO), indium zinc oxide (IZO) and molybdenum oxide, mixtures of these conductive metal oxides and metals, conductive metal oxide nanoparticles, and conductive carbon such as graphene, fullerene and carbon nanotubes.

Examples of the case where the cathode has a multi-layered structure include two-layered structures composed of the first cathode layer and the cover cathode layer, such as Mg/Al, Ca/Al, Ba/Al, NaF/Al, KF/Al, RbF/Al, CsF/Al, Na$_2$CO$_3$/Al, K$_2$CO$_3$/Al and Cs$_2$CO$_3$/Al, and three-layered structures composed of the first cathode layer, the second cathode layer and the cover cathode layer, such as LiF/Ca/Al, NaF/Ca/Al, KF/Ca/Al, RbF/Ca/Al, CsF/Ca/Al, Ba/Al/Ag, KF/Al/Ag, KF/Ca/Ag and K$_2$CO$_3$/Ca/Ag. In these examples, the symbol "/" means that the layers are adjacent.

The material of the second cathode layer preferably has a reactivity as a reductant acting on the material of the first cathode layer. Here, the existence or absence of the reduction between the materials, and the degree of the reactivity can be estimated, for example, from the bond dissociation energy ($\Delta rH°$) between the compounds. In other words, a material combination giving rise to a positive bond dissociation energy in the reduction reaction of the material of the first cathode layer by the material of the second cathode layer indicates that the material of the second cathode layer has a reactivity as a reductant acting on the material of the first cathode layer. Bond dissociation energies can be referred to, for example, in "Denki-Kagaku Binran (Electrochemical Handbook), 5th edition" (published by Maruzen Co., Ltd., 2000) and "Thermodynamic Database MALT" (published by Kagaku Gijutsu-Sha, 1992).

The method for producing the cathode can use a known method, and examples include a vacuum deposition method, sputtering method, ion plating method, and a method that employs film formation using a solution (which may use a mixed solution with a polymeric binder). When a metal or a metal oxide, fluoride or carbonate is used, a vacuum deposition method is frequently used, whereas when a metal oxide or metal complex oxide having a high boiling point, or a conductive metal oxide such as indium tin oxide (ITO) is used, a sputtering method or ion plating method is frequently used. When film formation is performed using a combination of two or more metals, metal oxides, fluorides or carbonates, high-boiling point metal oxides or metal complex oxides, and conductive metal oxides, a co-deposition method, sputtering method or ion plating method or the like can be used. In the case of metal nanoparticles, metal nanowires or conductive metal oxide nanoparticles, a method that employs film formation using a solution is often used. A co-deposition method is particularly suitable in those cases where film formation is performed using a composition of a low molecular weight organic compound, and a metal or a metal oxide, fluoride or carbonate.

The optimum value for the thickness of the cathode varies depending on the material used and the layer structure, and therefore the thickness may be selected so that the drive voltage, the luminous efficiency and the device lifespan adopt appropriate values, but typically, the thickness of the first cathode layer is from 0.5 nm to 20 nm, and the thickness of the cover cathode layer is from 10 nm to 1 μm. For example, when Ba or Ca is used for the first cathode layer and Al is used for the cover cathode layer, the thickness of Ba or Ca is preferably from 2 nm to 10 nm, and the thickness of Al is preferably from 10 nm to 500 nm, whereas when NaF or KF is used for the first cathode layer and Al is used for the cover cathode layer, the thickness of NaF or KF is preferably from 1 nm to 8 nm, and the thickness of Al is preferably from 10 nm to 500 nm.

When the cathode is used as a light transmitting electrode in the aforementioned electroluminescent device, the visible light transmittance of the cover cathode layer is preferably at least 40%, and more preferably 50% or greater. This visible light transmittance is achieved either by using a transparent conductive metal oxide such as indium tin oxide (ITO), indium zinc oxide (IZO) or molybdenum oxide as the cover cathode layer material, or by setting the thickness of the cover cathode layer that uses a low-resistance metal such as gold, silver, copper, aluminum, chromium, tin or lead, or an alloy containing these metals, to not more than 30 nm.

Further, an anti-reflective layer can also be provided on the cover cathode layer of the cathode for the purpose of improving the light transmittance from the cathode side. The material used in the anti-reflective layer preferably has a refractive index of 1.8 to 3.0, and examples of materials that satisfy this refractive index requirement include ZnS, ZnSe and $WO_3$. The thickness of the anti-reflective layer varies depending on the combination of materials, but is typically within a range from 10 nm to 150 nm.

—Insulation Layer—

An insulation layer having a thickness of not more than 5 nm, which can be optionally included in the aforementioned electroluminescent device, has the functions of improving adhesion to the electrodes, improving charge injection from the electrodes, and preventing mixing of with adjacent layers. Examples of the material of the insulation layer include metal fluorides, metal oxides and organic insulation materials (such as poly(methyl methacrylate)). Examples of electroluminescent devices provided with an insulation layer having a thickness of not more than 5 nm include devices provided with an insulation layer having a thickness of not more than 5 nm adjacent to the cathode, and devices provided with an insulation layer having a thickness of not more than 5 nm adjacent to the anode.

—Other Structural Elements—

The device described above may further contain a sealing member on the opposite side to the substrate, with the light emitting layer and the like disposed between the substrate and the sealing member. Furthermore, the device may also contain other optional structural elements to configure a display device, including filters such as color filters and fluorescence conversion filters, and circuits and wiring required for driving the pixels.

—Method for Producing Electroluminescent Device Using Layered Structure of the Present Invention—

The electroluminescent device using the layered structure of the present invention can be produced, for example, by sequentially stacking each of the layers on a substrate. Specifically, the electroluminescent device can be produced by providing the anode on a substrate, providing layers such as the hole injection layer and the hole transport layer thereon, providing the light emitting layer thereon, providing layers such as the electron transport layer and the electron injection layer thereon, and then stacking the cathode on top. In another production method, the electroluminescent device can be produced by providing the cathode on a substrate, providing layers such as the electron injection layer, the electron transport layer, the light emitting layer, the hole transport layer and the hole injection layer thereon, and then stacking the anode on top. In yet another production method, the electroluminescent device can be produced by bonding together, in an opposing relationship, the anode or an anode-side substrate having one or more layers stacked on the anode, and the cathode or a cathode-side substrate having one or more layers stacked on the cathode.

Further, the present invention provides the layered structure described above, in which the hole injection layer and/or the hole transport layer has a crosslinked structure.

Moreover, the present invention provides an electronic device having the layered structure of the present invention.

Examples of the crosslinking method include the following methods (a) and (b).

(a) A method in which a functional group having crosslinking reactivity is introduced in advance into the aromatic compound having a structural unit represented by formula (1), and a crosslinking reaction is performed during or after formation of the layered structure.

(b) A method in which a crosslinking agent containing a functional group having crosslinking reactivity is added in advance to the aromatic compound having a structural unit represented by formula (1), and a crosslinking reaction is performed during or after formation of the layered structure.

Examples of the functional group having crosslinking reactivity used in the crosslinking method (a) include one or more groups selected from the group consisting of a vinyl group, acetylene group, butenyl group, acryloyl group, acrylamide group, methacryloyl group, methacrylamide group, vinyl ether group, vinylamino group, silanol group, cyclopropyl group, cyclobutyl group, epoxy group, oxetane group, diketene group, episulfide group, lactone group, lactam group and benzocyclobutene group.

Examples of the crosslinking agent containing a functional group having crosslinking reactivity used in the crosslinking method (b) include compounds having two or more of one or more groups selected from the group consisting of a vinyl group, acetylene group, butenyl group, acryloyl group, acrylamide group, methacryloyl group, methacrylamide group, vinyl ether group, vinylamino group, silanol group, cyclopropyl group, cyclobutyl group, epoxy group, oxetane group, diketene group, episulfide group, lactone group, lactam group and benzocyclobutene group.

Examples of the crosslinking reaction used include thermal reactions, photoreactions, and reactions that use a radical initiator.

Further, by performing the above crosslinking reaction within the hole injection layer and/or hole transport layer comprising the aromatic compound having a structural unit represented by formula (1) according to the present invention, the hole injection layer and/or hole transport layer can be made insoluble in solvents. As a result, application of the hole transport layer and the light emitting layer can be performed using the same solvent as that used in producing the hole injection layer and/or hole transport layer, which can sometimes simplify the production process for the layered structure.

Furthermore, the present invention provides an aromatic compound having a structural unit represented by the following formula (3).

[Chemical Formula 21]

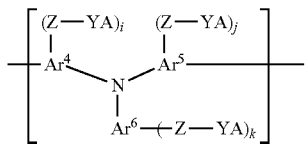
(3)

In the formula, $Ar^4$, $Ar^5$, $Ar^6$, Y, A, i, j and k are the same as defined above, and each Z independently represents a divalent hydrocarbon group which may be substituted.

Z represents a divalent hydrocarbon group which may be substituted. Z is preferably a divalent hydrocarbon group (hydrocarbylene group) of 1 to 50 carbon atoms which may be substituted, and more preferably a hydrocarbylene group of 2 to 40 carbon atoms which may be substituted, and in terms of ensuring good solvent solubility and improving the workability within elements and devices, is still more preferably a hydrocarbylene group of 6 to 30 carbon atoms which may be substituted. The number of carbon atoms in Z is preferably not more than 50, as this facilitates an increase in the effect of introducing the portion represented by —YA. Among the above hydrocarbylene groups, in terms of ensuring good solvent solubility and improving the workability within elements and devices, an alkylene group is preferable. A linear group is preferred as the alkylene group.

If the total of all the structural units in the aromatic compound having the structural unit represented by formula (3) is deemed 100 mol %, then the proportion of the structural unit represented by formula (3) is preferably within a range from not less than 1 mol % to not more than 100 mol %, more preferably within a range from not less than 1 mol % to not more than 99 mol %, still more preferably within a range from not less than mol % to not more than 90 mol %, still more preferably within a range from not less than 10 mol % to not more than 80 mol %, and particularly preferably within a range from not less than 20 mol % to not more than 70 mol %.

Specific examples of formula (3) include the aforementioned structural units (1a) to (1c), (1f), (1g), (1i) to (1z), (1a2) to (1h2), (1a3) to (1h3), (1k3), (1a4) to (1i4), and (1k4). In terms of achieving high polarity and facilitating solubility in high-polarity solvents, and suppressing thermal decomposition, (1a) to (1c), (1f), (1g), and (1i) to (1z) are preferable.

Among these structural units (1a) to (1c), (1f), (1g), and (1i) to (1z), structural units (1a), (1b), (1c), (1l), (1k), (1m), (1n), (1p), (1q), (1r), (1s), (1t), (1v), (1y) and (1z) are preferable, (1a), (1c), (1l), (1p), (1q), (1r), (1t), (1y) and (1z) are more preferable, and (1a), (1c), (1r), (1t) and (1y) are still more preferable.

Further, the present invention provides an aromatic compound represented by the following formula (4).

[Chemical Formula 22]

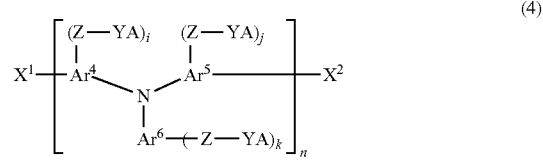
(4)

In the formula, $Ar^4$, $Ar^5$, $Ar^6$, A, Y, Z, i, j and k represent the same meanings as defined above, and when a plurality of one or more of $Ar^4$, $Ar^5$, $Ar^6$, A, Y, Z, i, j and k exists, each item of the plurality may be the same as, or different from, each other item of the plurality, n represents an integer of 1 or greater, and each of $X^1$ and $X^2$ independently represents a hydrogen atom or a monovalent group.

Examples of the monovalent group for $X^1$ and $X^2$ include a hydrocarbyl group and hydrocarbyloxy group.

When the hydrocarbyl group is an alkyl group, an alkyl group of 1 to 20 carbon atoms is preferable, and examples include linear, branched or cyclic alkyl groups such as a methyl group, ethyl group, n-propyl group, iso-propyl group, n-butyl group, sec-butyl group, iso-butyl group, tert-butyl group, n-pentyl group, 2,2-dimethylpropyl group, n-hexyl group, cyclohexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group and n-eicosyl group. In these listed alkyl groups, a portion of the hydrogen atoms may each be substituted with an alkyl group, alkoxy group, alkylamino group, aryl group, aryloxy group, arylamino group or halogen atom, and in such cases, the number of carbon atoms of the hydrocarbyl group is limited to not more than 20.

Further, when the hydrocarbyl group is an aryl group, an aryl group of 6 to 20 carbon atoms is preferable, and examples include a phenyl group, 1-naphthyl group, 2-napthyl group, 3-phenanthryl group and 2-anthryl group. In these listed aryl groups, a portion of the hydrogen atoms may each be substituted with an alkyl group, alkoxy group, alkylamino group, aryl group or halogen atom, and in such cases, the number of carbon atoms of the aryl group is limited to not more than 20.

When the hydrocarbyloxy group is an alkoxy group, an alkoxy group of 1 to 20 carbon atoms is preferable, and examples include linear, branched or cyclic alkoxy groups such as a methoxy group, ethoxy group, n-propyloxy group, iso-propyloxy group, n-butyloxy group, sec-butyloxy group, iso-butyloxy group, tert-butyloxy group, n-pentyloxy group, 2,2-dimethylpropyloxy group, n-hexyloxy group, cyclohexyloxy group, n-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, n-hexadecyloxy group, n-heptadecyloxy group, n-octadecyloxy group, n-nonadecyloxy group and n-eicosyloxy group. In these listed alkoxy groups, a portion of the hydrogen atoms may each be substituted with an alkyl group, alkoxy group, alkylamino group, aryl group or halogen atom, and in such cases, the number of carbon atoms of the alkoxy group is limited to not more than 20.

Further, when the hydrocarbyloxy group is an aryloxy group, an aryloxy group of 6 to 20 carbon atoms is preferable, and examples include a phenyloxy group, 1-naphthyloxy group, 2-napthyloxy group, 3-phenanthryloxy group and 2-anthryloxy group. In these listed aryloxy groups, a portion of the hydrogen atoms may each be substituted with an alkyl group, alkoxy group, alkylamino group, aryl group, aryloxy group, arylamino group or halogen atom, and in such cases, the number of carbon atoms of the hydrocarbyloxy group is limited to not more than 20.

Further examples of the monovalent group for $X^1$ and $X^2$ include one or more groups selected from the group consisting of the following groups:

—F, —Cl, —Br, —I, —OH, —CN, —CO$_2$H, —CO$_2$R$^7$, —Si(CH$_3$)$_3$, —Si(CH$_3$)$_2$C(CH$_3$)$_3$, —B(OR$^5$)(OR$^6$), —CO$_2$R$^7$, —COR$^7$, —O—SO$_2$—CH$_3$, —O—SO$_2$—CF$_3$, —O—SO$_2$-(p-C$_6$H$_4$)—CH$_3$, —O—SO$_2$—C$_6$H$_5$, —P(C$_6$H$_5$)$_2$, —P(=O)(C$_6$H$_5$)$_2$, and Ar$^8$ wherein each of $R^5$, $R^6$ and $R^7$ independently represents a monovalent group, the monovalent group may be substituted with a group selected from the group consisting of a fluorine atom, alkyl groups of 1 to 20 carbon atoms which may have a substituent, and aryl groups of 6 to 20 carbon atoms which may have a substituent, $R^5$ and $R^6$ may be mutually bonded to form a ring, and Ar$^8$ represents a monovalent aromatic group, examples of which include a phenyl group, 1-naphthyl group, 2-naphthyl group, 3-phenanthryl group and 2-anthryl group.

A hydrogen atom or a group selected from the group consisting of the following groups is particularly preferred for $X^1$ and $X^2$, which may be the same or different.

—B(OR$^5$)(OR$^6$), Ar$^8$

Moreover, n represents an integer of 1 or greater, is preferably at least 1 and not more than 1,000,000, more preferably at least 1 and not more than 500,000, still more preferably at least 1 and not more than 100,000, and particularly preferably at least 1 and not more than 1,000.

The polystyrene-equivalent number-average molecular weight (Mn) of the aromatic compound of the present invention is preferably not less than 100 and not more than 1,000,000, more preferably not less than 500 and not more than 500,000, and still more preferably not less than 1,000 and not more than 200,000. This Mn value can be determined by size exclusion chromatography (SEC).

Specific examples of the aromatic compound represented by the above formula (4) include aromatic compounds represented by the following formulas (2a) to (2c), (2f), (2g), and (2i) to (2z).

[Chemical Formula 23]

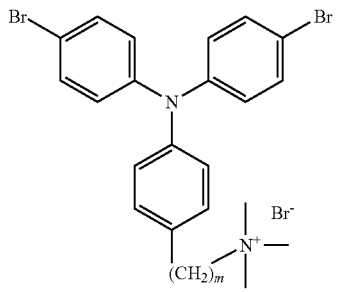
(2a)

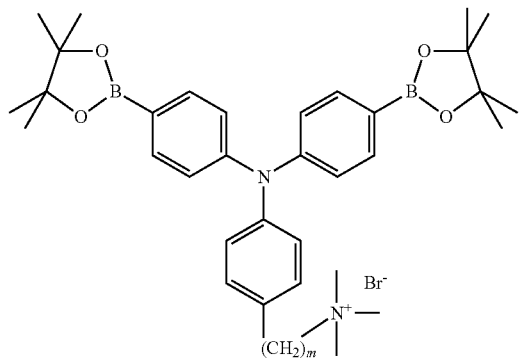
(2b)

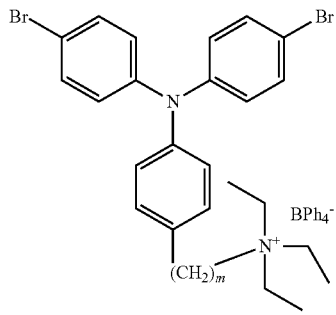
(2c)

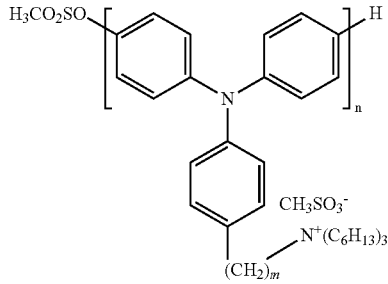
(2f)

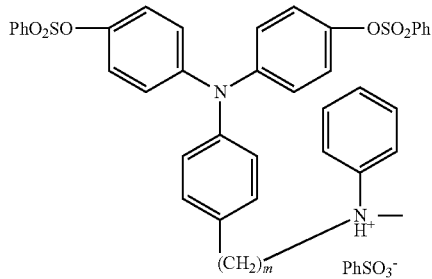
(2g)

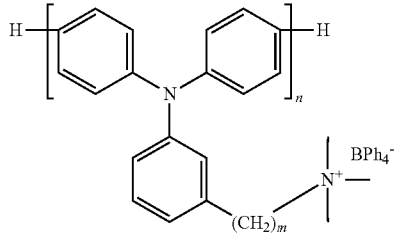
(2i)

-continued
(2j)
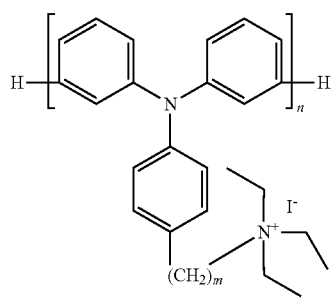
(2k)
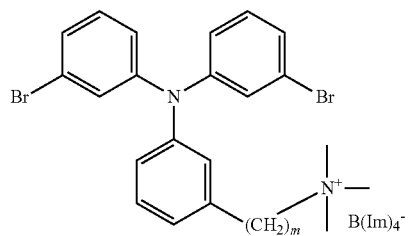
(2l)
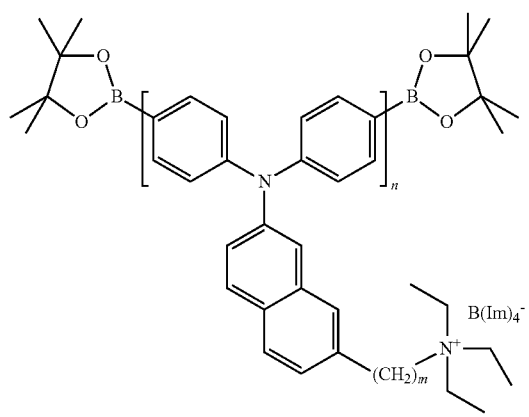
(2m)
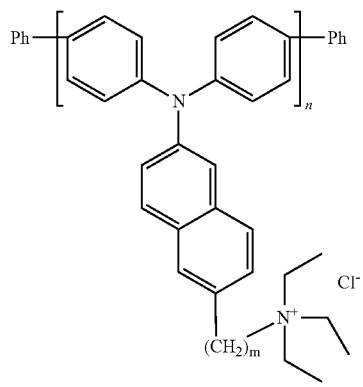
-continued
[Chemical Formula 24]
(2n)
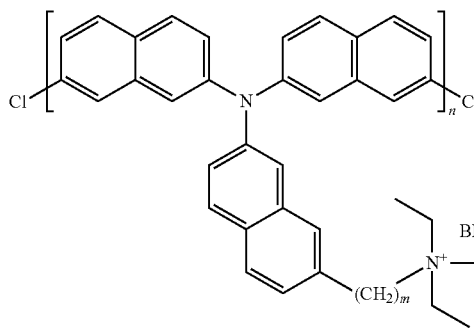
(2o)
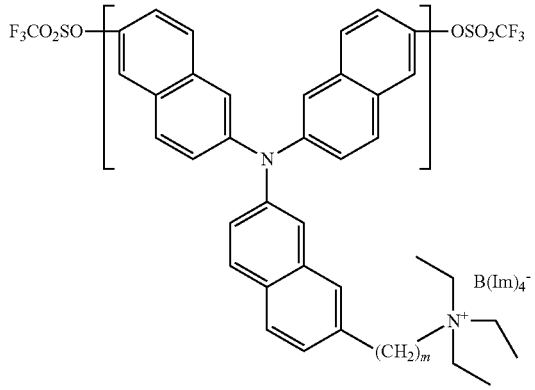
(2p)
(2q)
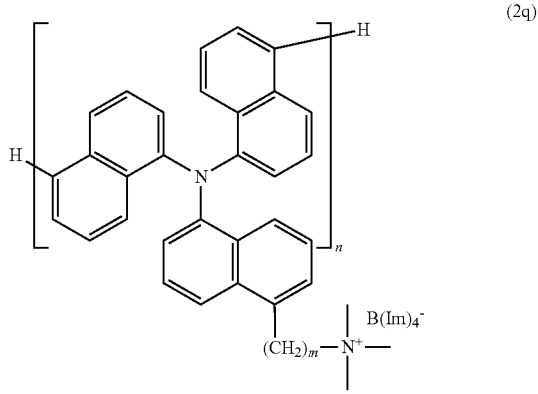

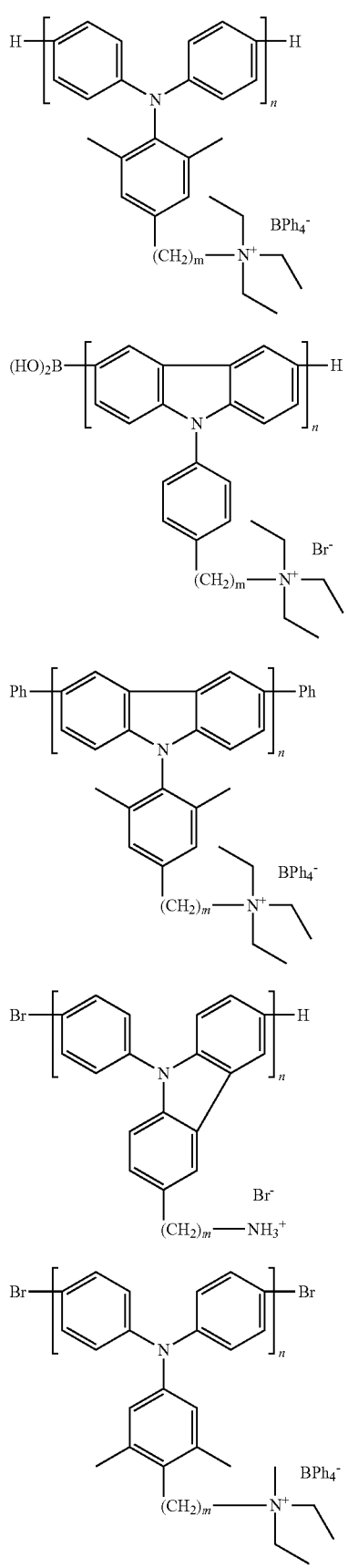
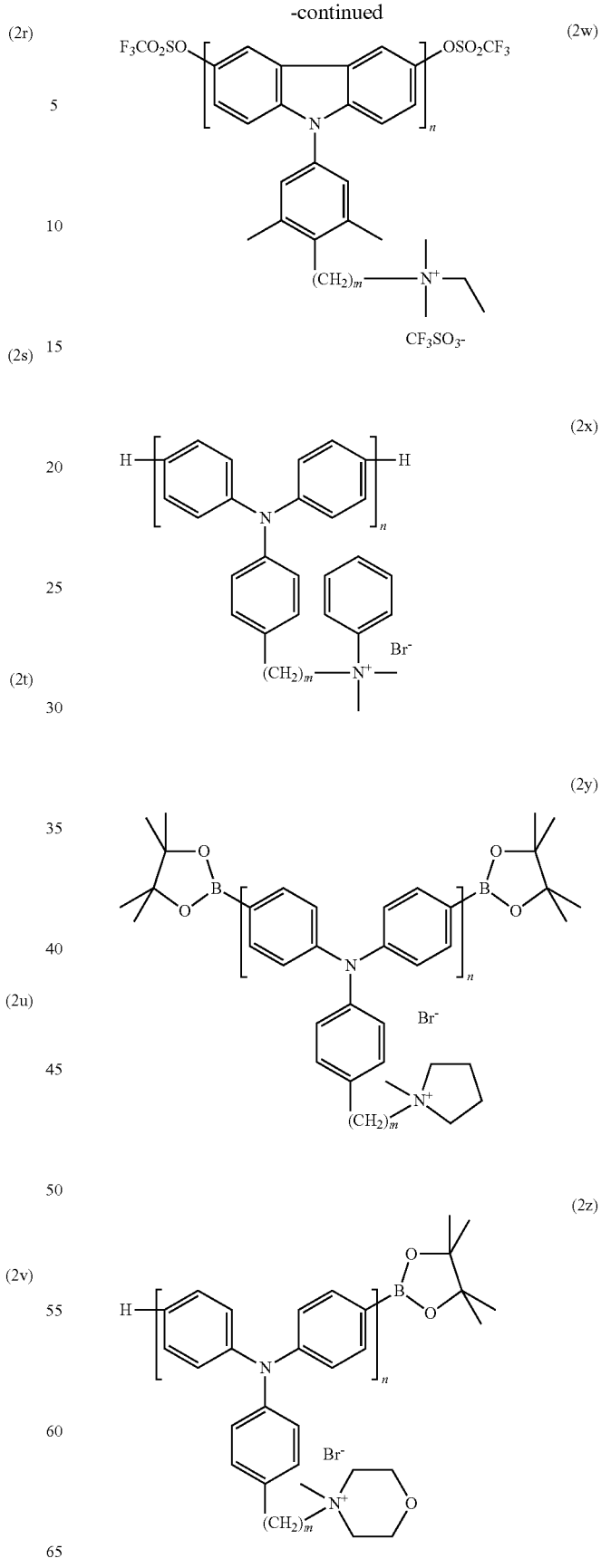
m and n represent the same meanings as defined above.

Further specific examples of the aromatic compound represented by formula (4) include aromatic compounds represented by the following formulas (2a2) to (2h2).

[Chemical Formula 25]

(2a2)
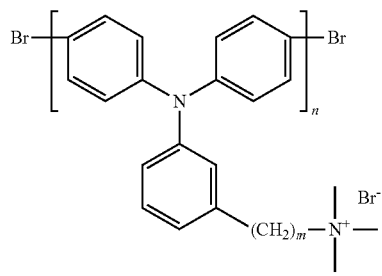

(2b2)
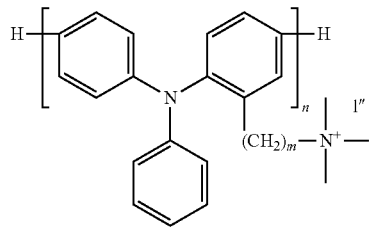

(2c2)
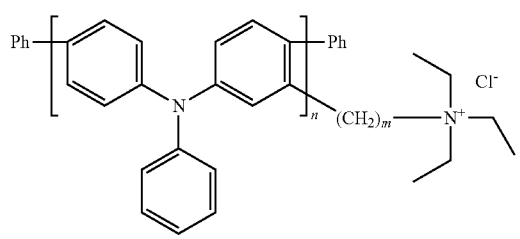

(2d2)
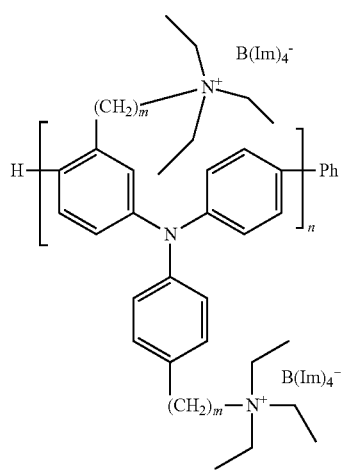

(2e2)
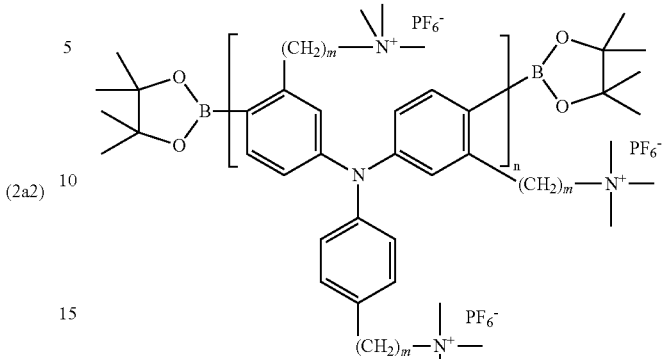

(2f2)
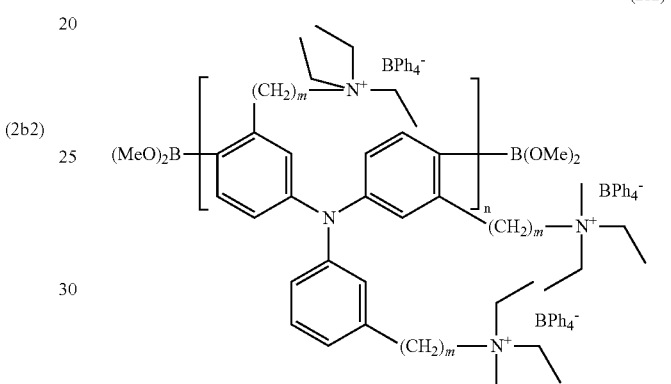

(2g2)
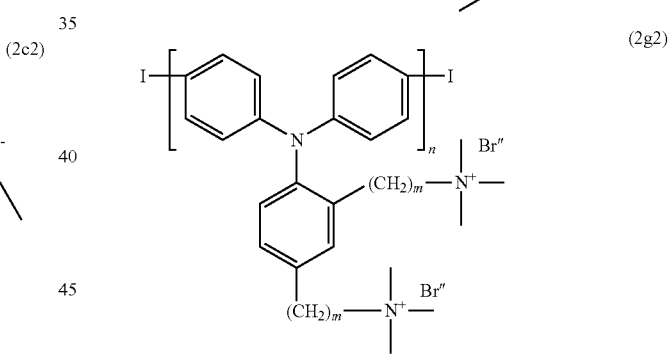

(2h2)
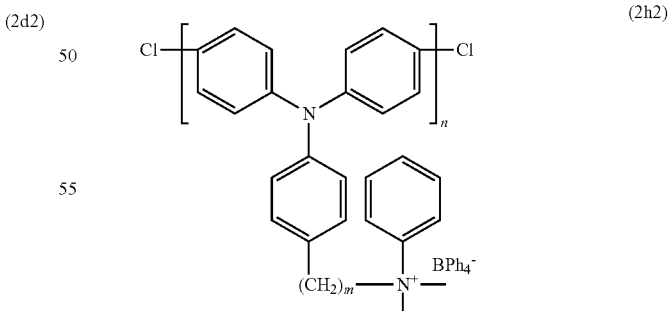

m and n represent the same meanings as defined above.

Still further specific examples of the aromatic compound represented by formula (4) include aromatic compounds represented by the following formulas (2a3) to (2h3).

[Chemical Formula 26]
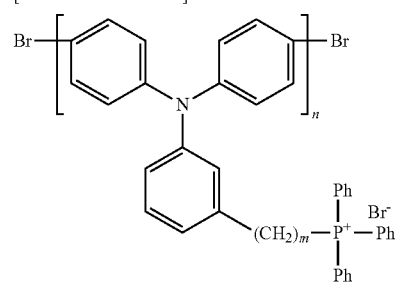
(2a3)
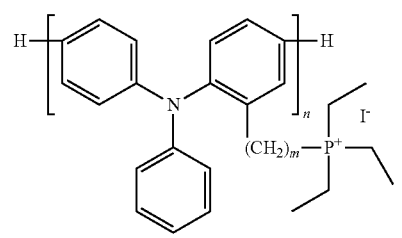
(2b3)
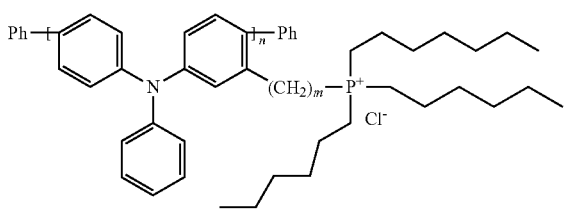
(2c3)
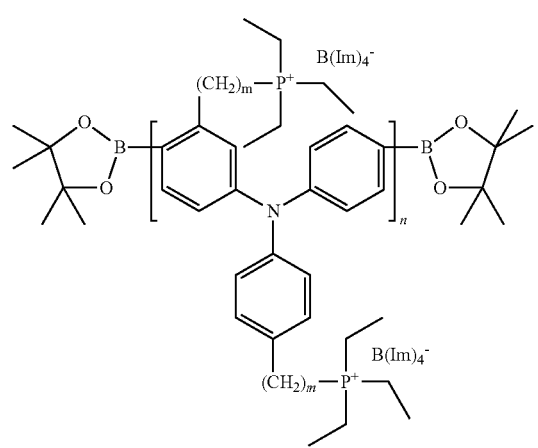
(2d3)
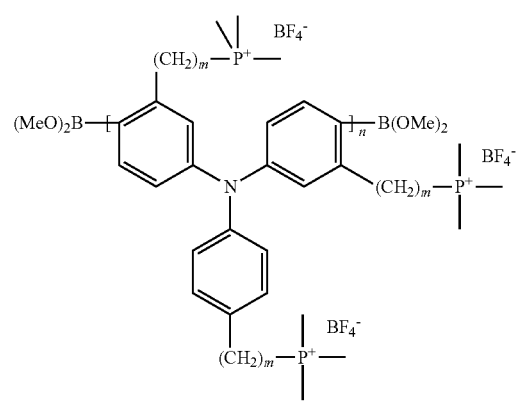
(2e3)
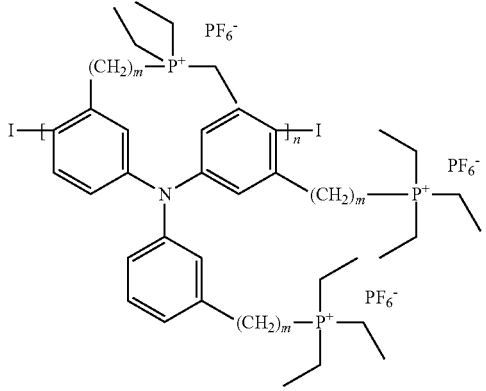
(2f3)
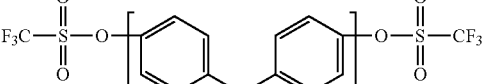
(2g3)
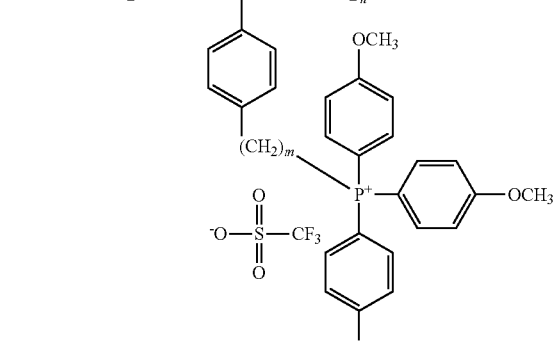
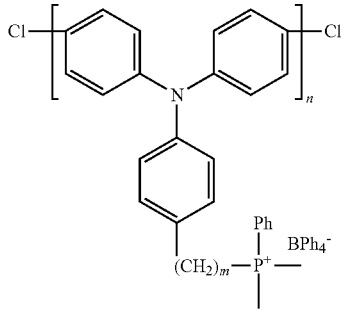
(2h3)
m and n represent the same meanings as defined above.
Still further specific examples of the aromatic compound represented by formula (4) include aromatic compounds represented by the following formulas (2a4) to (2h4).
[Chemical Formula 27]
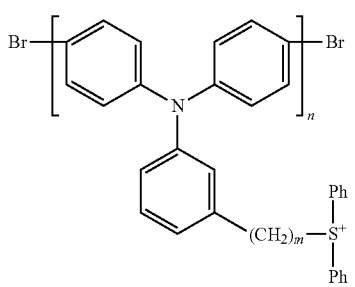
(2a4)

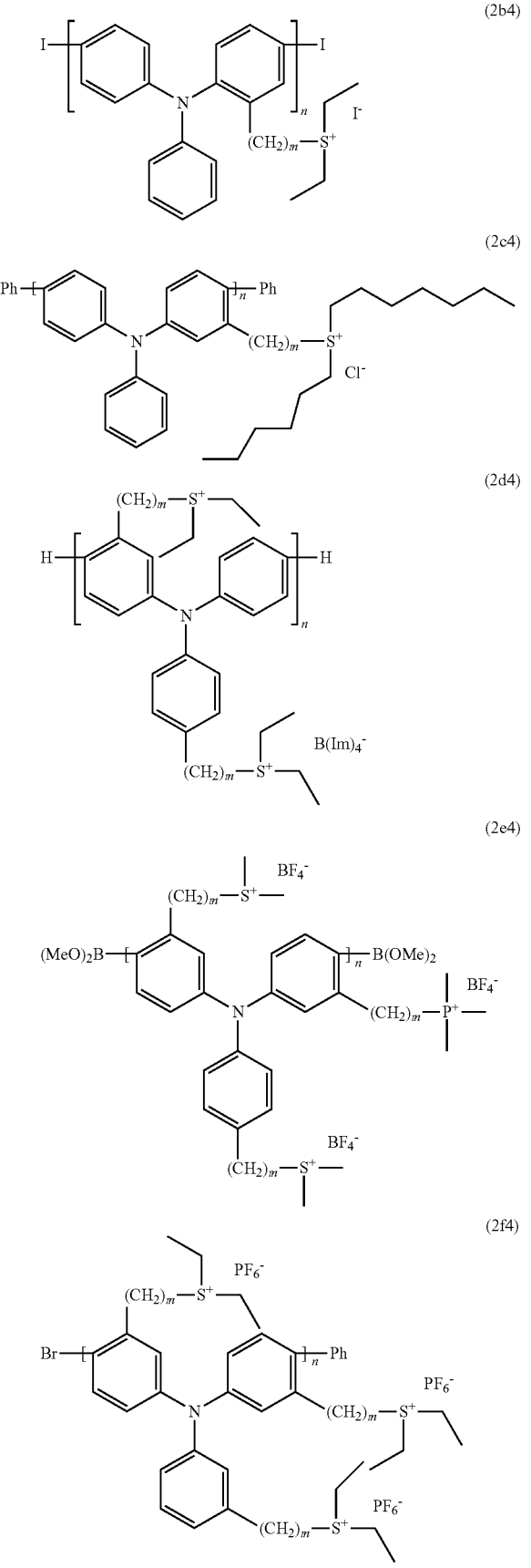

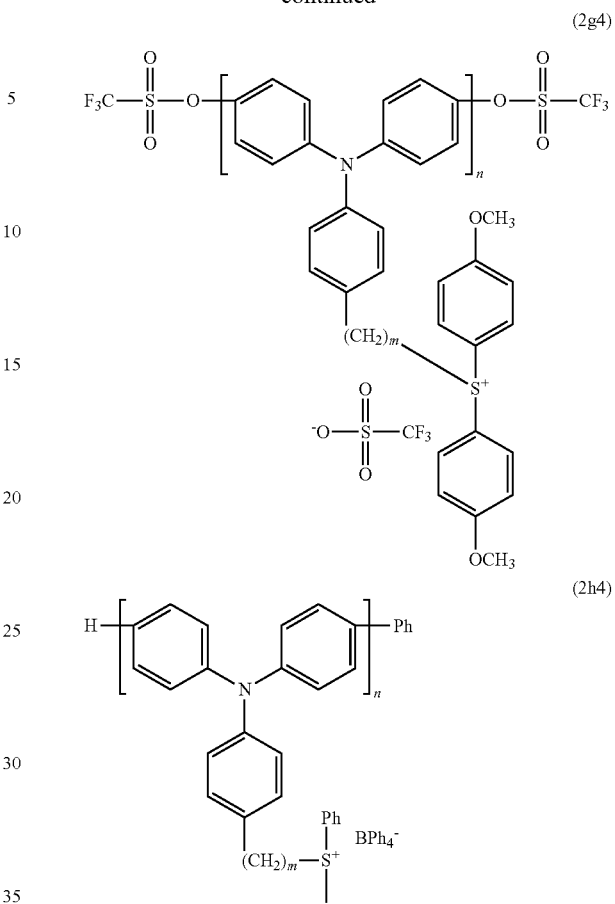

m and n represent the same meanings as defined above.

Among these compounds (2a) to (2c), (2f), (2g), (2i) to (2z), (2a2) to (2h2), (2a3) to (2h3), and (2a4) to (2h4), in terms of achieving high polarity and facilitating solubility in high-polarity solvents, and suppressing thermal decomposition, (2a) to (2c), (2f), (2g), and (2i) to (2z) are preferable.

Among these compounds (2a) to (2c), (2f), (2g), and (2l) to (2z), the compounds (2a), (2b), (2c), (2l), (2k), (2m), (2n), (2p), (2q), (2r), (2s), (2t), (2v), (2y) and (2z) are preferable, (2a), (2c), (2l), (2p), (2q), (2r), (2t), (2y) and (2z) are more preferable, and (2a), (2c), (2r), (2t) and (2y) are still more preferable.

In one embodiment of the present invention, the aromatic compound represented by the above formula (4) is an aromatic compound represented by the following formula (4-1), in which $X^6$ and $X^7$ are functional groups selected from the following group of functional groups and may be the same or different, and $Ar^4$, $Ar^5$, $Ar^6$, A, Y, Z, i, j, k and n represent the same meanings as defined above.

[Chemical Formula 28]

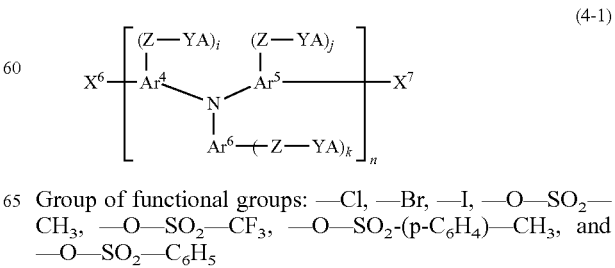

Group of functional groups: —Cl, —Br, —I, —O—SO$_2$—CH$_3$, —O—SO$_2$—CF$_3$, —O—SO$_2$-(p-C$_6$H$_4$)—CH$_3$, and —O—SO$_2$—C$_6$H$_5$ Specific examples of formula (4-1) include the aforementioned compounds (2a), (2c), (2l), (2f), (2g), (2k), (2n), (2o), (2p), (2u), (2v), (2w), (2a2), (2g2), (2h2), (2a3), (2f3), (2g3), (2h3), (2a4), (2b4) and (2g4).

In another embodiment of the present invention, the aromatic compound represented by the above formula (4) is an aromatic compound represented by the following formula (4-2), in which $X^8$ and $X^9$ are functional groups selected from the following group of functional groups and may be the same or different, and $Ar^4$, $Ar^5$, $Ar^6$, A, Y, Z, i, j, k and n represent the same meanings as defined above.

[Chemical Formula 29]

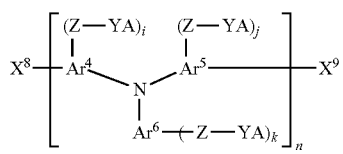

(4-2)

Group of functional groups: $-B(OR^5)(OR^6)$ (wherein $R^5$ and $R^6$ represent the same meanings as defined above)

Specific examples of formula (4-2) include the aforementioned compounds (2b), (2l), (2y), (2z), (2e2), (2f2), (2d3), (2e3), (2e4) and (2g4).

Moreover, the present invention also provides a manufacturing method in which the aromatic compound represented by formula (4-1) and/or formula (4-2) is used, and an $sp^2$ carbon-$sp^2$ carbon bond formation reaction is performed, thereby increasing the number of structural units represented by formula (3) and/or the value of n in formula (4). An appropriate method is described below.

A polymerization in which the unit reaction is a coupling reaction using a zero-valent transition metal complex as a catalyst is suitable as the manufacturing method, and a polymerization performed in the presence of a zero-valent transition metal complex and a bidentate or higher compound that can coordinate with the central metal of the zero-valent transition metal complex (hereafter referred to as a "coordination compound") is particularly suitable.

When the $sp^2$ carbon-$sp^2$ carbon bond formation reaction is performed using only the aromatic compound represented by formula (4-1), the use of a nickel(0) complex as the zero-valent transition metal complex is preferable.

Similarly, when the $sp^2$ carbon-$sp^2$ carbon bond formation reaction is performed using the aromatic compound represented by formula (4-1) together with an aromatic compound represented by the following formula (13), the use of a nickel(0) complex as the zero-valent transition metal complex is preferable.

[Chemical Formula 30]

$$X^6-Ar^7-X^7 \qquad (13)$$

In the formula, $Ar^7$, $X^6$ and $X^7$ represent the same meanings as defined above.

The nickel(0) complex may be a zero-valent nickel complex (nickel(0) complex) such as bis(cyclooctadiene)nickel (0), (ethylene)bis(triphenylphosphine)nickel(0) or tetrakis(triphenylphosphine)nickel(0), or
a nickel(0) complex that is formed within the reaction system by reducing and complexing a divalent nickel compound such as a nickel halide (for example, nickel fluoride, nickel chloride, nickel bromide or nickel iodide), a nickel carboxylate (for example, nickel formate or nickel acetate), nickel sulfate, nickel carbonate, nickel nitrate, nickel acetylacetonate or nickel chloride (dimethoxyethane). Among these possibilities, the use of bis(cyclooctadiene)nickel(0), or the conversion of a nickel halide to a nickel(0) complex within the reaction system is preferable for obtaining the aromatic compound of the present invention.

The amount used of the zero-valent transition metal complex can be appropriately optimized in accordance with the type of aromatic compound used and the molecular weight of the obtained coupling product. The use of 0.4 to 5 mol of the zero-valent transition metal complex per 1 mol of the leaving groups ($-X^6$, $-X^7$) is suitable.

Adding a coordination compound in addition to the zero-valent transition metal complex improves the stability of the zero-valent transition metal complex itself during the reaction, and is preferable for ensuring the reaction proceeds smoothly. When a nickel(0) complex is used as the catalyst, 2,2'-bipyridine, 1,10-phenanthroline, methylenebis(oxazoline) or N,N'-tetramethylethylenediamine is preferable as the coordination compound, and 2,2'-bipyridine is particularly preferable. When this type of coordination compound is used, the amount used of the compound is typically within a range from 0.2 to 2 mol, and preferably within a range from 1 to 1.5 mol, per 1 mol of the central metal (such as nickel) of the zero-valent transition metal complex.

When the zero-valent transition metal complex is a nickel (0) complex, divalent nickel compounds are converted within the polymerization reaction system to a nickel(0) complex which can also be used as the nickel(0) complex. In this case, a reducing agent that can reduce the nickel is necessary. Zinc is preferably used as the reducing agent, and this zinc is typically used in a powdered form. When zinc is used, the amount of the zinc is typically at least equimolar but not more than 10 mol, and preferably at least equimolar but not more than 5 mol, per 1 mol of the monomer used. The upper limit for the amount of zinc used is selected so that the after-treatment performed after the reaction does not become troublesome, and so that the reaction does not become unviable economically. The combined use of a divalent nickel compound and zinc is particularly advantageous when the equivalent amount of the divalent nickel compound is lower than the equivalent amount of the monomer used.

The reaction is typically performed in the presence of a solvent. The solvent may be any solvent that is capable of dissolving the monomer used and the aromatic compound of the present invention that is produced. Specific examples of such solvents include aromatic hydrocarbon solvents such as toluene and xylene, ether solvents such as tetrahydrofuran and 1,4-dioxane, aprotic polar solvents such as dimethylsulfoxide (DMSO), N-methyl-2-pyrrolidone (NMP), N,N-dimethylformamide (DMF), N,N-dimethylacetamide (DMAc) and hexamethylphosphoric triamide, and halogenated hydrocarbon solvents such as dichloromethane and dichloroethane. These solvents may be used individually, or two or more solvents may be used in a mixture. Among the various possibilities, an ether solvent or aprotic polar solvent is preferable, and tetrahydrofuran, dimethylsulfoxide, N-methyl-2-pyrrolidone, N,N-dimethylacetamide, or a mixed solvent of two or more of these solvents is more preferable. If the amount used of the solvent is too large, then the reaction tends to proceed poorly, whereas if the amount used is too small, then the viscosity of the reaction solution may increase dramatically, making the after-treatment troublesome, and therefore the amount of the solvent is typically from 1 to 200 times, and preferably from 5 to 100 times, the total weight of the aromatic compound being reacted.

The reaction is typically performed under an atmosphere of an inert gas such as nitrogen gas.

Further, the reaction temperature is typically from 0 to 250° C., and preferably from 30 to 100° C.

The reaction time is typically selected within a range from 0.5 to 48 hours, and the reaction time is preferably determined, for example, by sampling the reaction solution at regular intervals during the reaction, analyzing the samples by measuring the molecular weight or the like of the product, and then setting the reaction time so that the desired product is obtained.

Any of various known techniques can be used for extracting the product from the reaction solution following reaction. Typically, a technique is used in which a poor solvent that is unable to dissolve the product is mixed with the reaction solution to precipitate the polymer, and the precipitated product is then separated by filtration or the like, and this particular technique offers the advantage that the operations are simple. Examples of the poor solvent include water, methanol, ethanol and acetonitrile, and water and methanol are preferred. The molecular weight and chemical structure of the obtained polymer can be determined by typical analysis techniques such as gel permeation chromatography, high performance liquid chromatography and nuclear magnetic resonance spectroscopy (NMR).

When an $sp^2$ carbon-$sp^2$ carbon bond formation reaction is performed using an aromatic compound having a boron functional group, the Suzuki coupling reaction is used, in the presence of a base, using palladium as the zero-valent transition metal complex.

When an aromatic compound represented by the above formula (4-1) and an aromatic compound represented by the above formula (4-2) are used, examples of the reaction include the case where an aromatic compound represented by formula (4-1) and an aromatic compound represented by the following formula (14) are used, and the case where an aromatic compound represented by formula (4-1), an aromatic compound represented by formula (4-2) and an aromatic compound represented by the following formula (14) are used.

[Chemical Formula 31]

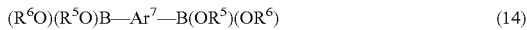

$$(R^6O)(R^5O)B—Ar^7—B(OR^5)(OR^6) \quad (14)$$

In the formula, $Ar^7$, $R^5$ and $R^6$ represent the same meanings as defined above.

Of the groups having reactivity in the above coupling reaction, approximately 50 mol % are preferably selected from among boron functional groups.

Organic solvents suitable for use in the present invention include those solvents capable of dissolving the monomer to form a solution concentration of at least 1 percent, and preferably at least 2 percent. This solvent is preferably a C6 to C20 (namely, 6 to 20 carbon atoms) aromatic group-containing compound, and is more preferably benzene, toluene, xylene, ethylbenzene, mesitylene, anisole, or fluorinated derivatives of these compounds. Of these compounds, toluene is particularly preferred. Because the reaction mixture increases in viscosity as the molecular weight of the aromatic compound polymer increases, the volume of the solvent during the reaction must be sufficient to enable effective mixing of the reaction mixture during reflux. This volume is typically from 5 to 20 mL per 1 g of the aromatic compound, and is preferably approximately 10 mL of toluene per 1 g of the aromatic compound.

Examples of effective bases in the present invention include alkali metal carbonates and bicarbonates. This base is preferably an aqueous alkali metal carbonate solution, such as a 1 mol/L to 2 mol/L solution of sodium carbonate or potassium carbonate.

Palladium may also be added in the form of a Pd(II) salt or a Pd(0) complex. Pd acetate is a preferred Pd(II) salt, and $Pd(Ph_3P)_4$ is a preferred Pd(0) complex. When a Pd(II) salt is used, the addition of 2 to 4 mol of triphenylphosphine ($Ph_3P$) per 1 mol of the Pd salt is advantageous. Further, a Pd(II)-$Ph_3P$ complex such as $PdCl_2(Ph_3P)_2$ can be used. The amount of Pd, relative to the boron functional group, is preferably from $1\times10^{-6}$ mol to 1 mol, more preferably from $1\times10^{-5}$ mol to $1\times10^{-1}$ mol, and particularly preferably $1\times10^{-4}$ mol to $1\times10^{-3}$ mol, per 2 mol of the boron functional group.

The preferred upper limit for the reaction temperature is the boiling point of the immiscible liquid mixture composed of the aqueous base and the solution of the monomer in an organic solvent. Usually, the reaction temperature is preferably restricted to not more than 150° C., more preferably not more than 130° C., and particularly preferably 120° C. or lower.

The reaction is typically performed under an atmosphere of an inert gas such as nitrogen gas.

The reaction time is typically selected within a range from 0.5 to 48 hours, and the reaction time is preferably determined, for example, by sampling the reaction solution at regular intervals during the reaction, analyzing the samples by measuring the molecular weight or the like of the product, and then setting the reaction time so that the desired product is obtained.

Any of various known techniques can be used for extracting the product from the reaction solution following reaction. Typically, a technique is used in which a poor solvent that is unable to dissolve the product is mixed with the reaction solution to precipitate the polymer (the aromatic compound), and the precipitated product is then separated by filtration or the like, and this particular technique offers the advantage that the operations are simple. Examples of the poor solvent include water, methanol, ethanol and acetonitrile, and water and methanol are preferred. The molecular weight and chemical structure of the obtained polymer can be determined by typical analysis techniques such as gel permeation chromatography, high performance liquid chromatography and nuclear magnetic resonance spectroscopy (NMR).

The present invention provides an aromatic compound having a structural unit represented by the following formula (7), namely, an aromatic compound having a leaving group on a hydrocarbon side chain.

[Chemical Formula 32]

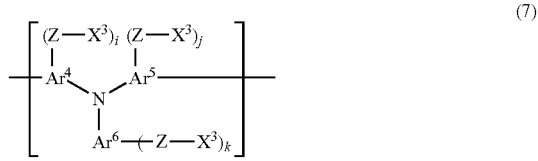

In the formula, $Ar^4$, $Ar^5$, $Ar^6$, Z, i, j and k are the same as defined above, and each $X^3$ independently represents a leaving group.

Examples of the leaving group represented by $X^3$ include groups selected from the following group of functional groups. When two or more types of $X^3$ exist, the groups may be the same or different.

—Cl, —Br, —I, —O—SO$_2$—CH$_3$, —O—SO$_2$—CF$_3$, —O—SO$_2$-(p-C$_6$H$_4$)—CH$_3$, and —O—SO$_2$—C$_6$H$_5$
Examples of the structural unit represented by formula (7) include the following structural units (3a) to (3w).
[Chemical Formula 33]
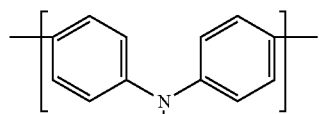
(3a)
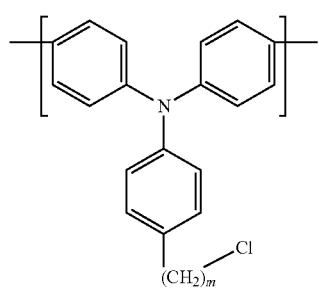
(3b)
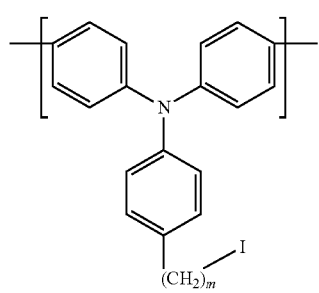
(3c)
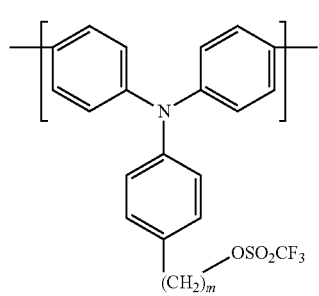
(3d)
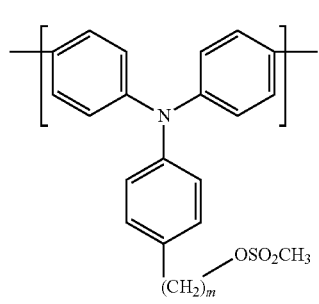
(3e)
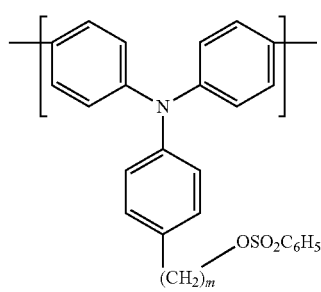
(3f)
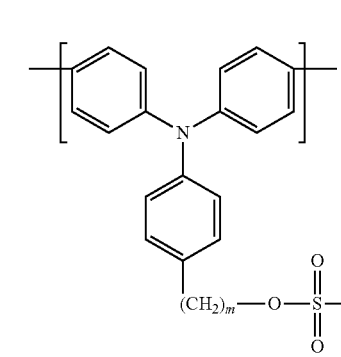
(3g)
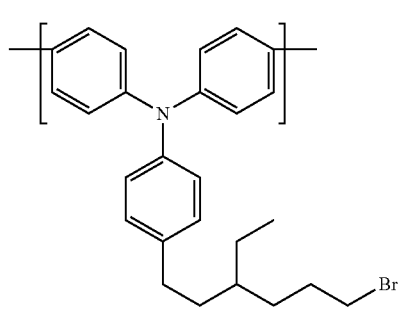
(3h)
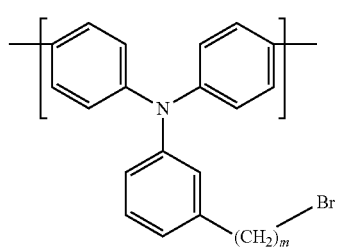
(3i)
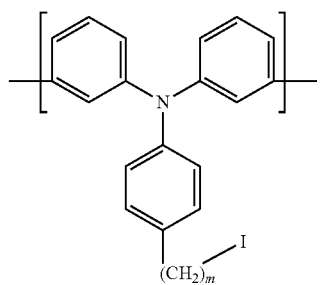
(3j)

-continued
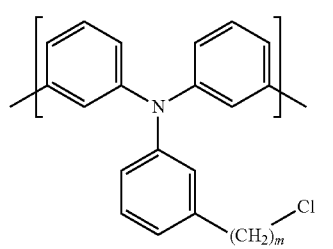 (3k)
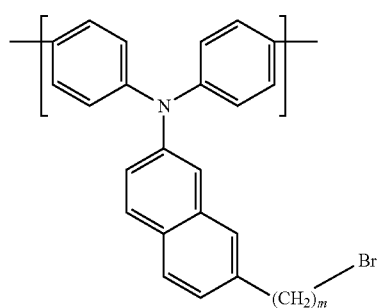 (3l)
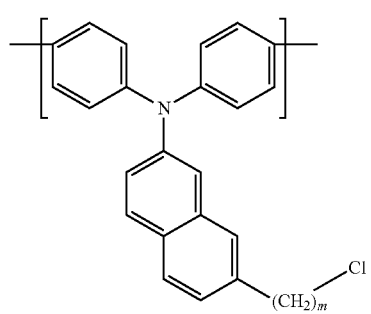 (3m)
[Chemical Formula 34]
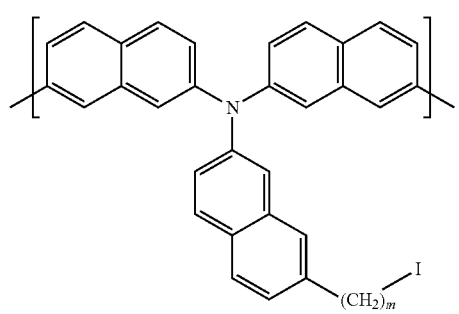 (3n)
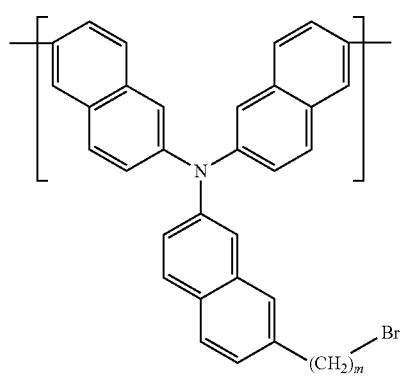 (3o)
-continued
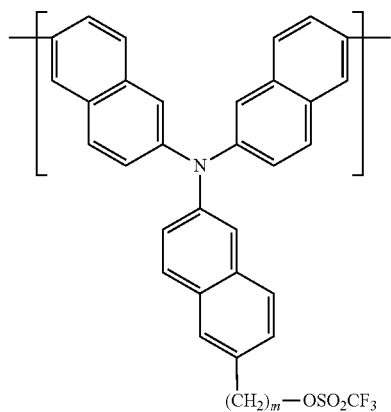 (3p)
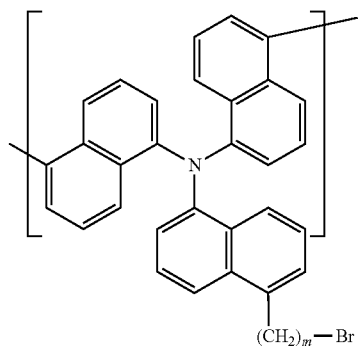 (3q)
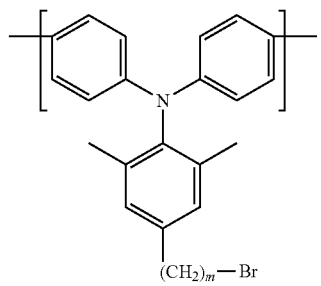 (3r)
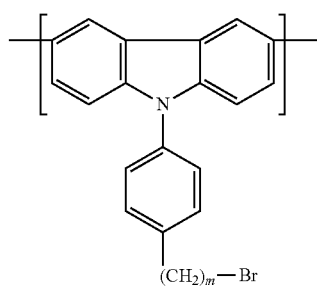 (3s)
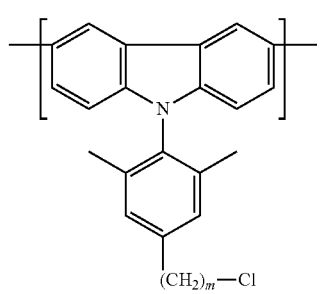 (3t)

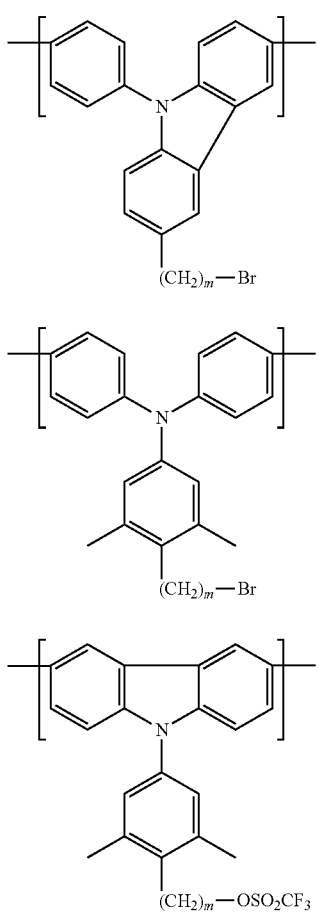
(3u)
(3v)
(3w)
m represents the same meaning as defined above.
Further specific examples of the structural unit represented by formula (7) include the following (3a2) to (3h2). m represents the same meaning as defined above.
[Chemical Formula 35]
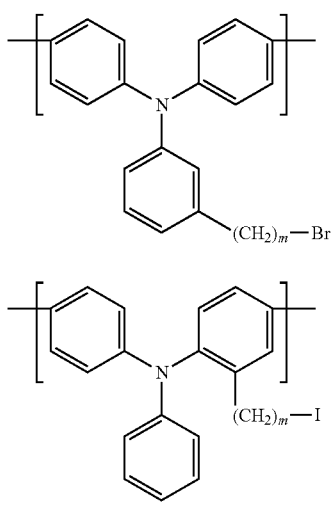
(3a2)
(3b2)
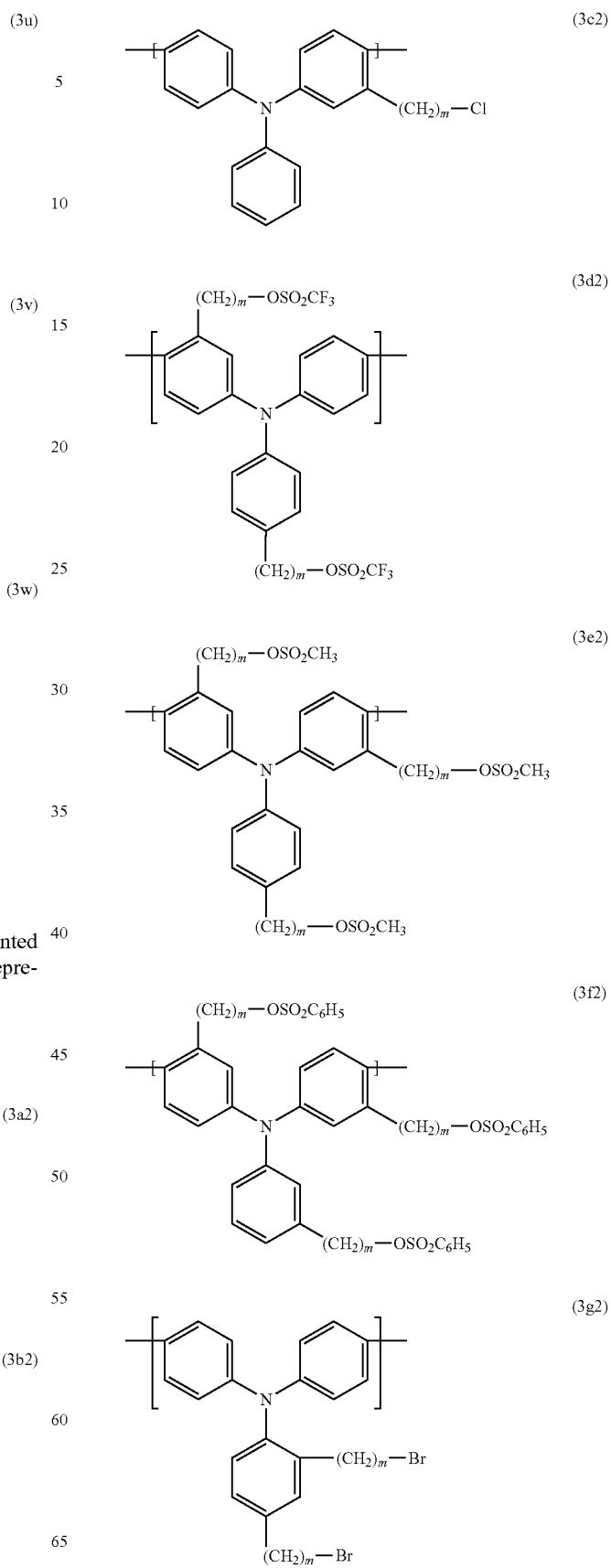
(3c2)
(3d2)
(3e2)
(3f2)
(3g2)

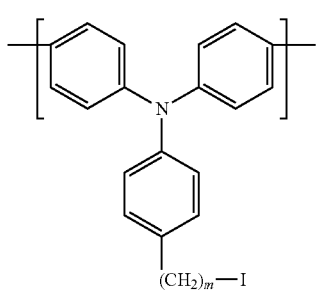
(3h2)

Among these structural units, (3a), (3b), (3c), (3d), (3e), (3f), (3g), (3i), (3j), (3l), (3n), (3o), (3p), (3q), (3r), (3s), (3v) and (3w) are preferable, (3a), (3c), (3d), (3i), (3l), (3n), (3p), (3q), (3r), (3s), (3v) and (3w) are more preferable, (3a), (3c), (3d), (3i), (3l), (3n), (3r), (3s) and (3v) are still more preferable, and (3a), (3c), (3d), (3i), (3r) and (3s) are still more preferable.

If the total of all the structural units in the aromatic compound having the structural unit represented by formula (7) is deemed 100 mol %, then the proportion of the structural unit represented by formula (7) is preferably within a range from not less than 1 mol % to not more than 100 mol %, more preferably within a range from not less than 1 mol % to not more than 99 mol %, still more preferably within a range from not less than 1 mol % to not more than 90 mol %, still more preferably within a range from not less than 10 mol % to not more than 80 mol %, and particularly preferably within a range from not less than 20 mol % to not more than 70 mol %.

Furthermore, the present invention provides an aromatic compound represented by the following formula (8), namely, an aromatic compound having a leaving group on a hydrocarbon side chain.

[Chemical Formula 36]

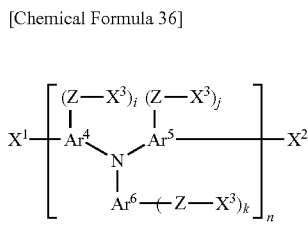
(8)

In the formula, $Ar^4$, $Ar^5$, $Ar^6$, $X^3$, Z, i, j and k represent the same meanings as defined above, and when a plurality of one or more of $Ar^4$, $Ar^5$, $Ar^6$, $X^3$, Z, i, j and k exists, each item of the plurality may be the same as, or different from, each other item of the plurality. n, $X^1$ and $X^2$ are the same as defined above.

Examples of formula (8) include the following formulas (4a) to (4z).

[Chemical Formula 37]

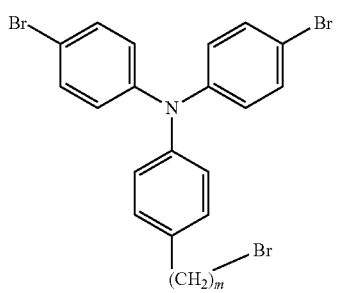
(4a)

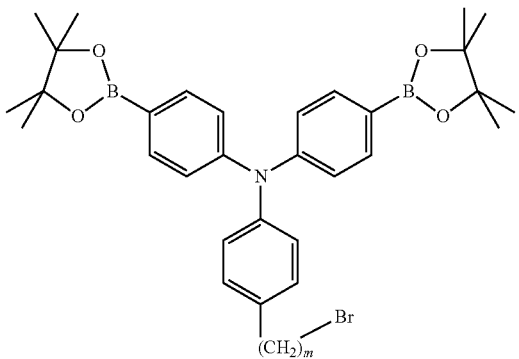
(4b)

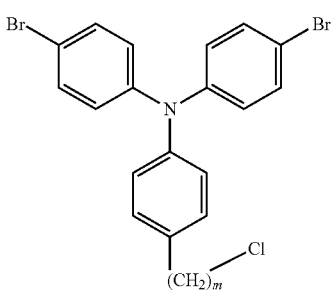
(4c)

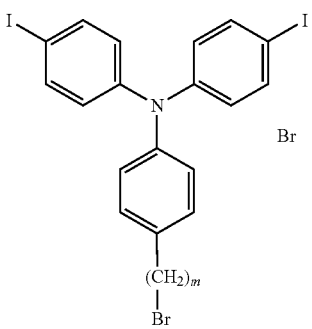
(4d)

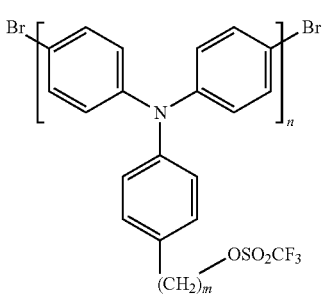
(4e)

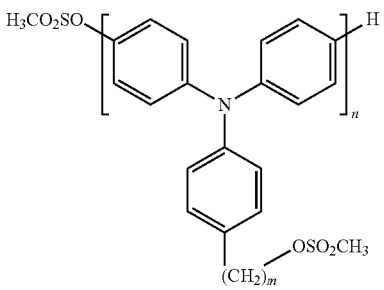
(4f)

(4g)
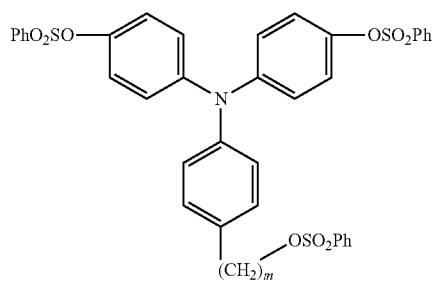
[Chemical Formula 38]
(4h)
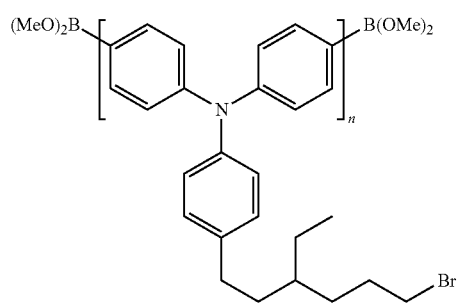
(4i)
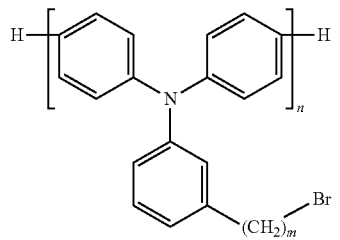
(4j)
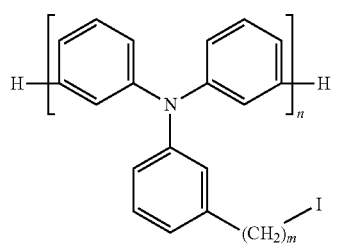
(4k)
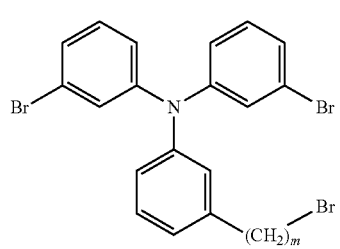
(4l)
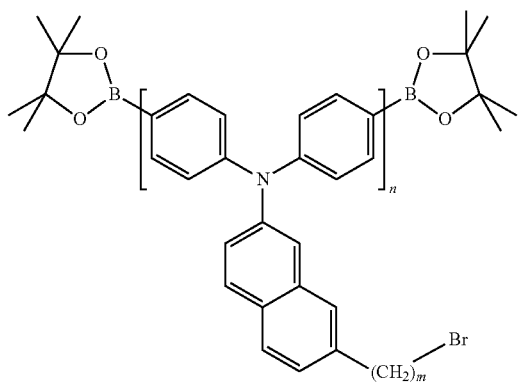
(4m)
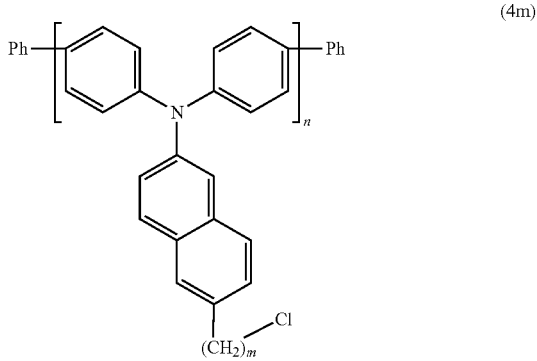
(4n)
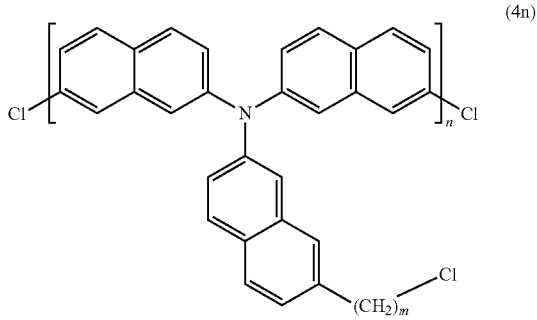
(4o)
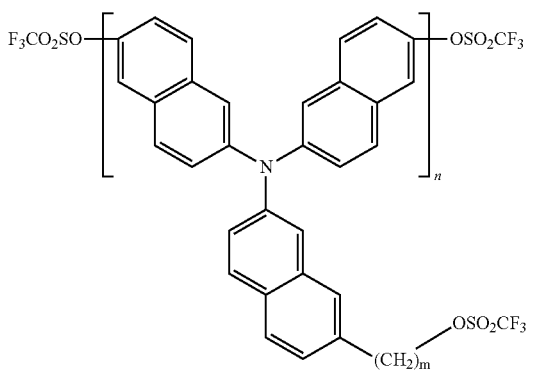

-continued
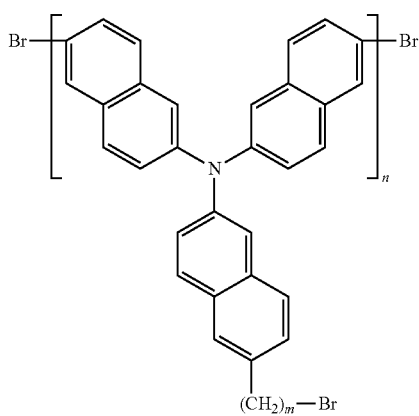
(4p)
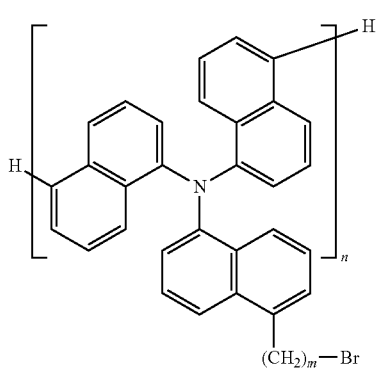
(4q)
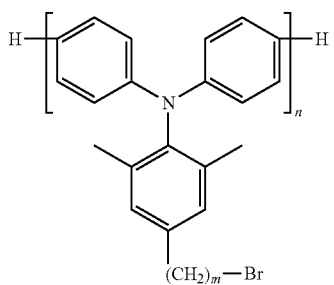
(4r)
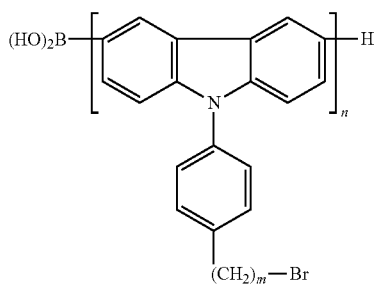
(4s)
-continued
[Chemical Formula 39]
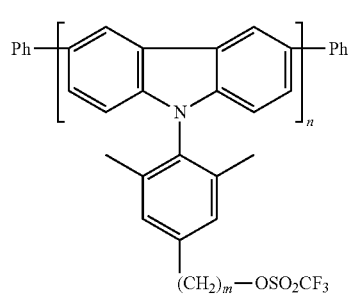
(4t)
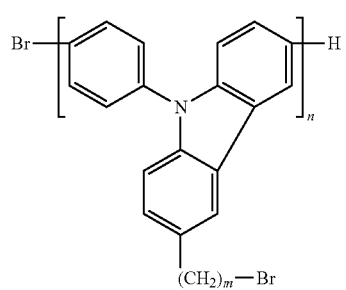
(4u)
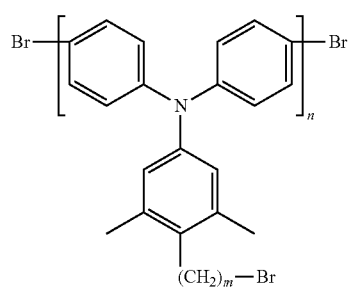
(4v)
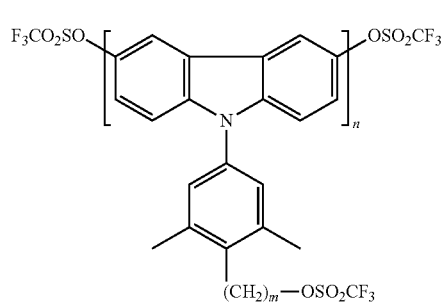
(4w)
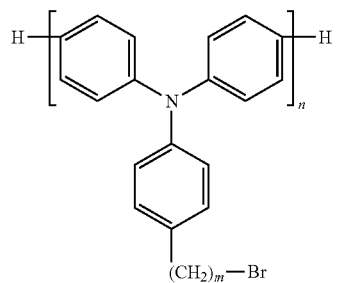
(4x)

(4y)
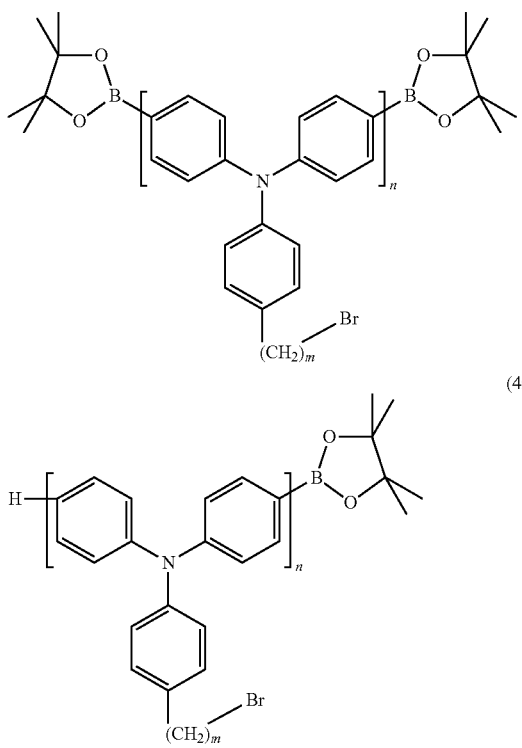
(4z)
(4d2)
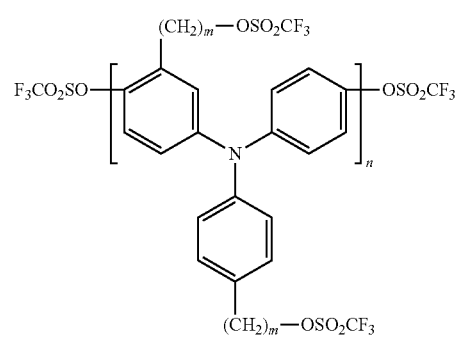
(4e2)
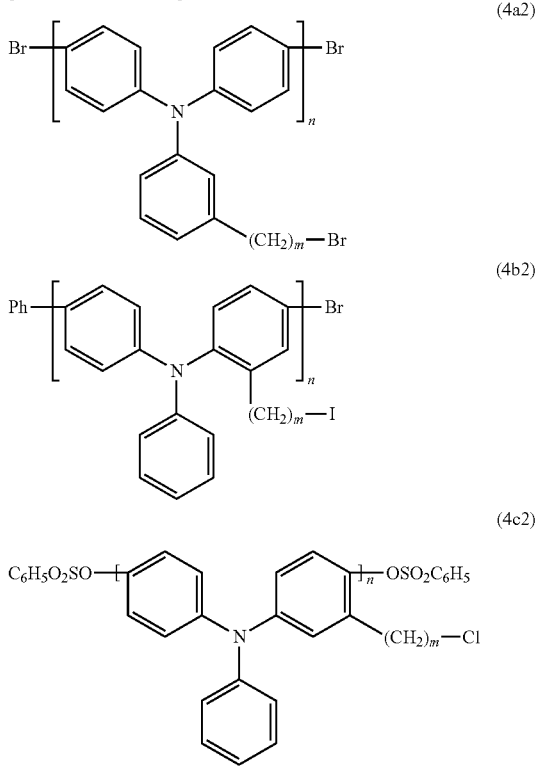
m and n represent the same meanings as defined above.
Further examples of formula (9) include the following formulas (4a2) ti (4h2). m and n represent the same meanings as defined above.
[Chemical Formula 40]
(4a2)
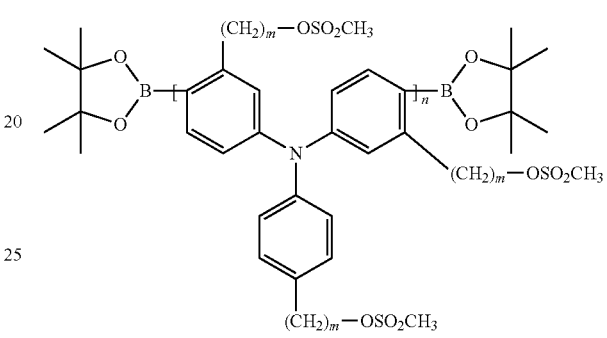
(4f2)
(4b2)
(4g2)
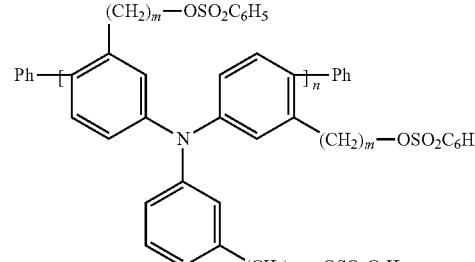
(4c2)
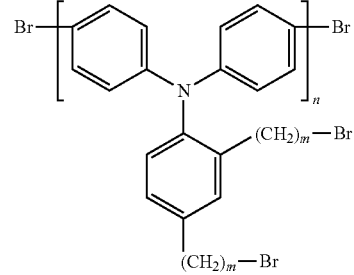
(4h2)
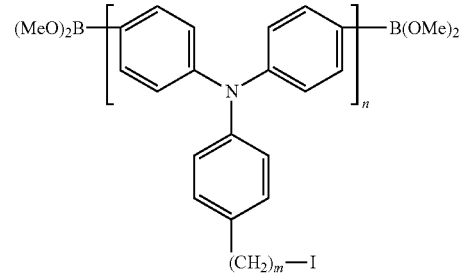
Among these compounds, (4a), (4b), (4c), (4d), (4e), (4f), (4g), (4i), (4j), (4l), (4n), (4o), (4p), (4q), (4r), (4s), (4v), (4w), (4y) and (4z) are preferable, (4a), (4c), (4d), (4i), (4l), (4n), (4p), (4q), (4r), (4s), (4v) and (4w) are more preferable, (4a), (4c), (4d), (4i), (4l), (4n), (4r), (4s) and (4v) are still more preferable, and (4a), (4c), (4d), (4i), (4r) and (4s) are still more preferable.

In one embodiment of the present invention, the aromatic compound represented by the above formula (8) is an aromatic compound represented by the following formula (8-1), in which $X^6$ and $X^7$ are, in the same manner as described above, functional groups selected from the following group of functional groups, and may be the same or different, and $Ar^4$, $Ar^5$, $Ar^6$, Z, $X^3$, i, j, k and n represent the same meanings as defined above.

[Chemical Formula 41]

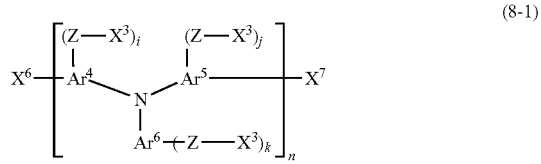

(8-1)

Group of functional groups: —Cl, —Br, —I, —O—SO$_2$—CH$_3$, —O—SO$_2$—CF$_3$, —O—SO$_2$-(p-C$_6$H$_4$)—CH$_3$, and —O—SO$_2$—C$_6$H$_5$ Specific examples of formula (8-1) include the aforementioned compounds (4a), (4c), (4d), (4e), (4f), (4g), (4h), (4k), (4n), (4o), (4p), (4v), (4w), (4a2), (4c2), (4d2) and (4g2).

In another embodiment of the present invention, the aromatic compound represented by the above formula (8) is an aromatic compound represented by the following formula (8-2), in which $X^8$ and $X^9$ are, in the same manner as described above, functional groups selected from the following group of functional groups, and may be the same or different, and $Ar^4$, $Ar^5$, $Ar^6$, Z, $X^3$, i, j, k and n represent the same meanings as defined above.

[Chemical Formula 42]

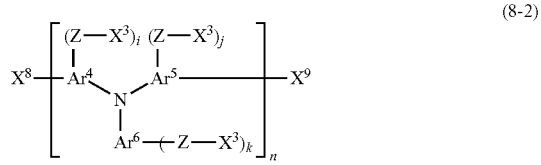

(8-2)

Group of functional groups: —B(OR$^5$)(OR$^6$) (wherein R$^5$ and R$^6$ represent the same meanings as defined above)

Specific examples of formula (8-2) include the aforementioned compounds (4b), (4h), (4l), (4y), (4e2) and (4h2).

The present invention further provides a manufacturing method in which the compound represented by the above formula (8) is used, and an sp$^2$ carbon-sp$^2$ carbon bond formation reaction is performed, thereby increasing the number of structural units represented by the above formula (7) and/or the value of n in the aromatic compound represented by formula (8). In this case, the aforementioned method for manufacturing an aromatic compound having a structural unit represented by formula (3) and/or an aromatic compound represented by formula (4) can be applied in the same manner.

$X^3$ in formula (8-1) or (8-2) can be substituted with YA containing the desired anion A by a known method such as the method disclosed in JP 2009-242724 A.

Moreover, the present invention also provides a method for manufacturing an aromatic compound having a structural unit represented by formula (3), the method comprising reacting an aromatic compound having a structural unit represented by formula (7) with a nitrogen compound represented by formula (11-1) below, a phosphorus compound represented by formula (11-2) below, a sulfur compound represented by formula (11-3) below, or a combination of two or more of these compounds, thereby converting the aromatic compound to an onium salt thereof.

NR$^1$R$^2$R$^3$                  (11-1)

PR$^1$R$^2$R$^3$                  (11-2)

SR$^1$R$^2$                   (11-3)

In each of formulas (11-1), (11-2) and (11-3), R$^1$, R$^2$ and R$^3$ are the same as defined above.

Tertiary amine compounds can be used favorably as the nitrogen compound represented by formula (11-1). Specific examples of such nitrogen compounds include trimethylamine, triethylamine, tri-1-propylamine, tri-2-propylamine, tri-n-butylamine, tri-2-butylamine, tri-1-pentylamine, tri-2-pentylamine, tri-3-pentylamine, trineopentylamine, tricyclopentylamine, tri-1-hexylamine, tri-2-hexylamine, tri-3-hexylamine, pyridine, N-methylimidazole, N-methylpyrrolidine and N-methylmorpholine.

Tertiary phosphine compounds can be used favorably as the phosphorus compound represented by formula (11-2). Specific examples of such phosphine compounds include trimethylphosphine, triethylphosphine, tri-1-propylphosphine, tri-2-propylphosphine, tri-n-butylphosphine, tri-2-butylphosphine, tri-1-pentylphosphine, tri-2-pentylphosphine, tri-3-pentylphosphine, trineopentylphosphine, tricyclopentylphosphine, tri-1-hexylphosphine, tri-2-hexylphosphine, tri-3-hexylphosphine, triphenylphosphine, tri(4-methylphenyl)phosphine, tri(3-methylphenyl)phosphine, tri(2-methylphenyl)phosphine, tri(4-methoxyphenyl)phosphine, tri(3-methoxyphenyl)phosphine and tri(2-methoxyphenyl)phosphine.

Sulfide compounds can be used favorably as the sulfur compound represented by formula (11-3). Specific examples of such sulfide compounds include dimethyl sulfide, diethyl sulfide, di-1-propyl sulfide, di-2-propyl sulfide, di-n-butyl sulfide, di-2-butyl sulfide, di-1-pentyl sulfide, di-2-pentyl sulfide, di-3-pentyl sulfide, dineopentyl sulfide, dicyclopentyl sulfide, di-1-hexyl sulfide, di-2-hexyl sulfide, di-3-hexyl sulfide, diphenyl sulfide, di(4-methylphenyl) sulfide, di(3-methylphenyl) sulfide, di(2-methylphenyl) sulfide, di(4-methoxyphenyl) sulfide, di(3-methoxyphenyl) sulfide and di(2-methoxyphenyl) sulfide.

Among these compounds represented by formulas (11-1), (11-2) and (11-3), in terms of ensuring that the obtained aromatic compound has high polarity and is readily soluble in high-polarity solvents, and ensuring that the aromatic compound is resistant to thermal decomposition, the use of a nitrogen compound of formula (11-1) is preferable.

The present invention also provides the above manufacturing method wherein the aromatic compound represented by formula (7) is an aromatic compound represented by formula (8), and the aromatic compound represented by formula (3) is an aromatic compound represented by formula (4).

In the manufacturing method of the present invention, the leaving group represented by $X^3$ in the aromatic compound represented by formula (7) is preferably reacted with the nitrogen compound, the phosphorus compound, the sulfur compound, or a combination of two or more of these compounds.

The present invention provides an aromatic compound having a structural unit represented by the following formula (5).

[Chemical Formula 43]

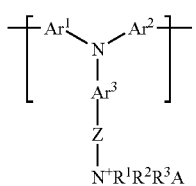

(5)

In the formula, each of $Ar^1$, $Ar^2$ and $Ar^3$ independently represents a divalent aromatic group which may be substituted, but at least two of $Ar^1$, $Ar^2$ and $Ar^3$ may be mutually bonded to form at least one ring, and Z, A, $R^1$, $R^2$ and $R^3$ are the same as defined above.

Each of $Ar^1$, $Ar^2$ and $Ar^3$ independently represents a divalent aromatic group which may have a substituent, and at least two of $Ar^1$, $Ar^2$ and $Ar^3$ may be mutually bonded to form a ring. Examples of the divalent aromatic group include divalent monocyclic aromatic groups such as a 1,3-phenylene group and 1,4-phenylene group; divalent condensed ring aromatic groups such as a naphthalene-1,3-diyl group, naphthalene-1,4-diyl group, naphthalene-1,5-diyl group, naphthalene-1,6-diyl group, naphthalene-1,7-diyl group, naphthalene-2,6-diyl group and naphthalene-2,7-diyl group; and divalent heteroaromatic groups such as a pyridine-2,5-diyl group, pyridine-2,6-diyl group, quinoxaline-2,6-diyl group and thiophene-2,5-diyl group. Among these, divalent monocyclic aromatic groups and divalent condensed ring aromatic groups are preferable, a group selected from the group, consisting of a 1,3-phenylene group, 1,4-phenylene group, naphthalene-1,4-diyl group, naphthalene-1,5-diyl group, naphthalene-2,6-diyl group and naphthalene-2,7-diyl group is more preferable, a 1,3-phenylene group or 1,4-phenylene group is still more preferable, and a 1,4-phenylene group is particularly preferable.

If the total of all the structural units in the aromatic compound having the structural unit represented by formula (5) is deemed 100 mol %, then the proportion of the structural unit represented by formula (5) is preferably within a range from not less than 1 mol % to not more than 100 mol %, more preferably within a range from not less than 1 mol % to not more than 99 mol %, still more preferably within a range from not less than mol % to not more than 90 mol %, still more preferably within a range from not less than 10 mol % to not more than 80 mol %, and particularly preferably within a range from not less than 20 mol % to not more than 70 mol %.

Specific examples of formula (5) include the aforementioned structural units (1a) to (1c), (1f), (1g), and (1i) to (1z).

Among these, (1a), (1b), (1c), (1l), (1k), (1m), (1n), (1p), (1q), (1r), (1s), (1t), (1v), (1y) and (1z) are preferable, (1a), (1c), (1l), (1p), (1q), (1r), (1t), (1y) and (1z) are more preferable, and (1a), (1c), (1r), (1t) and (1y) are still more preferable.

Furthermore, besides the structural unit represented by formula (5), the aromatic compound of the present invention may also include a structural unit represented by the above formula (12) as a repeating unit. Specific examples of the structural unit represented by formula (12) are as mentioned above. By including this type of structural unit, the hole injection properties of the aromatic compound of the present invention can be further improved. Preferred examples and particularly preferred examples of the structural unit represented by formula (12) are also as mentioned above.

The present invention provides an aromatic compound represented by the following formula (6).

[Chemical Formula 44]

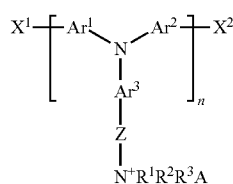

(6)

In the formula, $Ar^1$, $Ar^2$, $Ar^3$, A, Z, $R^1$, $R^2$ and $R^3$ represent the same meanings as defined above, and when a plurality of one or more of $Ar^1$, $Ar^2$, $Ar^3$, A, Z, $R^1$, $R^2$ and $R^3$ exists, each item of the plurality may be the same as, or different from, each other item of the plurality, and n, $X^1$ and $X^2$ are the same as defined above.

Specific examples of the aromatic compound represented by formula (6) include the aromatic compounds represented by the above formulas (2a) to (2c), (2f), (2g), and (2i) to (2z).

Among these, (2f), (2i), (2j), (2m), (2q), (2r), (2s), (2t), (2u), (2x) and (2z) are preferable, and (2i), (2j), (2m), (2q), (2r), (2t) and (2x) are more preferable.

In one embodiment of the present invention, the aromatic compound represented by formula (6) is an aromatic compound represented by the following formula (6-1), in which $X^6$ and $X^7$ are functional groups selected from the following group of functional groups and may be the same or different, and $Ar^1$, $Ar^2$, $Ar^3$, A, Z, $R^1$, $R^2$, $R^3$ and n represent the same meanings as defined above.

[Chemical Formula 45]

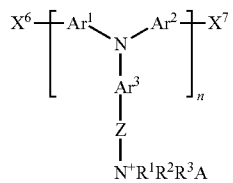

(6-1)

Group of functional groups: —Cl, —Br, —I, —O—SO$_2$—CH$_3$, —O—SO$_2$—CF$_3$, —O—SO$_2$-(p-C$_6$H$_4$)—CH$_3$, and —O—SO$_2$—C$_6$H$_5$ Specific examples of formula (6-1) include the aforementioned compounds (2a), (2c), (2l), (2f), (2g), (2k), (2n), (2o), (2p), (2u), (2v) and (2w).

In another embodiment of the present invention, the aromatic compound represented by formula (6) is an aromatic compound represented by the following formula (6-2), in which $X^8$ and $X^9$ are functional groups selected from the following group of functional groups and may be the same or different, and $Ar^1$, $Ar^2$, $Ar^3$, A, Z, $R^1$, $R^2$, $R^3$ and n represent the same meanings as defined above.

[Chemical Formula 46]

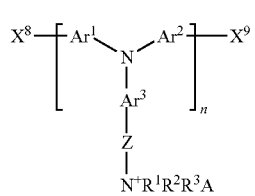

(6-2)

Group of functional groups: —B(OR$^5$)(OR$^6$) (wherein $R^5$ and $R^6$ represent the same meanings as defined above)

Specific examples of formula (6-2) include the aforementioned compounds (2b), (2l), (2y) and (2z).

The present invention further provides a manufacturing method in which the aromatic compound represented by formula (6-1) and/or formula (6-2) is used, and an $sp^2$ carbon-$sp^2$ carbon bond formation reaction is performed, thereby increasing the number of structural units represented by formula (5) and/or the value of n in formula (6). In this case, the same method as the aforementioned method used for manufacturing an aromatic compound having a structural unit represented by the above formula (3) and/or an aromatic compound represented by formula (4) can be used, using the aromatic compound represented by the aforementioned formula (4-1) and/or (4-2).

The present invention provides an aromatic compound having a structural unit represented by the following formula (9).

[Chemical Formula 47]

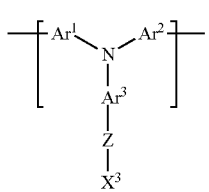

(9)

In the formula, $Ar^1$, $Ar^2$, $Ar^3$, Z and $X^3$ are the same as defined above.

Examples of the structural unit represented by formula (9) include the structural units (3a) to (3w) mentioned above.

Among these, (3a), (3b), (3c), (3d), (3e), (3f), (3g), (3i), (3j), (3l), (3n), (3o), (3p), (3q), (3r), (3s), (3v) and (3w) are preferable, (3a), (3c), (3d), (3i), (3l), (3n), (3p), (3q), (3r), (3s), (3v) and (3w) are more preferable, (3a), (3c), (3d), (3i), (3l), (3n), (3r), (3s) and (3v) are still more preferable, and (3a), (3c), (3d), (3i), (3r) and (3s) are still more preferable.

If the total of all the structural units in the aromatic compound having the structural unit represented by formula (9) is deemed 100 mol %, then the proportion of the structural unit represented by formula (9) is preferably within a range from not less than 1 mol % to not more than 100 mol %, more preferably within a range from not less than 1 mol % to not more than 99 mol %, still more preferably within a range from not less than mol % to not more than 90 mol %, still more preferably within a range from not less than 10 mol % to not more than 80 mol %, and particularly preferably within a range from not less than 20 mol % to not more than 70 mol %.

The present invention further provides an aromatic compound represented by the following formula (10).

[Chemical Formula 48]

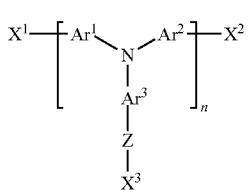

(10)

In the formula, Z, $Ar^1$, $Ar^2$, $Ar^3$ and $X^3$ represent the same meanings as defined above, and when a plurality of one or more of Z, $Ar^1$, $Ar^2$, $Ar^3$ and $X^3$ exists, each item of the plurality may be the same as, or different from, each other item of the plurality, and n, $X^1$ and $X^2$ are the same as defined above.

Examples of formula (10) include the aforementioned formulas (4a) to (4z).

Among these, (4a), (4b), (4c), (4d), (4e), (4f), (4g), (4i), (4j), (4l), (4n), (4o), (4p), (4q), (4r), (4s), (4v), (4w), (4y) and (4z) are preferable, (4a), (4c), (4d), (4i), (4l), (4n), (4p), (4q), (4r), (4s), (4v) and (4w) are more preferable, (4a), (4c), (4d), (4i), (4l), (4n), (4r), (4s) and (4v) are still more preferable, and (4a), (4c), (4d), (4i), (4r) and (4s) are still more preferable.

In one embodiment of the present invention, the aromatic compound represented by formula (10) is an aromatic compound represented by the following formula ($10^{-1}$), in which $X^6$ and $X^7$ are, in the same manner as described above, functional groups selected from the following group of functional groups, and may be the same or different, and $Ar^1$, $Ar^2$, $Ar^3$, Z, $X^3$ and n represent the same meanings as defined above.

[Chemical Formula 49]

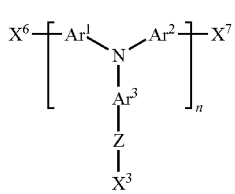

(10-1)

Group of functional groups: —Cl, —Br, —I, —O—$SO_2$—$CH_3$, —O—$SO_2$—$CF_3$, —O—$SO_2$-(p-$C_6H_4$)—$CH_3$, and —O—$SO_2$—$C_6H_5$ Specific examples of formula (10-1) include the aforementioned compounds (4a), (4c), (4d), (4e), (4g), (4h), (4k), (4n), (4o), (4p), (4v) and (4w).

In another embodiment of the present invention, the aromatic compound represented by formula (10) is an aromatic compound represented by the following formula (10-2), in which $X^8$ and $X^9$ are, in the same manner as described above, functional groups selected from the following group of functional groups, and may be the same or different, and $Ar^1$, $Ar^2$, $Ar^3$, Z, $X^3$ and n represent the same meanings as defined above.

[Chemical Formula 50]

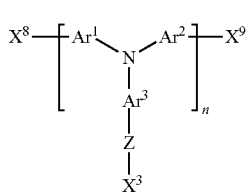

(10-2)

Group of functional groups: —B($OR^5$)($OR^6$) (wherein $R^5$ and $R^6$ represent the same meanings as defined above)

Specific examples of formula (10-2) include the aforementioned compounds (4b), (4h), (4l) and (4y).

The present invention further provides a method for manufacturing an aromatic compound having a structural unit rep resented by the above formula (5), the method comprising reacting a leaving group represented by $X^3$ in the aromatic compound represented by formula (9) with a nitrogen compound represented by the above formula (11-1), thereby converting the aromatic compound into an ammonium salt.

Tertiary amine compounds can be used favorably as the nitrogen compound represented by formula (11-1). Specific examples of such nitrogen compounds include trimethylamine, triethylamine, tri-1-propylamine, tri-2-propylamine, tri-n-butylamine, tri-2-butylamine, tri-1-pentylamine, tri-2-pentylamine, tri-3-pentylamine, trineopentylamine, tricyclopentylamine, tri-1-hexylamine, tri-2-hexylamine, tri-3-hexylamine, pyridine, N-methylimidazole, N-methylpyrrolidine and N-methylmorpholine.

The present invention also provides the above manufacturing method wherein the aromatic compound represented by formula (9) is an aromatic compound represented by formula (10), and the aromatic compound represented by formula (5) is an aromatic compound represented by formula (6).

Further, the present invention provides the above manufacturing method wherein the aromatic compound represented by formula (9) is an aromatic compound represented by formula (10-1), and the aromatic compound represented by formula (5) is an aromatic compound represented by formula (6-1).

Moreover, the present invention provides the above manufacturing method wherein the aromatic compound represented by formula (9) is an aromatic compound represented by formula (10-2), and the aromatic compound represented by formula (5) is an aromatic compound represented by formula (6-2).

The present invention further provides a manufacturing method in which the compound represented by the above formula (10) is used, and an $sp^2$ carbon-$sp^2$ carbon bond formation reaction is performed, thereby increasing the number of structural units represented by the above formula (9) and/or the value of n in the aromatic compound represented by formula (10). In this case, the aforementioned method for manufacturing an aromatic compound having a structural unit represented by formula (3) and/or an aromatic compound represented by formula (4) can be applied in the same manner.

The aromatic compound of the present invention can also be used in the form of a composition comprising the aromatic compound of the present invention.

Using the aromatic compound of the present invention, a film formed from the aromatic compound of the present invention and/or a composition containing the same can also be produced.

Embodiments of the present invention have been described above, but the embodiments of the present invention disclosed in the above description are merely exemplary, and the scope of the present invention is in no way limited by these embodiments. The scope of the present invention is indicated by the scope of the claims, and includes all modifications having an equivalent meaning to the claims or included within the scope of the claims.

EXAMPLES

The present invention is described below based on a series of examples, but the present invention is in no way limited by these examples.

Example 1

Synthesis of Compound 1

[Chemical Formula 51]

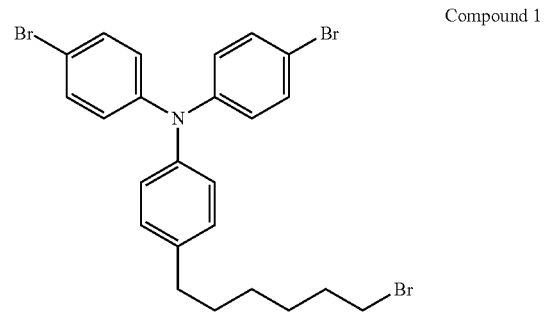

Compound 1

To a THF solution of tri(4-bromophenyl)amine (0.2 mol/L, amount of tri(4-bromophenyl)amine: 100 g, 0.21 mol) cooled to −60° C. (internal temperature, using a dry ice-acetone bath), tert-BuLi (1.6 mol/L pentane solution, 1.5 equivalents relative to the amount of tri(4-bromophenyl)amine) was added over a period of 15 minutes so that the temperature did not exceed −55° C., and the resulting mixture was then added to a solution of 1,6-dibromohexane (1.0 mol/L THF solution, 5.0 equivalents relative to the amount of tri(4-bromophenyl) amine) that had been prepared separately at −60° C. (internal temperature), with the addition performed in several portions using a syringe so that the internal temperature did not exceed −55° C.

This reaction solution was removed from the cooling bath, and then returned to room temperature over a period of 30 minutes under constant stirring. When the internal temperature reached 15° C., the reaction was stopped. The oily substance obtained by removing the solvent by distillation under reduced pressure was subjected to further distillation under reduced pressure to remove the residual 1,6-dibromohexane, yielding a viscous yellow oily substance. This substance was dissolved in 500 mL of ethyl acetate, and the resulting solution was washed with 500 mL of 0.1 mol/L hydrochloric acid and 500 mL of a saturated saline solution, and then dried over anhydrous sodium sulfate. The solvent was then removed by distillation under reduced pressure, yielding 115 g of a crude product.

Purification was performed by silica gel column chromatography (developing solvent: ethyl acetate/hexane, used with a linear concentration gradient from a volume ratio of 1/200 to 1/40), yielding a mixture containing the compound 1 as a colorless viscous oil (26.9 g). When this colorless viscous oil was subjected to HPLC under the following conditions, the compound 1 was able to be isolated. Based on the HPLC area percentage, the amount of the compound 1 within the above mixture was calculated as 24.1 g (yield: 21%).

HPLC Conditions

Model: SPD-100AV/LC-10AT/DGU-3A/SCL-10AVP/SIL-10A/C—$R^5A$ (Shimadzu)

Column: Mightysil RP-18GP (5 μm, 6 mm id, 15 cm, Kanto Chemical)

Mobile phase: acetonitrile/water=95/5 (volume ratio), flow rate: 1.0 mL/min.

Detection wavelength: 254 nm

Column temperature: 40° C.

$^1$H-NMR (400 MHz, CDCl$_3$, model: Bruker Advance 400): δ 1.3 to 2.6 ppm (m, —CH$_2$— of compound 1), 3.4 ppm (t, —CH$_2$Br of compound 1), 6.9 to 7.3 ppm (m, aromatic rings of compound 1)

Method of Measuring Polymer Molecular Weight

The polystyrene-equivalent number-average molecular weight (Mn) and weight-average molecular weight (Mw) were determined by size exclusion chromatography (SEC) under the following conditions.

Apparatus: HLC-8220GPC manufactured by Tosoh Corporation

Columns: the following four columns connected in series:
TSK guard column Super MPHZ-M (manufactured by Tosoh): 1 column
TSKgel Super Multipore HZ-M (manufactured by Tosoh): 3 columns Mobile phase: tetrahydrofuran
Detector: differential refractive index detector

Example 2

Synthesis of Compound 2

[Chemical Formula 52]

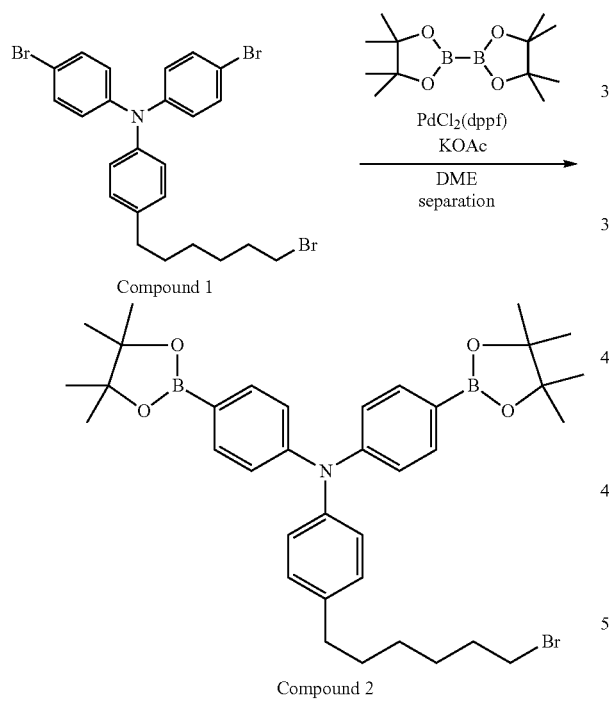

Compound 2

To 300 mL of a 1,2-dimethoxyethane solution of the compound 1 (12.5 g of the mixture described in Example 1 was used, equivalent to 11.3 g=20 mmol of the pure compound) subjected to nitrogen bubbling for 30 minutes, 27.7 g (109 mmol) of bis(pinacolato)diboron and potassium acetate (48.3 g, 493 mmol) were added and stirred thoroughly, then, a PdCl$_2$(dppf)/CH$_2$Cl$_2$ solution (amount of PdCl$_2$(dppf): 1.0 g, 1.2 mmol) was added to the mixture, and the resulting mixture was stirred at 80° C. for two hours. The reaction mixture was then returned to 23° C., poured into 1,500 mL of water, and then extracted three times with 250 mL samples of ethyl acetate. The ethyl acetate extracts were combined, washed with 500 mL of a saturated saline solution, and then dried over anhydrous sodium sulfate. The mixture obtained upon removal of the solvent by distillation under reduced pressure was purified by silica gel column chromatography (developing solvent: ethyl acetate/hexane, used with a linear concentration gradient from a volume ratio of 1/100 to 1/10), yielding 8.3 g of the compound 2 (white solid, yield: 65%, purity from HPLC: 100%).

The HPLC conditions and NMR conditions were the same as those for Example 1.

$^1$H-NMR (400 MHz, CDCl$_3$): δ 1.3 ppm (s, 24H, —CH$_3$), 1.3 to 2.6 ppm (m, 10H, —CH$_2$—), 3.4 ppm (t, 2H, —CH$_2$Br), 7.0 to 7.7 ppm (m, 12H of compound 2 aromatic rings)

Example 3

Conversion to Quaternary Ammonium Salt

By reacting the mixture containing the compound 1, obtained in Example 1, with triethylamine, the compound 1 can be converted to a quaternary ammonium salt compound (compound 3).

[Chemical Formula 53]

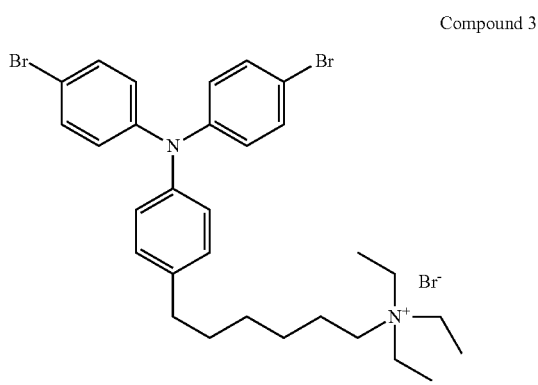

Compound 3

Example 4

Polymerization of Compound 2

By subjecting the compound 2 obtained in Example 2 to a condensation polymerization with a substantially equimolar amount of an arylene dihalide compound via the Suzuki coupling reaction in the presence of Pd(PPh$_3$)$_4$ and an alkali, a polymer having a bromoalkyl group can be obtained. By reacting this polymer with triethylamine, the polymer can be converted to a polymer having a quaternary ammonium salt. This polymer can be used as a hole injection material.

Example 5

Polymerization of Compound 3

By subjecting molecules of the compound 3 obtained in Example 3 to a condensation polymerization via a coupling reaction using a Ni(0) catalyst, a polymer having a quaternary ammonium salt can be obtained. This polymer can be used as a hole injection material.

Example 6

Synthesis of Polymer Having Bromoalkyl Group by Copolymerization of Compound 2

Using a three-neck round-bottom flask, and within a nitrogen atmosphere at 23° C., 0.98 g (1.48 mmol) of the compound 2 obtained in Example 2 and 0.46 g of 2,5-dimethoxy-1,4-dibromobenzene (manufactured by Aldrich, 1.50 mmol) were dissolved in 86 ml of THF, and the thus obtained solution was subjected to nitrogen bubbling for 40 minutes. Following completion of the bubbling, the solution was immersed in an 80° C. oil bath, and the temperature was raised to 80° C. Subsequently, 0.019 g of tetrakis(triphenylphosphine)palladium Pd(PPh$_3$)$_4$ (manufactured by Aldrich, 0.016 mmol) was added to the solution to obtain a reaction mixture.

A solution prepared by dissolving 1.02 g of potassium carbonate (manufactured by Wako Pure Chemical Industries, 7.4 mmol) in 12 ml of pure water and then performing nitrogen bubbling for 40 minutes was added dropwise to the above reaction mixture over a period of 15 minutes. Subsequently, with the temperature of the oil bath maintained at 80° C., the reaction mixture was stirred for 7 hours. No solid fraction precipitation was observed in the reaction mixture, and each of the components remained completely dissolved.

The reaction mixture was then cooled to 23° C., nitrogen bubbling was performed for 40 minutes, and 0.018 g of phenylboronic acid (manufactured by Aldrich; 0.15 mmol) was then added to the reaction mixture. The thus obtained mixture was immersed in an 80° C. oil bath, and the temperature was raised to 80° C. Subsequently, 0.018 g of tetrakis(triphenylphosphine)palladium Pd(PPh$_3$)$_4$ (manufactured by Aldrich, 0.016 mmol) was added to the mixture, and the mixture was stirred for 9 hours.

The thus obtained reaction mixture was cooled to 23° C., and added dropwise to a large excess of a mixed solution of methanol:water=400 ml: 100 ml. The precipitated polymer was separated by suction filtration, washed with a solution of methanol:water-4:1 (volume ratio), and then dried under vacuum, yielding 0.62 g (yield: 77%) of a polymer.

[Chemical Formula 54]

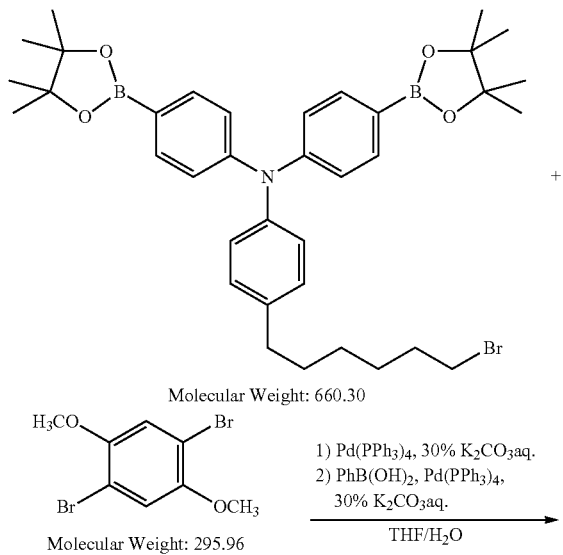

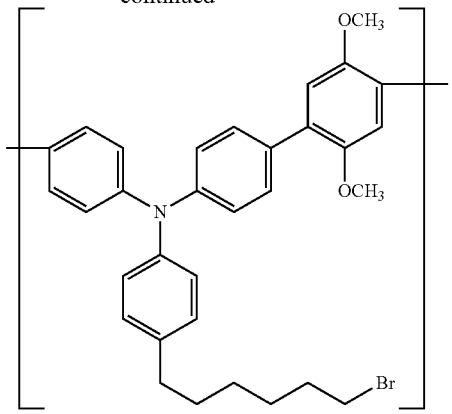

$^1$H-NMR (300 MHz, CDCl$_3$): δ 1.3 to 1.9 ppm (m, 8H, —CH$_2$—), 2.6 ppm (t, 2H, —CH$_2$—Ar), 3.4 ppm (t, 2H, —CH$_2$Br), 4.8 ppm (s, 6H, —OCH$_3$), 6.8 to 7.7 ppm (m, 14H, aromatic rings)

SEC: Mn=4.7×10$^3$, Mw=6.3×10$^3$

Example 7

Synthesis of Polymer Having Bromoalkyl Group by Copolymerization of Compound 2

Using a three-neck round-bottom flask, and within a nitrogen atmosphere at 23° C., 0.164 g (0.247 mmol) of the compound 2 obtained in Example 2 and 0.059 g of 1,3-dibromobenzene (manufactured by Tokyo Chemical Industry, 0.250 mmol) were dissolved in 16 ml of THF, and the thus obtained solution was subjected to nitrogen bubbling for 40 minutes. Following completion of the bubbling, the solution was immersed in an 80° C. oil bath, and the temperature was raised to 80° C. Subsequently, 0.0029 g of tetrakis(triphenylphosphine)palladium Pd(PPh$_3$)$_4$ (manufactured by Aldrich, 0.0025 mmol) was added to the solution to obtain a reaction mixture.

A solution prepared by dissolving 0.17 g of potassium carbonate (manufactured by Wako Pure Chemical Industries, 1.23 mmol) in 12 ml of pure water and then performing nitrogen bubbling for 40 minutes was added dropwise to the above reaction mixture over a period of 15 minutes. Subsequently, with the temperature of the oil bath maintained at 80° C., the reaction mixture was stirred for 6 hours. No solid fraction precipitation was observed in the reaction mixture, and each of the components remained completely dissolved.

The reaction mixture was then cooled to 23° C., nitrogen bubbling was performed for 40 minutes, and 0.0030 g of phenylboronic acid (manufactured by Aldrich, 0.025 mmol) was then added to the reaction mixture. The thus obtained mixture was immersed in an 80° C. oil bath, and the temperature was raised to 80° C. Subsequently, 0.0029 g of tetrakis(triphenylphosphine)palladium Pd(PPh$_3$)$_4$ (manufactured by Aldrich, 0.0025 mmol) was added to the mixture, and the mixture was stirred for 9 hours.

The thus obtained reaction mixture was cooled to 23° C., and added dropwise to a large excess of a mixed solution of methanol:water=100 ml:20 ml. The precipitated polymer was separated by suction filtration, washed with a solution of methanol:water=4:1 (volume ratio), and then dried under vacuum, yielding 0.077 g (yield: 64%) of a polymer.

[Chemical Formula 55]

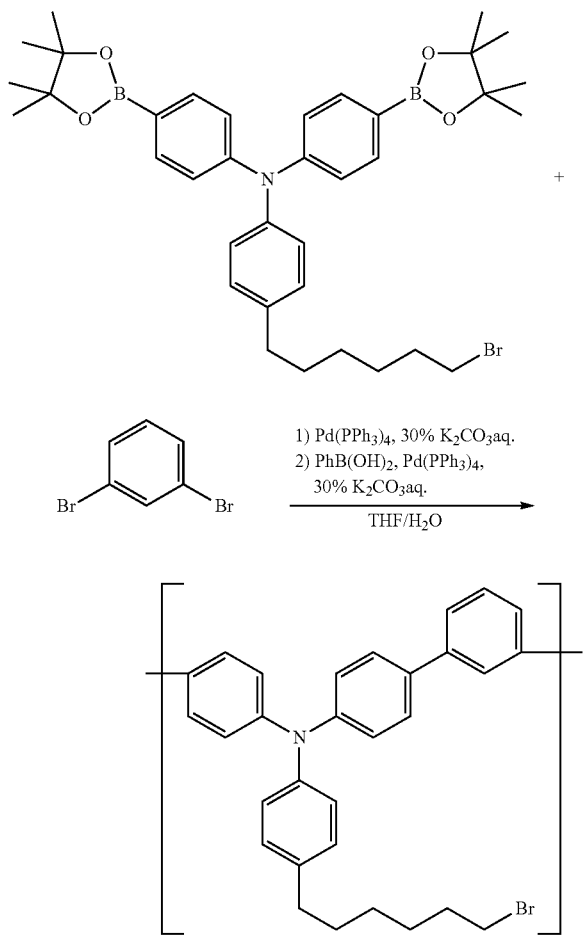

[Chemical Formula 56]

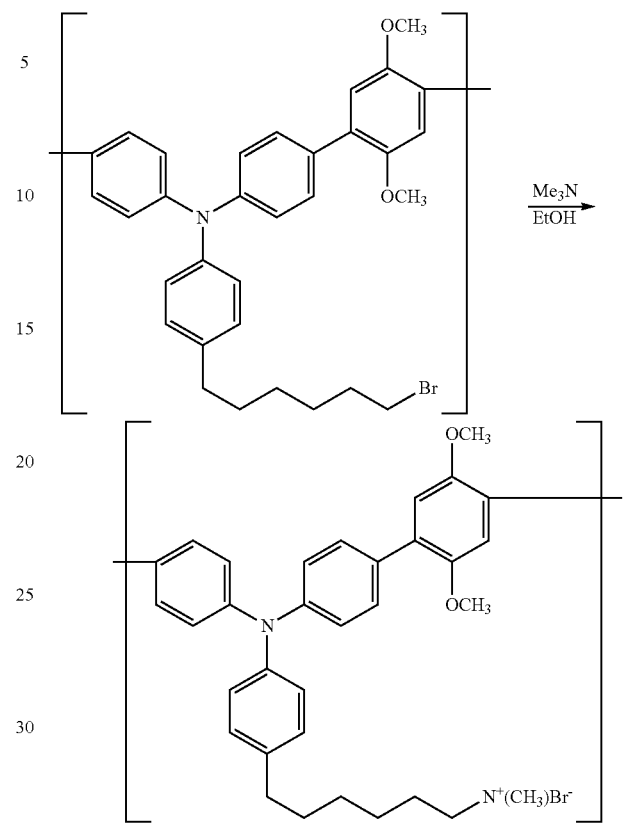

¹H-NMR (300 MHz, CDCl₃): δ 1.2 to 2.0 ppm (m, 8H, —CH₂—), 2.6 ppm (t, 2H, —CH₂—Ar), 3.4 ppm (t, 2H, —CH₂Br), 6.8 to 7.9 ppm (m, 14H, aromatic rings)

Example 8

Conversion of Polymer Described in Example 6 to Quaternary Ammonium Salt

A sample of 0.70 g of the polymer obtained using the method described in Example 6 (equivalent to 1.23 mmol of the repeating structural unit) was dispersed in 30 ml of a 4.2 mol/L ethanol solution of trimethylamine (manufactured by Aldrich, 126 mmol), and the dispersion was stirred at 23° C. for three days. The solvent was then removed from the resulting reaction mixture by distillation, and the mixture was dried under reduced pressure, yielding 0.71 g (yield: 96%) of a quaternary ammonium salt polymer. It was confirmed that the thus obtained polymer dissolved in methanol at 10% by weight.

¹H-NMR (300 MHz, DMSO-d₆): δ 1.3 to 1.9 ppm (m, 8H, —CH₂—), 2.3 ppm (t, 2H, —CH₂—Ar), 3.1 ppm (s, 9H, —N⁺(CH₃)₃), 3.4 ppm (t, 2H, —CH₂N⁺), 3.7 to 4.0 ppm (m, 6H, —OCH₃), 6.8 to 7.7 ppm (m, 14H, aromatic rings)

Elemental analysis (N measured by a flask combustion method, and Br measured by a flask combustion-ion chromatography method. This also applies to subsequent elemental analyses)

N: 4.2% by weight (calculated value: 4.5% by weight)
Br: 13.8% by weight (calculated value: 12.9% by weight)

Example 9

Replacement of Counter Anion of Quaternary Ammonium Salt Described in Example 8

A sample of 0.30 g of the polymer synthesized using the method described in Example 8 (equivalent to 0.486 mmol of the repeating structural unit) was dissolved in 3.0 ml of N,N-dimethylformamide (manufactured by Wako Pure Chemical Industries) at 25° C. under a nitrogen atmosphere, 0.11 g of sodium trifluoromethanesulfonate (0.631 mmol, manufactured by Wako Pure Chemical Industries) was added to the solution, and the mixture was stirred for 10 hours. The reaction solution was then added dropwise to 100 ml of ion-exchanged water, and the precipitated polymer was extracted by suction filtration. The thus obtained polymer was washed by dispersion and stirring in 50 ml of ion-exchanged water, and suction filtration was then used to extract the polymer. This process was repeated twice, and the resulting polymer was then dried under reduced pressure at 40° C., yielding 0.18 g of a quaternary ammonium salt polymer having an introduced trifluoromethanesulfonate ion.

The results of elemental analysis revealed that a polymer represented by the following composition formula had been obtained, in which 70 mol % of the bromide anions had been substituted with trifluoromethanesulfonate anions. Because no sodium content was detected, it was clear that the excess sodium trifluoromethanesulfonate had been removed in the extraction step.

[Chemical Formula 57]

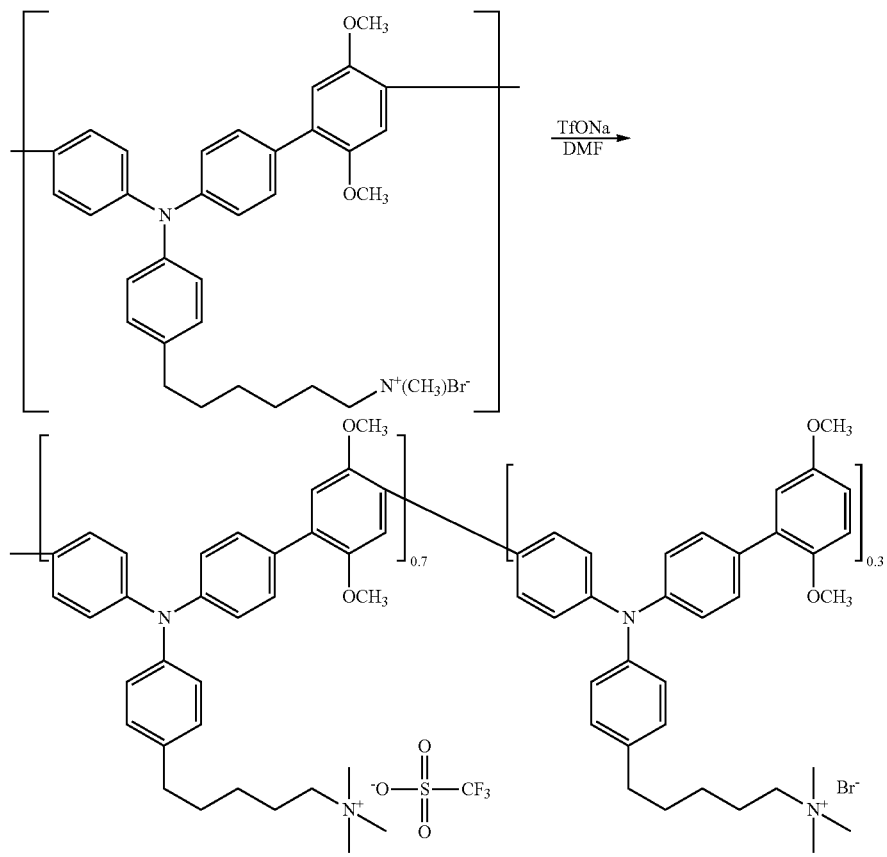

$^1$H-NMR (300 MHz, DMSO-d$_6$): δ 1.3 to 1.9 ppm (m, 8H, —CH$_2$—), 2.6 ppm (t, 2H, —CH$_2$—Ar), 3.1 ppm (s, 9H, —N$^+$(CH$_3$)$_3$), 3.3 ppm (t, 2H, —CH$_2$N$^+$), 3.7 to 4.0 ppm (m, 6H, —OCH$_3$), 7.0 to 7.6 ppm (m, 14H, aromatic rings)

$^{19}$F-NMR (280 MHz, DMSO-d$_6$): 6-78 ppm (s, 3F, —CF$_3$)

Elemental analysis (F measured by a flask combustion-ion chromatography method, and Na measured by a sulfonitric acid decomposition-hydrochloric acid decomposition-ICP emission analysis method)

N, 4.0% by weight (calculated value: 4.2% by weight)
Br: 4.7% by weight (calculated value: 3.6% by weight)
F: 5.8% by weight (calculated value: 6.0% by weight)
Na: 0.0% by weight (calculated value: 0.0% by weight)

HOMO-LUMO measurements were performed for the polymers described in Example 8 and Example 9. A polymer solution was spin-coated onto a glass substrate.

Measurement Method:

The orbital energy of the highest occupied molecular orbital (HOMO) of the polymer was determined by measuring the ionization potential of the polymer, and using the obtained ionization potential as the orbital energy. On the other hand, the orbital energy of the lowest unoccupied molecular orbital (LUMO) was determined by determining the energy difference between the HOMO and the LUMO, and then using the sum of this energy difference and the previously measured ionization potential as the orbital energy. A photoelectron spectrometer (AC-2, manufactured by Riken Keiki Co., Ltd.) was used for measurement of the ionization potential. Further, the energy difference between the HOMO and the LUMO was determined by measuring the absorption spectrum of the polymer using a ultraviolet-visible-near infrared spectrophotometer (Cary 5E, manufactured by Varian, Inc.), and then determining the energy difference from the absorption edge.

Polymer of Example 8: HOMO −5.18 eV, LUMO −2.31 eV
Polymer of Example 9: HOMO −5.35 eV, LUMO −2.47 eV Example 10 or 11

Evaluation of Hole Injection Properties of the Polymer Described in Example 8 or Example 9

A hole-only device was prepared, and the hole injection properties of the polymer described in Example 8 or Example 9 were evaluated. The device structure had the following configuration.

ITO/hole injection-transport layer formed from the polymer of Example 8 or 9 (30 to 40 nm)/intermediate layer that functions as hole transport layer (100 nm)/Au (100 nm)

Example 10

Preparation of Hole-Only Device 1

The polymer synthesized in Example 8 (hereafter also referred to as "polymer 1") was mixed with methanol to obtain a hole injection-transport layer-forming composition containing 1.5% by weight of the polymer 1.

The above hole injection-transport layer-forming composition was applied to an ITO anode (thickness: 45 nm) that had been formed and patterned on the surface of a glass substrate, and a spin-coating method was used to form a hole injection-transport layer having a thickness of 30 nm. The glass substrate having the hole injection-transport layer formed thereon was heated at 180° C. for 10 minutes under an inert atmosphere (nitrogen atmosphere), and the substrate was then left to cool naturally to room temperature, yielding a substrate having a hole injection-transport layer formed thereon.

Next, a hole transport polymer material was mixed with xylene to obtain a hole transport layer-forming composition containing 0.7% by weight of the hole transport polymer material.

The hole transport polymer material was synthesized by the following method.

Under an inert gas atmosphere, 2,7-dibromo-9,9-di(octyl)fluorene (1.4 g), 2,7-bis(4,4,5,5-tetramethyl-1,3,2-dioxaborolan-2-yl)-9,9-di(octyl)fluorene (6.4 g), N,N-bis(4-bromophenyl)-N',N'-bis(4-butylphenyl)-1,4-phenylenediamine (4.1 g), bis(4-bromophenyl)benzocyclobuteneamine (0.6 g), tetraethylammonium hydroxide (1.7 g), palladium acetate (4.5 mg), tri(2-methoxyphenyl)phosphine (0.03 g) and toluene (100 mL) were mixed, and the resulting mixture was stirred under heat at 100° C. for 2 hours. Subsequently, phenylboronic acid (0.06 g) was added, and the resulting mixture was stirred for 10 hours. After cooling, the water layer was removed, and an aqueous solution of sodium diethyldithiocarbamate was added and stirred. Subsequently, the water layer was removed, and the organic layer was washed with water and then a 3% by weight aqueous solution of acetic acid. The organic layer was then poured into methanol to precipitate the polymer, and the polymer was collected by filtration, redissolved in toluene, and passed through a column of silica gel and alumina. The eluted toluene solution containing the polymer was collected, and the collected toluene solution was poured into methanol to precipitate the polymer. The precipitated polymer was filtered, and then dried under vacuum at 50° C., yielding a hole transport polymer material. The polystyrene-equivalent weight-average molecular weight of the hole transport polymer material was $3.0 \times 10^5$.

The hole transport layer-forming composition was applied by a spin-coating method to the hole injection-transport layer of the aforementioned substrate having a hole injection-transport layer formed thereon, thus obtaining a film having a thickness of 100 nm. The substrate provided with this film was heated at 180° C. for 10 minutes under an inert atmosphere (nitrogen atmosphere) to make the film insoluble, and the substrate was then left to cool naturally to room temperature, yielding a substrate having a hole transport layer formed thereon.

The substrate having the hole transport layer formed thereon, obtained in the manner described above, was placed inside a vacuum apparatus, and a vacuum deposition method was used to deposit 100 nm of Au on the above layer, thereby forming a cathode and producing a layered structure 1.

The layered structure 1 obtained above was removed from the vacuum apparatus, and was then sealed, under an inert atmosphere (nitrogen atmosphere), with a sealing glass and a two-component epoxy resin to obtain a hole-only device 1.

Example 11

Preparation of Hole-Only Device 2

The polymer synthesized in Example 9 (hereafter also referred to as "polymer 2") was mixed with methanol to obtain a hole injection-transport layer-forming composition containing 1.5% by weight of the polymer 2.

The above hole injection-transport layer-forming composition was applied to an ITO anode (thickness: 45 nm) that had been formed and patterned on the surface of a glass substrate, and a spin-coating method was used to form a hole injection-transport layer having a thickness of 40 nm. The glass substrate having the hole injection-transport layer formed thereon was heated at 180° C. for 60 minutes under an inert atmosphere (nitrogen atmosphere), and the substrate was then left to cool naturally to room temperature, yielding a substrate having a hole injection-transport layer formed thereon.

Next, a hole transport polymer material was mixed with xylene to obtain a hole transport layer-forming composition containing 0.7% by weight of the hole transport polymer material. The hole transport polymer material was the material synthesized using the method described in Example 10, and had a polystyrene-equivalent weight-average molecular weight of $3.0 \times 10^5$.

The hole transport layer-forming composition was applied by a spin-coating method to the hole injection-transport layer of the aforementioned substrate having a hole injection-transport layer formed thereon, thus obtaining a film having a thickness of 100 nm. The substrate provided with this film was heated at 180° C. for 10 minutes under an inert atmosphere (nitrogen atmosphere) to make the film insoluble, and the substrate was then left to cool naturally to room temperature, yielding a substrate having a hole transport layer formed thereon.

The substrate having the hole transport layer formed thereon, obtained in the manner described above, was placed inside a vacuum apparatus, and a vacuum deposition method was used to deposit 100 nm of Au on the above layer, thereby forming a cathode and producing a layered structure 2.

The layered structure 2 obtained above was removed from the vacuum apparatus, and was then sealed, under an inert atmosphere (nitrogen atmosphere), with a sealing glass and a two-component epoxy resin to obtain a hole-only device 2.

Comparative Example 1

Preparation of Hole-Only Device C1

With the exception of not forming the hole injection-transport layer in Example 10, operations were performed in the same manner as Example 10 to obtain a hole-only device C1.

[Measurement]

A reverse voltage of 4.0 V was applied to the hole-only devices 1, 2 and C1 obtained in the manner described above, and the current density was measured. The results are shown in Table 1.

TABLE 1

| | Polymer | Cathode | Current density (mA/cm²) |
|---|---|---|---|
| Example 10 (hole-only device 1) | polymer 1 | Au | $8.5 \times 10^{-2}$ |
| Example 11 (hole-only device 2) | polymer 2 | Au | $8.7 \times 10^{-2}$ |
| Comparative Example 1 (hole-only device C1) | none | Au | $1.9 \times 10^{-3}$ |

As is evident from Table 1, the hole-only devices comprising the aromatic compound of the present invention exhibited superior current density compared with the hole-only device that did not contain the aromatic compound.

Based on the above, it is clear that the aromatic compound of the present invention having an onium ion, and particularly at least one of a primary to quaternary ammonium ion, and especially a quaternary ammonium ion, on a hydrocarbon side chain, and particularly an alkyl side chain, can be applied to layered structures and electronic devices, and can be used particularly favorably as a hole injection material that can achieve a higher current density at a given voltage, and is therefore extremely useful.

The invention claimed is:

1. A layered structure having a substrate, and a hole injection and/or hole transport layer comprising an aromatic compound having a structural unit represented by formula (1) and a structural unit represented by formula (12) below:

[Chemical Formula 1]

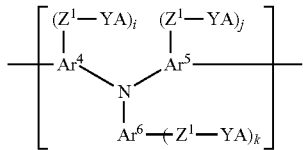
(1)

wherein $Ar^4$ represents an (i+2)-valent aromatic group which may have a substituent, $Ar^5$ represents a (j+2)-valent aromatic group which may have a substituent, and $Ar^6$ represents a (k+1)-valent aromatic group which may have a substituent, but at least two of $Ar^4$, $Ar^5$ and $Ar^6$ may be mutually bonded to form at least one ring, each $Z^1$ independently represents a divalent group, each Y independently represents a group represented by formula (2-1), (2-2) or (2-3) below, each A independently represents a monovalent or divalent or higher anion, and when at least one A is a divalent or higher anion, the structural unit may further have another cation, and each of i, j and k independently represents an integer of 0 or greater, provided that i+j+k is an integer of 1 or greater, $$-N^+R^1R^2R^3 \quad (2\text{-}1)$$

$$-P^+R^1R^2R^3 \quad (2\text{-}2)$$

$$-S^+R^1R^2 \quad (2\text{-}3)$$

wherein for each of formulas (2-1), (2-2) and (2-3), each of $R^1$, $R^2$ and $R^3$ independently represents a hydrogen atom or a monovalent hydrocarbon group which may have a substituent, but at least two of $R^1$, $R^2$ and $R^3$ may be mutually bonded to form at least one ring, and

[Chemical Formula 19]

(12)

wherein $Ar^7$ represents a divalent aromatic group, and some or all of the hydrogen atoms in the aromatic group may be substituted with a group selected from the group consisting of a fluorine atom, an alkyl group of 1 to 20 carbon atoms which may have a substituent, an alkoxy group of 1 to 20 carbon atoms which may have a substituent, an aryl group of 6 to 20 carbon atoms which may have a substituent, an aryloxy group of 6 to 20 carbon atoms which may have a substituent, and an acyl group of 2 to 20 carbon atoms which may have a substituent.

2. The layered structure according to claim 1, wherein the hole injection and/or hole transport layer has a crosslinked structure.

3. An electronic device having the layered structure according to claim 1.

4. A layered structure having a substrate, and at least one of a hole injection layer and a hole transport layer both comprising an aromatic compound having a structural unit represented by formula (1) below:

wherein at least one of the hole injection layer and the hole transport layer has a cross-linked structure,

[Chemical Formula 1]

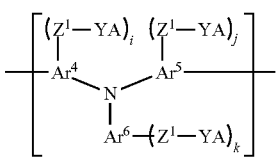
(1)

wherein $Ar^4$ represents an (i+2)-valent aromatic group which may have a substituent, $Ar^5$ represents a (j+2)-valent aromatic group which may have a substituent, and $Ar^6$ represents a (k+1)-valent aromatic group which may have a substituent, but at least two of $Ar^4$, $Ar^5$ and $Ar^6$ may be mutually bonded to form at least one ring, each $Z^1$ independently represents a divalent group, each Y independently represents a group represented by formula (2-1), (2-2) or (2-3) below, each A independently represents a monovalent or divalent or higher anion, and when at least one A is a divalent or higher anion, the structural unit may further have another cation, and each of i, j and k independently represents an integer of 0 or greater, provided that i+j+k is an integer of 1 or greater, $$-N^+R^1R^2R^3 \quad (2\text{-}1)$$

$$-P^+R^1R^2R^3 \quad (2\text{-}2)$$

$$-S^+R^1R^2 \quad (2\text{-}3)$$

wherein for each of formulas (2-1), (2-2) and (2-3), each of $R^1$, $R^2$ and $R^3$ independently represents a hydrogen atom or a monovalent hydrocarbon group which may have a substituent, but at least two of $R^1$, $R^2$ and $R^3$ may be mutually bonded to form at least one ring.

5. An electronic device having the layered structure according to claim 4.

* * * * *